United States Patent
Venus et al.

(10) Patent No.: US 10,533,163 B2
(45) Date of Patent: Jan. 14, 2020

(54) RECOMBINANT NUCLEOSIDE-SPECIFIC RIBONUCLEASE AND METHOD OF PRODUCING AND USING SAME

(71) Applicant: University Of Cincinnati, Cincinnati, OH (US)

(72) Inventors: Sarah Venus, Richfield, OH (US); Balasubrahmanyam Addepalli, Mason, OH (US); Nicholas Paul Lesner, Amherst, OH (US); Patrick Alan Limbach, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 15/568,260

(22) PCT Filed: Apr. 25, 2016

(86) PCT No.: PCT/US2016/029151
§ 371 (c)(1),
(2) Date: Oct. 20, 2017

(87) PCT Pub. No.: WO2016/172678
PCT Pub. Date: Oct. 27, 2016

(65) Prior Publication Data
US 2018/0320154 A1    Nov. 8, 2018

Related U.S. Application Data

(60) Provisional application No. 62/151,546, filed on Apr. 23, 2015, provisional application No. 62/151,640, filed on Apr. 23, 2015.

(51) Int. Cl.
*C12N 9/22*     (2006.01)
*C12Q 1/6869*   (2018.01)
*C12Q 1/6806*   (2018.01)

(52) U.S. Cl.
CPC ............. *C12N 9/22* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

2012/0167245 A1    6/2012   Abad et al.

FOREIGN PATENT DOCUMENTS

WO    2008103763 A2    8/2008

OTHER PUBLICATIONS

GenBank Accession No. KGN59560, Oct. 2014.*
International Search Authority, PCT/ISA/US, International Search Report and Written Opinion issued in corresponding PCT Application No. PCT/US16/29151 dated Oct. 11, 2016 (14 pages).
Numata et al., Expression and mutational analysis of amino acid residues involved in catalytic activity in a ribonuclease MC1 from the seeds of bitter gourd, Biosci Biotechnol Biochem 2000, vol. 64(3) p. 603-605.
NCBI_1BK7_A, chain A, Ribonuclease Mc1 From the Seeds of Bitter Gourd, NCBI, Accession No. 1BK7_A, Oct. 10, 2012 (online) [Retrieved Jun. 1, 2016 by WIPO ISA], http://www.ncbi.nlm/nih.gov/protein/5821838?report=genbank&log$=protalign&blast_rank=1&RID=RDVM3VA001R>PDF , 2 pages.
Rojo et al., Custavin, a new cytidine-specific ribonuclease accumulated in seeds of *Cucumis sativus* L. Planta, 1994, vol. 194(3), p. 328-338.
European Patent Office, Extended European Search Report issued in corresponding EP Application No. 16784068.5 dated Aug. 14, 2018 (10 pages).
Database UniProt [Online] EMBL; Jan. 7, 2015, Anonymous: Database accession No. IPI0002B4BE6 (2 pages).
Lesner, et al., Optimal conditions for expression and purification of recombinant U-specific MC1 ribonuclease, Aug. 2014 (1 page).
Venus, et al., Purification and characterization of cytidine-specific ribonuclease Cusativin, Nov. 4, 2014 (1 page).

* cited by examiner

*Primary Examiner* — Richard G Hutson
(74) *Attorney, Agent, or Firm* — Wood, Herron & Evans, LLP

(57) ABSTRACT

A recombinant ribonuclease is disclosed. The recombinant ribonuclease is produced by introducing a recombinant DNA sequence into a host; activating expression of the recombinant DNA sequence within the host to produce the recombinant ribonuclease; and isolating the recombinant ribonuclease from the host. Additionally, a method of analyzing an RNA sequence includes digesting the RNA with a first recombinant ribonuclease to give digestion products comprising nucleotides of the RNA sequence; and analyzing the digestion products using an analytical method to provide the identity of at least some of the nucleotides. The recombinant ribonuclease includes at least one of a uridine-specific recombinant RNase MC1 and a cytidine-specific recombinant RNase Cusativin.

1 Claim, 52 Drawing Sheets

Specification includes a Sequence Listing.

```
1.
  F    D    S    F    W    F    V    Q    Q    W    P    P    A    V    C    S    F    Q    K    S
 TTC  GAC  TCC  TTT  TGG  TTT  GTT  CAG  CAG  TGG  CCG  CCA  GCA  GTT  TGC  AGT  TTC  CAA  AAA  AGT
 TTT  GAT  AGC  TTC       TTC  GTG  CAA  CAA
           TCG                 GTC
           TCA                 GTA
           AGT
           TCT
21.
  G    S    C    P    G    S    G    L    R    T    F    T    I    H    G    L    W    P    Q    Q
 GGT  AGT  TGC  CCT  GGT  AGT  GGT  CTG  CGC  ACG  TTT  ACT  ATC  CAT  GGC  CTG  TGG  CCG  CAA  CAG
 GGA  AGC  TGT  CCG  GGA  AGC  GGA  TTA  CGT  ACC  TTC  ACC  ATT  CAC  GGT  TTA       CCC  CAG  CAA
 GGC  TCG       CCA  GGG  TCG  GGC  TTG  CGA  ACT       ACG  ATA       GGA  TTG       CCA
 GGG  TCA       CCC  GGC  TCA  GGG  CTT  CGG  ACA       ACA            GGG  CTT       CCT
      TCT            TCT            CTC  AGG                                CTC
      TCC            TCC            CTA  AGA                                CTA
41.
  S    G    T    S    L    T    N    C    P    G    S    P    F    D    I    T    K    I    S    H
 AGC  GGC  ACA  AGC  CTG  ACT  AAC  TGT  CCG  GGT  TCT  CCG  TTT  GAT  ATC  ACC  AAG  ATC  AGC  CAC
 TCG  GGG  ACT  TCG  TTA  ACC  AAT  TGC  CCT  GGC  AGC  CCC  TTC  GAC  ATT  ACG  AAA  ATT  TCG  CAT
 TCA  GGA  ACG  TCA  TTG  ACG            CCA  GGA  TCG  CCA            ATA  ACT       ATA  TCA
 AGT  GGT  ACC  AGT  CTT  ACA            CCC  GGG  AGT  CCT                 ACA            AGT
 TCT       TCT  CTC                                TCC                                     TCT
 TCC       TCC  CTA                                TCA                                     TCC

61.
  L    Q    S    Q    L    N    T    L    W    P    N    V    L    R    A    N    N    Q    Q    F
 CTG  CAG  AGC  CAG  CTC  AAT  ACC  CTG  TGG  CCG  AAC  GTG  CTG  CGT  GCC  AAT  AAC  CAA  CAG  TTC
 TTA  CAA  TCG  CAA  TTA  AAT  ACG  TTA  TGG  CCT  AAT  GTT  TTA  CGC  GCG  AAC  AAT  CAG  CAA  TTT
 TTG       TCA       TTG       ACT  TTG       CCA       GTC  TTG  CGA  GCA
 CTT       AGT       CTT       ACA  CTT       CCC       GTA  CTT  CGG  GCT
 CTC       TCT       CTC            CTC                      CTC  AGG
 CTA       TCC       CTA            CTA                      CTA  AGA
81.
  W    S    H    E    W    T    K    H    G    T    C    S    E    S    T    F    N    Q    A    A
 TGG  AGT  CAC  GAG  TGG  ACG  AAA  CAT  GGC  ACA  TGC  TCC  GAA  AGC  ACC  TTT  AAC  CAA  GCG  GCC
      AGC  CAT  GAA       ACC  AAG  CAC  GGT  ACG  TGT  TCT  GAG  TCG  ACG  TTC  AAT  CAG  GCC  GCG
           TCG            ACT            GGA  ACT            AGT       TCA  ACT            GCA  GCA
           TCT            ACA            GGG  ACA            AGC       AGT  ACA            GCT  GCT
           TCC                                               TCA       TCT
           TCA                                               TCG       TCC
101,
  Y    F    K    L    A    V    D    M    R    N    N    Y    D    I    I    G    A    L    R    P
 TAC  TTC  AAA  CTT  GCG  GTC  GAC  ATG  CGC  AAC  AAC  TAT  GAT  ATC  ATC  GGG  GCC  TTG  CGT  CCG
 TAT  TTC  AAG  CTG  GCC  GTT  GAT       CGT  AAT  AAT  TAC  GAC  ATT  ATT  GGT  GCG  TTA  CGC  CCT
           TTA  GCA  GTC            CGA                      ATA  ATA  GGA  GCA  CTG  CGA  CCA
           TTG  GCT  GTA            CGG                                GGG  GCT  CTT  CGG  CCC
           CTC                      AGG                                               CTC  AGG
           CTA                      AGA                                               CTA  AGA
```

Figure 1A

```
121.
    H   A   A   G   P   N   G   R   T   K   S   R   Q   A   I   K   G   F   L   K
    CAC GCA GCA GGC CCG AAC GGC CGT ACC AAA TCA CGT CAG GCC ATC AAA GGG TTT CTG AAA
    CAT GCG GCG GGT CCT AAT GGT CGC ACG AAG AGC CGC CAA GCG ATT AAG GGT TTC TTA AAG
        GCC GCC GGA CCA     GGA CGA ACT     TCG CGA     GCA ATA     GGA     TTG
        GCT GCT GGG CCC     GGG AGG ACA     AGT CGG     GCT         GGC     CTT
                                AGA         TCT AGG                         CTC
                                CGG         TCC AGA                         CTA

141.
    A   K   F   G   K   F   P   G   L   R   C   R   T   D   P   Q   T   K   V   S
    GCG AAA TTT GGT AAA TTT CCG GGC TTA CGT TGT CGT ACC GAT CCG CAA ACG AAA GTT AGC
    GCC AAG TTC GGC AAG TTC CCT GGT CTG CGC TGC CGC ACG GAC CCT CAG ACC AAG GTG TCG
    GCA     GGA         CCA GGA TTG CGA     CGA ACT     CCA     ACT         GTC TCA
    GCT     GGG         CCC GGG CTT CGG     CGG ACA     CCC     ACA         GTA AGT
                                CTC AGG     AGG                                 TCT
                                CTA AGA     AGA                                 TCC

161.
    Y   L   V   Q   V   V   A   C   F   A   Q   D   G   S   T   L   I   D   C   T
    TAT CTG GTT CAA GTC GTC GCA TGC TTC GCC CAG GAT GGT TCA ACC TTA ATT GAT TGT ACC
    TAC TTA GTG CAG GTG GTG GCG TGT TTT GCG CAA GAC GGC TCG ACG CTG ATC GAC TGC ACG
        TTG GTC     GTT GTT GCA     GCA         GGA AGC ACT TTG ATA         ACT
        CTT GTA     GTA GTA GCT     GCT         GGG AGT ACA CTT             ACA
        CTC                                         TCT     CTC
        CTA                                         TCC     CTA

181.
    R   D   T   C   G   A   N   F   I   F
    CGC GAC ACG TGT GGC GCC AAT TTC ATC TTT
    CGT GAT ACC TGC GGT GCG AAC TTT ATT TTC
    CGA     ACT     GGA GCA     ATA
    CGG     ACA     GGG GCT
    AGG
    AGA
```

Figure 1A (cont'd)

```
TTC GAC TCC TTT TGG TTT
GTT CAG CAG TGG CCG CCA
GCA GTT TGC AGT TTC CAA
AAA AGT GGT AGT TGC CCT
GGT AGT GGT CTG CGC ACG
TTT ACT ATC CAT GGC CTG
TGG CCG CAA CAG AGC GGC
ACA AGC CTG ACT AAC TGT
CCG GGT TCT CCG TTT GAT
ATC ACC AAG ATC AGC CAC
CTG CAG AGC CAG CTC AAT
ACC CTG TGG CCG AAC GTG
CTG CGT GCC AAT AAC CAA
CAG TTC TGG AGT CAC GAG
TGG ACG AAA CAT GGC ACA
TGC TCC GAA AGC ACC TTT
AAC CAA GCG GCC TAC TTC
AAA CTT GCG GTC GAC ATG
CGC AAC AAC TAT GAT ATC
ATC GGG GCC TTG CGT CCG
CAC GCA GCA GGC CCG AAC
GGC CGT ACC AAA TCA CGT
CAG GCC ATC AAA GGG TTT
CTG AAA GCG AAA TTT GGT
AAA TTT CCG GGC TTA CGT
TGT CGT ACC GAT CCG CAA
ACG AAA GTT AGC TAT CTG
GTT CAA GTC GTC GCA TGC
TTC GCC CAG GAT GGT TCA
ACC TTA ATT GAT TGT ACC
CGC GAC ACG TGT GGC GCC
AAT TTC ATC TTT
```

(SEQ ID NO. 2)

Figure 1B

```
1.
  M   E   K   T   K   S   V   D   V   V   F   F   V   F   V   L   T   I   L   F
ATG GAA AAG ACC AAA AGT GTC GAT GTG GTG TTT TTT GTA TTT GTC CTG ACT ATC CTG TTC
    GAG AAA ACG AAG AGC GTT GAC GTT GTT TTC TTC GTG TTC GTT TTA ACC ATT TTA TTG
            ACT     TCG GTG         GTC         GTC     GTG TTG ACG ATA TTG
            ACA     TCA GTA         GTA         GTT     GTA CTT ACA     CTT
                    TCT                                     CTC         CTC
                    TCC                                     CTA         CTA

21.
  P   I   V   K   S   Q   T   F   D   D   F   W   F   V   Q   Q   W   P   P   A
CCG ATC GTC AAG AGT CAG ACA TTT GAC GAT TTC TGG TTT GTT CAA CAA TGG CCT CCG GCG
CCT ATT GTG AAA AGC CAA ACC TTC GAT GAC TTT     TTC GTC CAG CAG     CCG CCT GCC
CCA ATA GTT     TCG     ACG                         GTC             CCC CCA GCA
CCC     GTA     TCA     ACT                         GTA             CCA CCC GCT
                TCT
                TCC

41.
  V   C   T   L   Q   S   G   R   C   V   G   R   G   T   R   S   F   T   I   H
GTT TGT ACG TTA CAG TCT GGC CGC TGT GTT GGT CGT GGA ACT CGC TCA TTT ACT ATT CAT
GTG TGT ACC TTG CAA TCG GGT CGT TGC GTG GGC CGC GGT ACC CGT AGC TTC ACG ATC CAC
GTC     ACT CTT     AGC GGA CGA     GTC GGG CGA GGG ACG CGA TCG     ACC ATA
GTA     ACA CTC     AGT GGG CGG     GTA GGA CGG GGC ACA CGG AGT     ACA
                    CTG     TCC     AGG         AGG         AGG TCT
                    CTA     TCA     AGA         AGA         AGA TCC

61.
  G   L   W   P   Q   K   G   G   R   S   V   T   N   C   T   G   N   Q   F   D
GGC CTG TGG CCA CAG AAA GGC GGC CGT AGT GTT ACG AAC TGT ACT GGT AAC CAG TTT GAT
GGT TTA     CCC CAA AAG GGT GGT CGC AGC GTC ACC AAT TGC ACC GGC AAT CAA TTC GAC
GGA TTG     CCT         GGA GGA CGA TCG GTA ACT         ACG GGA
GGG CTT     CCG         GGG GGG CGG TCA GTG ACA         ACA GGG
    CTC                             AGG TCT
    CTA                             AGA TCC

81.
  F   T   K   I   A   H   L   E   N   D   L   N   V   V   W   P   N   V   V   T
TTT ACG AAA ATT GCA CAC CTG GAA AAC GAT TTG AAC GTT GTA TGG CCC AAT GTG GTC ACG
TTC ACC AAG ATC GCG CAT TTA GAG AAT GAC CTG AAT GTG GTG     CCT AAC GTT GTG ACC
    ACT     ATA GCC     TTG             TTA     GTC GTC     CCG     GTC GTT ACT
    ACA     ACT GCT     CTT             CTT     GTA GTT     CCA     GTA GTA ACA
                        CTC             CTC
                        CTA             CTA

101.
  G   N   N   K   F   F   W   G   H   E   W   N   K   H   G   I   C   S   E   S
GGC AAT AAC AAA TTC TTT TGG GGG CAT GAG TGG AAT AAG CAC GGC ATC TGT TCA GAA TCC
GGT AAC AAT AAG TTT TTC     GGT CAC GAA     AAC AAA CAT GGT ATT TGC AGC GAG AGC
GGG                         GGA                         GGA ATA     TCG     TCG
GGA                         GGG                         GGG         AGT     TCA
                                                                    TCT     AGT
                                                                    TCC     TCT
```

Figure 2A

```
121.
  K   F   D   E   A   K   Y   F   Q   T   A   I   N   M   R   H   G   I   D   L
  AAA TTT GAT GAA GCC AAA TAT TTC CAG ACC GCG ATT AAC ATG CGC CAT GGC ATC GAT CTG
  AAG TTC GAC GAG GCG AAG TAC TTT CAA ACG GCC ATC AAT     CGT CAC GGT ATT GAC TTA
                  GCA                     ACT GCA ATA     CGA     GGA ATA     TTG
                  GCT                     ACA GCT         CGG         GGG     CTT
                                                          AGG                 CTC
                                                          AGA                 CTA
141.
  L   S   V   L   R   T   G   G   V   G   P   N   G   A   S   K   A   K   Q   R
  TTG AGC GTC CTC CGT ACC GGC GGT GTT GGT CCA AAT GGC GCT AGC AAA GCC AAA CAA CGC
  TTA TCG GTG TTA CGC ACG GGT GGC GTG GGC CCT AAC GGT GCG TCG AAG GCG AAG CAG CGT
  CTG TCA GTT TTG CGA ACT GGA GGA GTC GGA CCG     GGA GCA TCA     GCA     CGA
  CTT AGT GTA CTT CGG ACA GGG GGG GTA GGG CCC     GGG GCT AGT     GCT     CGG
  CTC TCT     CTG AGG                                         TCT             AGA
  CTA TCC     CTA AGA                                         TCC             AGG
161.
  V   E   T   A   I   S   S   H   F   G   K   D   P   I   L   R   C   K   K   A
  GTG GAA ACC GCC ATC TCC TCC CAC TTT GGT AAG GAT CCG ATT CTG CGG TGC AAA AAG GCG
  GTT GAG ACG GCG ATT TCT TCT CAT TTC GGC AAA GAC CCT ATC TTA CGC TGT AAG AAG GCC
  GTC     ACT GCA ATA AGT AGT         GGA         CCA ATA TTG CGT             GCA
  GTA     ACA GCT     TCA TCA         GGG         CCC     CTT CGA             GCT
                      TCG TCG                             CTC AGG
                      AGC AGC                             CTA AGA
181.
  S   N   G   Q   V   L   L   T   E   I   V   M   C   F   D   D   D   G   V   T
  TCG AAC GGC CAA GTG CTG CTG ACG GAG ATT GTG ATG TGC TTT GAT GAC GAC GGC GTC ACC
  TCA AAT GGT CAG GTT TTA TTA ACC GAA ATC GTT     TGT TTC GAC GAT GAT GGT GTG ACG
  AGT     GGA     GTC TTG TTG ACT     ATA GTC                         GGA GTT ACT
  TCT     GGG     GTA CTT CTT ACA         GTA                         GGG GTA ACA
  TCC                 CTC CTC
  AGC                 CTA CTA
201.
  L   I   N   C   N   K   A   R   S   N   C   A   G   S   F   I   F
  CTG ATC AAT TGT AAT AAG GCG CGC TCC AAT TGC GCA GGC TCA TTT ATT TTT
  TTA ATT AAC TGC AAC AAA GCC CGT TCG AAC TGT GCG GGT AGC TTC ATC TTC
  TTG ATA             GCA CGA TCA         GCC GGA TCG         ATA
  CTT                 GCT CGG TCT         GCT GGG AGT
  CTC                     AGG AGT                 TCT
  CTA                     AGA AGC                 TCC
```

Figure 2A (cont'd)

```
ATG GAA AAA ACA AAG AGT GTC GAT GTT GTG TTC TTC GTG TTT
GTC TTA ACC ATT TTG TTT CCT ATC GTT AAA TCG CAA ACT TTC
GAT GAT TTT TGG TTT GTT CAG CAA TGG CCA CCA GCT GTT TGT
ACT TTA CAA TCA GGA CGA TGT GTA GGA CGA GGG ACT CGA TCC
TTC ACA ATT CAT GGT TTG TGG CCT CAA AAG GGA GGA CGT TCT
GTG ACT AAT TGT ACT GGC AAT CAA TTT GAT TTC ACT AAG ATT
GCA CAT TTA GAA AAC GAT CTA AAC GTA GTT TGG CCG AAT GTG
GTG ACG GGA AAC AAC AAA TTC TTT TGG GGT CAT GAA TGG AAC
AAA CAT GGG ATT TGC TCA GAG AGC AAG TTT GAC GAA GCG AAG
TAC TTC CAA ACA GCG ATA AAC ATG AGG CAC GGT ATC GAC CTT
CTT AGT GTG CTG AGA ACT GGT GGA GTA GGA CCA AAT GGA GCC
TCC AAG GCA AAG CAA AGA GTC GAA ACC GCG ATT TCA TCC CAT
TTT GGA AAA GAT CCA ATT CTT CGA TGT AAA AAA GCA TCA AAC
GGC CAA GTC TTA TTG ACG GAG ATT GTG ATG TGC TTC GAT GAC
GAT GGT GTC ACC CTT ATA AAC TGT AAC AAA GCA AGA TCC AAT
TGT GCT GGG AGC TTT ATT TTT
```

(SEQ ID NO. 3)

Figure 2B

```
ATG GAA AAG ACC AAA AGT GTC GAT GTG GTG TTT TTT GTA TTT
GTC CTG ACT ATC CTG TTC CCG ATC GTC AAG AGT CAG ACA TTT
GAC GAT TTC TGG TTT GTT CAA CAA TGG CCT CCG GCG GTT TGT
ACG TTA CAG TCT GGC CGC TGT GTT GGT CGT GGA ACT CGC TCA
TTT ACT ATT CAT GGC CTG TGG CCA CAG AAA GGC GGC CGT AGT
GTT ACG AAC TGT ACT GGT AAC CAG TTT GAT TTT ACG AAA ATT
GCA CAC CTG GAA AAC GAT TTG AAC GTT GTA TGG CCC AAT GTG
GTC ACG GGC AAT AAC AAA TTC TTT TGG GGG CAT GAG TGG AAT
AAG CAC GGC ATC TGT TCA GAA TCC AAA TTT GAT GAA GCC AAA
TAT TTC CAG ACC GCG ATT AAC ATG CGC CAT GGC ATC GAT CTG
TTG AGC GTC CTC CGT ACC GGC GGT GTT GGT CCA AAT GGC GCT
AGC AAA GCC AAA CAA CGC GTG GAA ACC GCC ATC TCC TCC CAC
TTT GGT AAG GAT CCG ATT CTG CGG TGC AAA AAG GCG TCG AAC
GGC CAA GTG CTG CTG ACG GAG ATT GTG ATG TGC TTT GAT GAC
GAC GGC GTC ACC CTG ATC AAT TGT AAT AAG GCG CGC TCC AAT
TGC GCA GGC TCA TTT ATT TTT
```

(SEQ ID NO. 4)

Figure 2C

```
SEQ ID NO. 3    1 ATGGAAAAAACAAAGAGTGTCGATGTTGTGTTCTTCGTGTTTGTCTTAACCATTTTGTTT   60
                  ||||||||  || || |||||||||||  |||||  || ||  ||||||  | || ||     ||||
SEQ ID NO. 4    1 ATGGAAAAGACCAAAAGTGTCGATGTGGTGTTTTTTGTATTTGTCCTGACTATCCTGTTC   60

SEQ ID NO. 3   61 CCTATCGTTAAATCGCAAACTTTCGATGATTTTGGTTTGTTCAGCAATGGCCACCAGCT  120
                  ||  ||||||  ||       ||  ||  ||  ||  || |||||  ||||||||||||  ||||||||  ||  ||
SEQ ID NO. 4   61 CCGATCGTCAAGAGTCAGACATTTGACGATTTCTGGTTTGTTCAACAATGGCCTCCGGCG  120

SEQ ID NO. 3  121 GTTTGTACTTTACAATCAGGACGATGTGTAGGACGAGGGACTCGATCCTTCACAATTCAT  180
                  ||||||||  |||||  || ||  ||  ||||||  || ||  || || ||||||  || ||  ||  ||||||
SEQ ID NO. 4  121 GTTTGTACGTTACAGTCTGGCCGCTGTGTTGGTCGTGGAACTCGCTCATTTACTATTCAT  180

SEQ ID NO. 3  181 GGTTTGTGGCCTCAAAAGGGAGGACGTTCTGTGACTAATTGTACTGGCAATCAATTTGAT  240
                  ||  |||||||||  || ||  || || |||    |||  || ||  |||||||||  || || ||||||
SEQ ID NO. 4  181 GGCCTGTGGCCACAGAAAGGCGGCCGTAGTGTTACGAACTGTACTGGTAACCAGTTTGAT  240

SEQ ID NO. 3  241 TTCACTAAGATTGCACATTTAGAAAACGATCTAAACGTAGTTTGGCCGAATGTGGTGACG  300
                  || || || ||||||||  |  ||||||||| | |||||  ||  |||||  |||||||||  |||
SEQ ID NO. 4  241 TTTACGAAAATTGCACACCTGGAAAACGATTTGAACGTTGTATGGCCCAATGTGGTCACG  300

SEQ ID NO. 3  301 GGAAACAACAAATTCTTTTGGGGTCATGAATGGAACAAACATGGGATTTGCTCAGAGAGC  360
                  ||  ||  ||||||||||||||||||| |||||  |||||  || || ||  ||  || ||  ||||||  |
SEQ ID NO. 4  301 GGCAATAACAAATTCTTTTGGGGGCATGAGTGGAATAAGCACGGCATCTGTTCAGAATCC  360

SEQ ID NO. 3  361 AAGTTTGACGAAGCGAAGTACTTCCAAACAGCGATAAACATGAGGCACGGTATCGACCTT  420
                  || ||||||  ||||| || || ||||||  || |||||  |||||| | || || ||||||  ||
SEQ ID NO. 4  361 AAATTTGATGAAGCCAAATATTTCCAGACCGCGATTAACATGCGCCATGGCATCGATCTG  420

SEQ ID NO. 3  421 CTTAGTGTGCTGAGAACTGGTGGAGTAGGACCAAATGGAGCCTCCAAGGCAAAGCAAAGA  480
                  |  || || ||   | || || || || || |||||||| ||     ||| || || ||| |
SEQ ID NO. 4  421 TTGAGCGTCCTCCGTACCGGCGGTGTTGGTCCAAATGGCGCTAGCAAAGCCAAACAACGC  480

SEQ ID NO. 3  481 GTCGAAACCGCGATTTCATCCCATTTTGGAAAAGATCCAATTCTTCGATGTAAAAAAGCA  540
                  || ||||||||| ||  || ||||| |||||  || |||||  |||||| ||  || ||||| ||
SEQ ID NO. 4  481 GTGGAAACCGCCATCTCCTCCCACTTTGGTAAGGATCCGATTCTGCGGTGCAAAAAGGCG  540

SEQ ID NO. 3  541 TCAAACGGCCAAGTCTTATTGACGGAGATTGTGATGTGCTTCGATGACGATGGTGTCACC  600
                  || ||||||||||||  |  ||  |||||||||||||||||||||||  |||||||| || ||||||
SEQ ID NO. 4  541 TCGAACGGCCAAGTGCTGCTGACGGAGATTGTGATGTGCTTTGATGACGACGGCGTCACC  600

SEQ ID NO. 3  601 CTTATAAACTGTAACAAAGCAAGATCCAATTGTGCTGGGAGCTTTATTTTT  651
                  ||  ||  ||  |||||| ||  ||  |   ||||||||||  || ||        ||||||||
SEQ ID NO. 4  601 CTGATCAATTGTAATAAGGCGCGCTCCAATTGCGCAGGCTCATTTATTTTT  651
```

Figure 2D

SEQUENCE LISTING

<160> NUMBER OF SEQ ID NOS: 27

<210> SEQ ID NO 1
<211> LENGTH: 190
<212> TYPE: PRT
<213> ORGANISM: Momordica charantia

<400> SEQUENCE: 1

```
Phe Asp Ser Phe Trp Phe Val Gln Gln Trp Pro Pro Ala Val Cys Ser
1               5                   10                  15

Phe Gln Lys Ser Gly Ser Cys Pro Gly Ser Gly Leu Arg Thr Phe Thr
            20                  25                  30

Ile His Gly Leu Trp Pro Gln Gln Ser Gly Thr Ser Leu Thr Asn Cys
        35                  40                  45

Pro Gly Ser Pro Phe Asp Ile Thr Lys Ile Ser His Leu Gln Ser Gln
    50                  55                  60

Leu Asn Thr Leu Trp Pro Asn Val Leu Arg Ala Asn Asn Gln Gln Phe
65                  70                  75                  80

Trp Ser His Glu Trp Thr Lys His Gly Thr Cys Ser Glu Ser Thr Phe
                85                  90                  95

Asn Gln Ala Ala Tyr Phe Lys Leu Ala Val Asp Met Arg Asn Asn Tyr
            100                 105                 110

Asp Ile Ile Gly Ala Leu Arg Pro His Ala Ala Gly Pro Asn Gly Arg
        115                 120                 125

Thr Lys Ser Arg Gln Ala Ile Lys Gly Phe Leu Lys Ala Lys Phe Gly
    130                 135                 140

Lys Phe Pro Gly Leu Arg Cys Arg Thr Asp Pro Gln Thr Lys Val Ser
145                 150                 155                 160

Tyr Leu Val Gln Val Val Ala Cys Phe Ala Gln Asp Gly Ser Thr Leu
                165                 170                 175

Ile Asp Cys Thr Arg Asp Thr Cys Gly Ala Asn Phe Ile Phe
            180                 185                 190

<210> SEQ ID NO 2
<211> LENGTH: 570
<212> TYPE: DNA
<213> ORGANISM: Artificial Sequence
<220> FEATURE:
<223> OTHER INFORMATION: Recombinant nucleotide-specific ribonuclease
      MC1

<400> SEQUENCE: 2
ttcgactcct tttggtttgt tcagcagtgg ccgccagcag tttgcagttt ccaaaaaagt    60
ggtagttgcc ctggtagtgg tctgcgcacg tttactatcc atggcctgtg ccgcaacag   120 agcggcacaa gcctgactaa ctgtccgggt tctccgtttg atatcaccaa gatcagccac   180
ctgcagagcc agctcaatac cctgtggccg aacgtgctgc gtgccaataa ccaacagttc   240
tggagtcacg agtggacgaa acatggcaca tgctccgaaa gcacctttaa ccaagcggcc   300
tacttcaaac ttgcggtcga catgcgcaac aactatgata tcatcggggc cttgcgtccg   360
cacgcagcag gcccgaacgg ccgtaccaaa tcacgtcagg ccatcaaagg gtttctgaaa   420
gcgaaatttg gtaaatttcc gggcttacgt tgtcgtaccg atccgcaaac gaaagttagc   480
tatctggttc aagtcgtcgc atgcttcgcc caggatggtt caaccttaat tgattgtacc   540
cgcgacacgt gtggcgccaa tttcatcttt                                     570

<210> SEQ ID NO 3
<211> LENGTH: 651
<212> TYPE: DNA
<213> ORGANISM: Cucumis sativus

<400> SEQUENCE: 3
atggaaaaaa caaagagtgt cgatgttgtg ttcttcgtgt tgtcttaac cattttgttt     60 cctatcgtta aatcgcaaac ttcgatgat ttttggtttg tcagcaatg gccaccagct    120
```

-continued

```
gtttgtactt tacaatcagg acgatgtgta ggacgaggga ctcgatcctt cacaattcat      180
ggtttgtggc tcaaaaggg aggacgttct gtgactaatt gtactggcaa tcaatttgat      240
ttcactaaga ttgcacattt agaaaacgat ctaaacgtag tttggccgaa tgtggtgacg      300
ggaaacaaca aattcttttg gggtcatgaa tggaacaaac atgggatttg ctcagagagc      360
aagtttgacg aagcgaagta cttccaaaca gcgataaaca tgaggcacgg tatcgacctt      420
cttagtgtgc tgagaactgg tggagtagga ccaaatggag cctccaaggc aaagcaaaga      480
gtcgaaaccg cgatttcatc ccatttttgga aaagatccaa ttcttcgatg taaaaaagca      540
tcaaacggcc aagtcttatt gacggagatt gtgatgtgct tcgatgacga tggtgtcacc      600
cttataaact gtaacaaagc aagatccaat tgtgctggga gctttatttt t              651
```

<210> SEQ ID NO 4
<211> LENGTH: 651
<212> TYPE: DNA
<213> ORGANISM: Artificial Sequence
<220> FEATURE:
<223> OTHER INFORMATION: Recombinant nucleotide-specific ribonuclease Cusativin

<400> SEQUENCE: 4

```
atggaaaaga ccaaaagtgt cgatgtggtg ttttttgtat ttgtcctgac tatcctgttc      60
ccgatcgtca agagtcagac atttgacgat ttctggtttg ttcaacaatg gcctccggcg      120
gtttgtacgt tacagtctgg ccgctgtgtt ggtcgtggaa ctcgctcatt tactattcat      180
ggcctgtggc cacagaaagg cggccgtagt gttacgaact gtactggtaa ccagtttgat      240
tttacgaaaa ttgcacacct ggaaaacgat ttgaacgttg tatggcccaa tgtggtcacg      300
ggcaataaca aattcttttg ggggcatgag tggaataagc acggcatctg ttcagaatcc      360
aaatttgatg aagccaaata tttccagacc gcgattaaca tgcgccatgg catcgatctg      420
ttgagcgtcc tccgtaccgg cggtgttggt ccaaatggcg ctagcaaagc caaacaacgc      480
gtggaaaccg ccatctcctc ccactttggt aaggatccga ttctgcggtg caaaaaggcg      540
tcgaacggcc aagtgctgct gacggagatt gtgatgtgct ttgatgacga cggcgtcacc      600
ctgatcaatt gtaataaggc cgctccaat tgcgcaggct catttatttt t               651
```

<210> SEQ ID NO 5
<211> LENGTH: 217
<212> TYPE: PRT
<213> ORGANISM: Cucumis sativus

<400> SEQUENCE: 5

Met Glu Lys Thr Lys Ser Val Asp Val Val Phe Phe Val Phe Val Leu
1               5                   10                  15

Thr Ile Leu Phe Pro Ile Val Lys Ser Gln Thr Phe Asp Asp Phe Trp
            20                  25                  30

Phe Val Gln Gln Trp Pro Pro Ala Val Cys Thr Leu Gln Ser Gly Arg
        35                  40                  45

Cys Val Gly Arg Gly Thr Arg Ser Phe Thr Ile His Gly Leu Trp Pro
    50                  55                  60

Gln Lys Gly Gly Arg Ser Val Thr Asn Cys Thr Gly Asn Gln Phe Asp
65                  70                  75                  80

Phe Thr Lys Ile Ala His Leu Glu Asn Asp Leu Asn Val Val Trp Pro
                85                  90                  95

Asn Val Val Thr Gly Asn Asn Lys Phe Phe Trp Gly His Glu Trp Asn
            100                 105                 110

| Lys | His | Gly | Ile | Cys | Ser | Glu | Ser | Lys | Phe | Asp | Glu | Ala | Lys | Tyr | Phe |
|---|---|---|---|---|---|---|---|---|---|---|---|---|---|---|---|
| | | 115 | | | | 120 | | | | 125 | | | | | |

| Gln | Thr | Ala | Ile | Asn | Met | Arg | His | Gly | Ile | Asp | Leu | Leu | Ser | Val | Leu |
|---|---|---|---|---|---|---|---|---|---|---|---|---|---|---|---|
| 130 | | | | | 135 | | | | | 140 | | | | | |

| Arg | Thr | Gly | Gly | Val | Gly | Pro | Asn | Gly | Ala | Ser | Lys | Ala | Lys | Gln | Arg |
|---|---|---|---|---|---|---|---|---|---|---|---|---|---|---|---|
| 145 | | | | 150 | | | | | 155 | | | | | 160 | |

| Val | Glu | Thr | Ala | Ile | Ser | Ser | His | Phe | Gly | Lys | Asp | Pro | Ile | Leu | Arg |
|---|---|---|---|---|---|---|---|---|---|---|---|---|---|---|---|
| | | | | 165 | | | | | 170 | | | | 175 | | |

| Cys | Lys | Lys | Ala | Ser | Asn | Gly | Gln | Val | Leu | Leu | Thr | Glu | Ile | Val | Met |
|---|---|---|---|---|---|---|---|---|---|---|---|---|---|---|---|
| | | 180 | | | | | 185 | | | | 190 | | | | |

| Cys | Phe | Asp | Asp | Asp | Gly | Val | Thr | Leu | Ile | Asn | Cys | Asn | Lys | Ala | Arg |
|---|---|---|---|---|---|---|---|---|---|---|---|---|---|---|---|
| | | 195 | | | | | 200 | | | | 205 | | | | |

| Ser | Asn | Cys | Ala | Gly | Ser | Phe | Ile | Phe |
|---|---|---|---|---|---|---|---|---|
| 210 | | | | | 215 | | | |

<210> SEQ ID NO 6
<211> LENGTH: 17
<212> TYPE: RNA
<213> ORGANISM: Escherichia coli
<220> FEATURE:
<221> NAME/KEY: misc_feature
<222> LOCATION: (1)..(1)
<223> OTHER INFORMATION: s4u
<220> FEATURE:
<221> NAME/KEY: misc_feature
<222> LOCATION: (10)..(10)
<223> OTHER INFORMATION: gm
<220> FEATURE:
<221> NAME/KEY: misc_feature
<222> LOCATION: (12)..(12)
<223> OTHER INFORMATION: gm

<400> SEQUENCE: 6
nucccgagcn gccaaag                                                    17

<210> SEQ ID NO 7
<211> LENGTH: 85
<212> TYPE: RNA
<213> ORGANISM: Escherichia coli
<220> FEATURE:
<221> NAME/KEY: misc_feature
<222> LOCATION: (8)..(8)
<223> OTHER INFORMATION: s4u
<220> FEATURE:
<221> NAME/KEY: misc_feature
<222> LOCATION: (17)..(17)
<223> OTHER INFORMATION: gm
<220> FEATURE:
<221> NAME/KEY: misc_feature
<222> LOCATION: (35)..(35)
<223> OTHER INFORMATION: q
<220> FEATURE:
<221> NAME/KEY: misc_feature
<222> LOCATION: (38)..(38)
<223> OTHER INFORMATION: ms2i6a
<220> FEATURE:
<221> NAME/KEY: misc_feature
<222> LOCATION: (40)..(40)
<223> OTHER INFORMATION: psi
<220> FEATURE:
<221> NAME/KEY: misc_feature
<222> LOCATION: (63)..(63)
<223> OTHER INFORMATION: m5u
<220> FEATURE:
<221> NAME/KEY: misc_feature
<222> LOCATION: (64)..(64)
<223> OTHER INFORMATION: psi

<400> SEQUENCE: 7

```
ggugggnuc ccgagcngcc aaagggagca gacunuanan cugccgucau cgacuucgaa      60
ggnncgaauc cuuccccac cacca                                            85
```

<210> SEQ ID NO 8
<211> LENGTH: 21
<212> TYPE: RNA
<213> ORGANISM: Escherichia coli
<220> FEATURE:
<221> NAME/KEY: misc_feature
<222> LOCATION: (2)..(2)
<223> OTHER INFORMATION: q
<220> FEATURE:
<221> NAME/KEY: misc_feature
<222> LOCATION: (5)..(5)
<223> OTHER INFORMATION: ms2i6a
<220> FEATURE:
<221> NAME/KEY: misc_feature
<222> LOCATION: (7)..(7)
<223> OTHER INFORMATION: psi

<400> SEQUENCE: 8

```
unuanancug ccgucaucga c                                               21
```

<210> SEQ ID NO 9
<211> LENGTH: 13
<212> TYPE: RNA
<213> ORGANISM: Escherichia coli

<400> SEQUENCE: 9

```
uccccccacca cca                                                       13
```

<210> SEQ ID NO 10
<211> LENGTH: 12
<212> TYPE: RNA
<213> ORGANISM: Escherichia coli
<220> FEATURE:
<221> NAME/KEY: misc_feature
<222> LOCATION: (3)..(3)
<223> OTHER INFORMATION: q
<220> FEATURE:
<221> NAME/KEY: misc_feature
<222> LOCATION: (4)..(4)
<223> OTHER INFORMATION: q
<220> FEATURE:
<221> NAME/KEY: misc_feature
<222> LOCATION: (7)..(7)
<223> OTHER INFORMATION: ms2i6a
<220> FEATURE:
<221> NAME/KEY: misc_feature
<222> LOCATION: (9)..(9)
<223> OTHER INFORMATION: psi

<400> SEQUENCE: 10

```
acunuananc ug                                                         12
```

<210> SEQ ID NO 11
<211> LENGTH: 19
<212> TYPE: RNA
<213> ORGANISM: Escherichia coli

<400> SEQUENCE: 11

```
aauccuuccc ccaccacca                                                  19
```

<210> SEQ ID NO 12
<211> LENGTH: 11
<212> TYPE: RNA
<213> ORGANISM: Escherichia coli

```
<400> SEQUENCE: 12
uaacuauaac g                                                    11

<210> SEQ ID NO 13
<211> LENGTH: 14
<212> TYPE: RNA
<213> ORGANISM: Escherichia coli

<400> SEQUENCE: 13
aucaccuccu uucu                                                 14

<210> SEQ ID NO 14
<211> LENGTH: 12
<212> TYPE: RNA
<213> ORGANISM: Escherichia coli
<220> FEATURE:
<221> NAME/KEY: misc_feature
<222> LOCATION: (8)..(8)
<223> OTHER INFORMATION: s4u

<400> SEQUENCE: 14 ggugggnuc cc                                                    12

<210> SEQ ID NO 15
<211> LENGTH: 14
<212> TYPE: RNA
<213> ORGANISM: Escherichia coli

<400> SEQUENCE: 15 uuccccccacc acca                                                14

<210> SEQ ID NO 16
<211> LENGTH: 22
<212> TYPE: PRT
<213> ORGANISM: Cucumis sativus

<400> SEQUENCE: 16

Ser Phe Thr Ile His Gly Leu Trp Pro Gln Lys Ser Phe Thr Ile His
1               5                   10                  15

Gly Leu Trp Pro Asn Lys
            20

<210> SEQ ID NO 17
<211> LENGTH: 18
<212> TYPE: PRT
<213> ORGANISM: Cucumis sativus

<400> SEQUENCE: 17

Tyr Phe Gln Thr Ala Ile Asn Met Arg Tyr Phe Gln Thr Ala Ile Asn
1               5                   10                  15

Met Arg

<210> SEQ ID NO 18
<211> LENGTH: 10
<212> TYPE: PRT
<213> ORGANISM: Cucumis sativus

<400> SEQUENCE: 18

His Gly Ile Asp Leu Leu Ser Val Leu Arg
1               5                   10

<210> SEQ ID NO 19
<211> LENGTH: 9
```

```
<212> TYPE: PRT
<213> ORGANISM: Cucumis sativus
<220> FEATURE:
<221> NAME/KEY: UNSURE
<222> LOCATION: (3)..(3)
<220> FEATURE:
<221> NAME/KEY: UNSURE
<222> LOCATION: (7)..(7)

<400> SEQUENCE: 19

Pro Pro Xaa Gly His Glu Xaa Asn Lys
1               5

<210> SEQ ID NO 20
<211> LENGTH: 21
<212> TYPE: PRT
<213> ORGANISM: Cucumis sativus

<400> SEQUENCE: 20

Ile Ala His Leu Glu Asn Asp Leu Asn Val Val Trp Pro Asn Val Val
1               5                   10                  15

Thr Gly Asn Asn Lys
            20

<210> SEQ ID NO 21
<211> LENGTH: 4
<212> TYPE: PRT
<213> ORGANISM: Cucumis sativus

<400> SEQUENCE: 21

Tyr Val Gly Arg
1

<210> SEQ ID NO 22
<211> LENGTH: 22
<212> TYPE: PRT
<213> ORGANISM: Cucumis sativus
<220> FEATURE:
<221> NAME/KEY: UNSURE
<222> LOCATION: (14)..(14)
<220> FEATURE:
<221> NAME/KEY: UNSURE
<222> LOCATION: (19)..(19)
<220> FEATURE:
<221> NAME/KEY: UNSURE
<222> LOCATION: (20)..(20)

<400> SEQUENCE: 22

Ala Ser Asn Gly Gln Val Leu Leu Thr Glu Ile Val Met Xaa Phe Asp
1               5                   10                  15

Asp Asp Xaa Xaa Thr Leu
            20

<210> SEQ ID NO 23
<211> LENGTH: 33
<212> TYPE: DNA
<213> ORGANISM: Unknown
<220> FEATURE:
<223> OTHER INFORMATION: Prim_transcript

<400> SEQUENCE: 23
atggaaaaat ggaaaagacc aaaagtgtcg atg                           33

<210> SEQ ID NO 24
<211> LENGTH: 26
<212> TYPE: DNA
<213> ORGANISM: Unknown
```

```
<220> FEATURE:
<223> OTHER INFORMATION: Prim_transcript

<400> SEQUENCE: 24
aaaaataaat gagcctgcgc aattgg                                              26

<210> SEQ ID NO 25
<211> LENGTH: 59
<212> TYPE: RNA
<213> ORGANISM: Escherichia coli
<220> FEATURE:
<221> NAME/KEY: misc_feature
<222> LOCATION: (9)..(9)
<223> OTHER INFORMATION: q
<220> FEATURE:
<221> NAME/KEY: misc_feature
<222> LOCATION: (9)..(9)
<223> OTHER INFORMATION: q
<220> FEATURE:
<221> NAME/KEY: misc_feature
<222> LOCATION: (12)..(12)
<223> OTHER INFORMATION: ms2i6a
<220> FEATURE:
<221> NAME/KEY: misc_feature
<222> LOCATION: (14)..(14)
<223> OTHER INFORMATION: psi
<220> FEATURE:
<221> NAME/KEY: misc_feature
<222> LOCATION: (37)..(37)
<223> OTHER INFORMATION: m5u
<220> FEATURE:
<221> NAME/KEY: misc_feature
<222> LOCATION: (38)..(38)
<223> OTHER INFORMATION: psi

<400> SEQUENCE: 25
agcagacunu anancugccg ucaucgacuu cgaaggnncg aauccuuccc ccaccacca          59

<210> SEQ ID NO 26
<211> LENGTH: 16
<212> TYPE: RNA
<213> ORGANISM: Escherichia coli
<220> FEATURE:
<221> NAME/KEY: misc_feature
<222> LOCATION: (8)..(8)
<223> OTHER INFORMATION: m5u
<220> FEATURE:
<221> NAME/KEY: misc_feature
<222> LOCATION: (9)..(9)
<223> OTHER INFORMATION: psi

<400> SEQUENCE: 26
ucgaaggnnc gaaucc                                                         16

<210> SEQ ID NO 27
<211> LENGTH: 13
<212> TYPE: RNA
<213> ORGANISM: Escherichia coli

<400> SEQUENCE: 27 uccccccacca cca                                                           13
```

RECOMBINANT NUCLEOSIDE-SPECIFIC RIBONUCLEASE AND METHOD OF PRODUCING AND USING SAME

CROSS-REFERENCE TO RELATED APPLICATIONS

This application is the U.S. National Phase Application of PCT Application No. PCT/US2016/029151, filed on Apr. 25, 2016, and is also related and claims priority to U.S. Provisional Patent Application Ser. No. 62/151,546, filed on Apr. 23, 2015, and U.S. Provisional Patent Application Ser. No. 62/151,640, also filed on Apr. 23, 2015, the entire contents of which are herein incorporated by reference.

STATEMENT REGARDING FEDERALLY SPONSORED RESEARCH OR DEVELOPMENT

This invention was made with government support under Grant No. CHE-1156449 awarded by the National Science Foundation and under Grant No. GM058843 awarded by the National Institutes of Health. The U.S. Government may have certain rights in this invention.

REFERENCE TO ONE OR MORE SEQUENCE LISTINGS

The accompanying sequence listings, which are incorporated in and constitute a part of this specification, illustrate embodiments of the invention and, together with a general description of the invention given above and the detailed description given below, serve to explain the principles of the invention.

FIELD

The present invention is generally related to the field of recombinant ribonucleases, and more particularly, to methods of analyzing an RNA sequence using a recombinant ribonuclease.

BACKGROUND

Nucleoside-specific ribonucleases (hereinafter "RNases") are important tools for locating the more than 120 modified nucleosides that may be found in an RNA sequence by the process generally referred to as RNA modification mapping. RNA modifications may be associated with a variety of human diseases through both structural and functional roles. Identification and location mapping of nucleoside modifications within the overall RNA sequence is important for determining the biological roles of nucleoside modifications. Traditionally, RNA-sequencing technologies primarily relied on polymerization-dependent copying of RNA into deoxyribonucleotides through Watson-Crick base pairing. However, this copying leads to a loss of modification information of the original RNA sequence.

Mass spectrometry (hereinafter "MS") can directly measure the mass shift associated with RNA modifications. One RNA mapping approach involves hydrolysis of a target RNA to yield nucleosides. Then, MS is used to create a census of nucleoside modifications and nucleoside-specific RNase digestion of the target RNA is used to identify modification placement. Knowledge of the compositional value of one nucleoside residue imposes a constraint on the number of possible base compositions for a given mass value. Thus, to simplify the MS analysis of RNase digestion products, much effort is expended to determine the compositional value of at least one nucleoside residue. In practice, base-specific RNase digestion of RNAs followed by separation and MS using ion-pairing, reverse phase liquid chromatography, or IP-RP-LC-MS, and collision-induced dissociation tandem mass spectrometry, or CID-MS/MS, allows one to map modified nucleosides onto the original RNA sequence.

Few nucleoside-specific or nucleoside-selective RNases are commercially available. Guanosine-specific RNase T1 and pyrimidine-selective RNase A are both commercially available and compatible with MS-based RNA modification mapping. Purine-selective RNase U2 is also commercially available, but only sparingly so. However, optimal RNA modification mapping requires the generation of sufficient overlapping digestion products from multiple RNases to reduce redundancies in digestion product sequences and modification placement.

Alternative strategies for generating overlapping digestion products exist. These include partial RNase digestion, the use of non-specific nucleases, and alkaline hydrolysis. However, these strategies also suffer from certain drawbacks, including non-specificity of digestion and ineffective reaction conditions causing too much or too little digestion. These drawbacks lead to poor analytical reproducibility and labor-intensive optimization processes. Therefore, new RNases with complementary nucleoside specificity to be used in RNA modification mapping could prove useful.

RNase MC1, a member of the RNase T2 family first isolated from bitter gourd seeds, is known to exhibit uridine-specific cleavage of RNA. Further, cucumber seed derived Cusativin is known to exhibit cytidine-specific cleavage of RNA. However, these RNases are not available commercially or on a large scale.

SUMMARY

In an attempt to overcome the noted deficiencies, aspects of the present invention are directed toward recombinant RNases.

The present invention is premised on the realization that a codon sequence may be selectively modified to be capable of adjusting usage of a target gene to resemble that of highly expressed genes, such as ribosomal proteins and elongation factors, of a host. Thus, overexpression of desirable non-host genes in a host, such as *Escherichia coli* (hereinafter "*E. coli*"), may be enhanced. A first embodiment of the invention is directed to a recombinant RNase. In an embodiment, the recombinant RNase is a recombinant RNase MC1. In another embodiment, the recombinant RNase is a recombinant RNase Cusativin.

A further embodiment of the invention is directed to a method of analyzing an RNA sequence. The method includes digesting the RNA with a recombinant ribonuclease to give digestion products comprising nucleotides of the RNA sequence; and analyzing the digestion products using an analytical method to provide the identity of at least some of the nucleotides. The recombinant ribonuclease includes at least one of a uridine-specific recombinant RNase MC1 and a cytidine-specific recombinant RNase Cusativin. In one embodiment, the analytical method may include high throughput screening. In the same or a different embodiment, the analytical method may include mass spectrometry.

Yet another embodiment of the invention is directed to a method of making a recombinant RNase. The method includes adding a recombinant DNA sequence into a host; activating expression of the recombinant DNA sequence within the host to produce the recombinant ribonuclease; and isolating the recombinant ribonuclease from the host. The recombinant ribonuclease includes at least one of a uridine-specific recombinant RNase MC1 and a cytidine-specific recombinant RNase Cusativin.

The objects and advantages of the present invention will be further appreciated in light of the following detailed description and drawings provided herein.

BRIEF DESCRIPTION OF THE DRAWINGS

The accompanying drawings, which are incorporated in and constitute a part of this specification, illustrate embodiments of the invention and, together with a general description of the invention given above and the detailed description given below, serve to explain the principles of the invention.

FIG. 1A provides a listing of all possible codons that are capable of coding for the amino acid sequence of RNase MC1.

FIG. 1B provides a nucleotide sequence for a recombinant RNase MC1.

FIG. 2A provides a listing of all possible codons that are capable of coding for the amino acid sequence of RNase Cusativin.

FIG. 2B provides a natural nucleotide sequence for RNase Cusativin.

FIG. 2C provides the nucleotide sequence coding for a recombinant RNase Cusativin.

FIG. 2D provides an alignment of the natural nucleotide sequence coding for RNase Cusativin with the recombinant nucleotide sequence.

DETAILED DESCRIPTION

Figure 3:
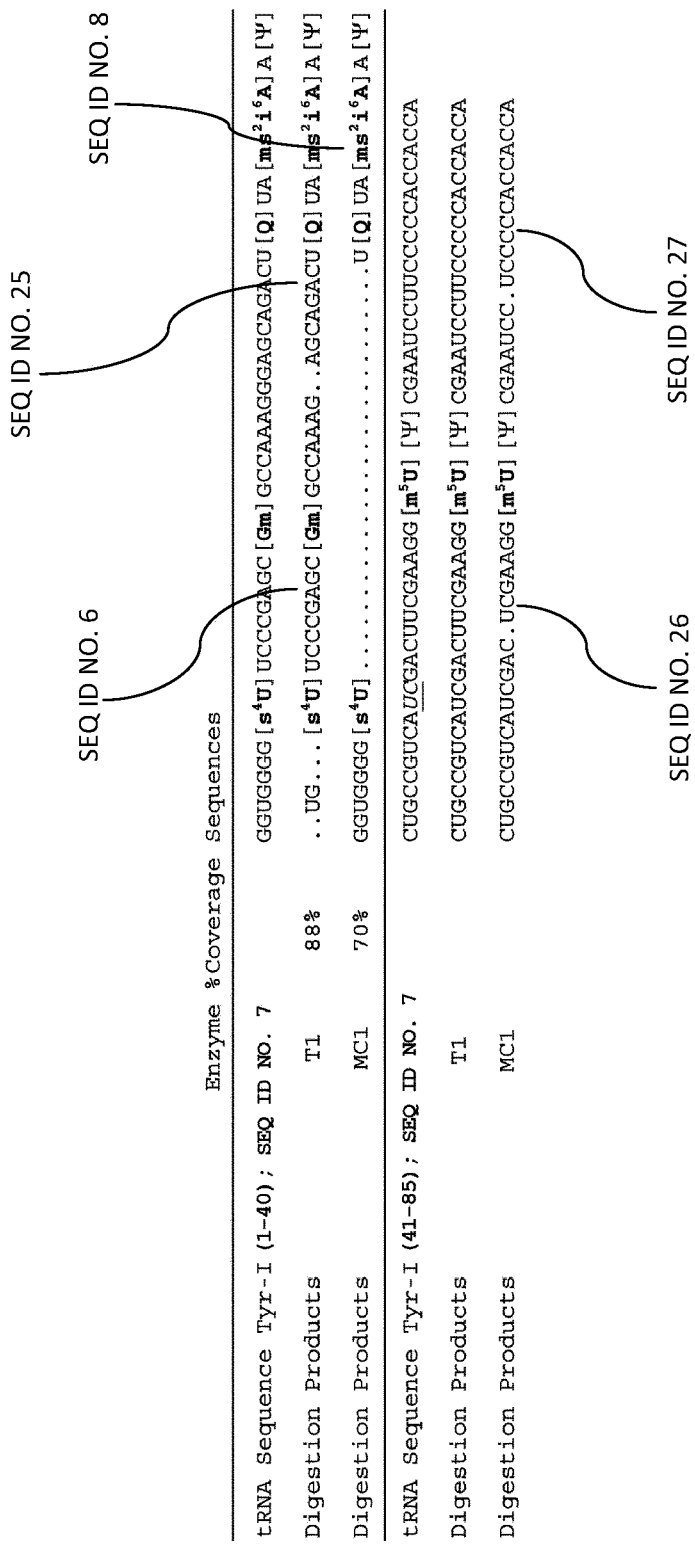
FIG. 3 is a comparison of digestion products from RNase T1 and RNase MC1.

Unless clearly defined otherwise from the context, any range of values presented in the following Detailed Description and Claims includes each end point as well as each whole number or fractional part thereof, within the recited range. Additionally, approximating language may be applied to modify any quantitative representation that may vary without resulting in a change in the basic function to which it is related. Accordingly, a value modified by a term or terms, such as "about" and "substantially," may not be limited to the precise value specified.

According to exemplary embodiments of the present invention a recombinant RNase is disclosed. The recombinant RNase is prepared from a recombinant nucleic acid sequence. In an embodiment, the RNase is a uridine-specific recombinant RNase MC1 having a codon sequence that has been selectively modified to enhance expression in a host. In an embodiment, the RNase MC1 has SEQ ID NO. 1 In another embodiment, the RNase is a cytidine-specific recombinant Cusativin having a codon sequence that has been similarly selectively modified to enhance expression in a host. In an embodiment, the recombinant RNase Cusativin has SEQ ID NO. 2.

Alternative embodiments may include other sequences of RNase MC1 and/or RNase Cusativin wherein the codons are selectively modified to cause enhanced expression in a host. In addition, the host may include any system capable of providing the necessary components for protein expression. Stated differently, the invention is not limited only to the use of *E. coli* as the host.

FIG. 1A provides a listing of all possible codons that are capable of coding for the amino acid sequence of RNase MC1, while FIG. 2A provides a listing of all possible codons that are capable of coding for the amino acid sequence of RNase Cusativin. The natural nucleotide sequence of RNase MC1 is unknown. However, the amino acid sequence is known, and is the basis for the information contained in FIGS. 1A and 1s provided as SEQ ID NO. 1. A nucleotide sequence for a recombinant RNase MC1 is given in FIG. 1B (SEQ ID NO. 2). The natural nucleotide sequence for RNase Cusativin, however, is known and is presented in FIG. 2B (SEQ ID NO. 3). FIG. 2C provides the nucleotide sequence coding for a recombinant RNase Cusativin designed to encourage overexpression in a host (SEQ ID NO. 4). The amino acid sequence of Cusativin is given by SEQ ID NO. 5. FIG. 2D provides an alignment of the natural nucleotide sequence coding for RNase Cusativin (SEQ ID NO. 3) with the recombinant nucleotide sequence of FIG. 2C coding for the recombinant RNase Cusativin (SEQ ID NO. 4). Although one embodiment each of the nucleotide sequence coding for the recombinant RNase MC1 and RNase Cusativin are provided, it should be emphasized that, in embodiments of the invention, other recombinant codon combinations could also produce functional protein, and the invention is not limited only to the two recombinant sequences provided in FIGS. 1B and 2C.

To prepare the recombinant RNase MC1, a natural MC1 amino acid sequence was used as a template in a codon modification tool. Restriction sites were added at the 5'- and 3'-ends to the recombinant codon sequence so that fusion of a tag for enzyme localization and fusion of a purification tag could later be performed on these available termini. After optimization of expression conditions, active protein was successfully purified and characterized. The uridine-specificity of the recombinant RNase MC1 was confirmed experimentally.

To prepare the recombinant Cusativin, natural Cusativin was purified from bulk cucumber seeds, and partial protein sequencing was conducted using MS. This partial protein sequence information was used to identify the protein coding sequence of the Cusativin gene in the cucumber genome. A synthetic RNase Cusativin gene with its codons changed to improve overexpression of the protein in a host was designed. After the expression conditions for the host was optimized, active protein was successfully purified and characterized. The cytidine-specificity of the recombinant Cusativin was confirmed experimentally.

In embodiments of the invention, the recombinant RNases may be used to analyze an RNA sequence. To analyze the RNA sequence, the RNA must first be digested by the recombinant RNase. Then, an analytical method is used to analyze the digested RNA.

During digestion of the RNA sequence, without intending to be bound by any particular theory, it is believed that the recombinant RNase MC1 cleaves RNA at the 5'-end of the substrate nucleoside, uridine, with the phosphate being retained on the 3'-end of the preceding nucleoside. However, most known RNases cleave RNA at the 3'-end of the substrate nucleoside. Indeed, this behavior was observed with the recombinant Cusativin, which cleaved RNA at the phosphodiester bond 3'-end with high specificity.

The analytical method may include one or more of MS, polyacrylamide gel electrophoresis (hereinafter "PAGE"), and high throughput sequencing methods, among other methods.

In one embodiment, the digested RNA may be analyzed by MS. For instance, analysis may be performed using IP-RP-HPLC-MS, LC-MS, or CID-MS/MS, among other methods. One of ordinary skill in the art is capable of selecting the appropriate analytical technique for the particular application of the inventive method.

In the same or a different embodiment, the analytical method may be a high throughput sequencing method. For instance, the high throughput sequencing method may be Next-Gen RNA-Seq. These methods may be used to discover potential modifications in any type of cellular RNA, either coding or non-coding, including mRNA, tRNA, rRNA, lncRNA, among others.

With an understanding of the cleavage specificity of MC1 and Cusativin, the predicted advantages of including these RNases within a general RNA modification mapping strategy are significant. For instance, RNase MC1, with its demonstrated uridine specificity, directly complements data obtained from the guanosine-specific RNase T1, allowing four of the five nonpseudouridine modifications to be unambiguously placed within the overall sequence (Table 1). Indeed, a comparison of the sequenced T1 digestion products (SEQ ID NO. 6, Seq ID NO. 25) of tRNA$^{Tyr\ I}$ (SEQ ID. NO. 7) with that found here after MC1 digestion (SEQ ID NO. 8, SEQ ID NO. 26, and SEQ ID No. 27)) results in >95% tRNA sequence coverage, as shown in FIG. 3. In FIG. 3, the nucleotides at position 46 and 47, shown in underlined italics, are substituted by CA for the isodecoder tRNA$^{Tyr\ II}$, resulting in a digestion product UCACAGAC instead of UCA and UCGAC from positions 47 to 47:7. Detection of all three digestion products indicates the presence of both isodecoders in the sample. Modified nucleosides are denoted by boldface, bracketed text. (Ψ) is pseudouridine, (m$^5$U) is 5-methyluridine, (s$^4$U) is 4-thiouridine, (Gm) is 2'-O-methylguanosine, (Q) is queuosine, (ms$^2$i$^6$A) is 2-methylthio-N$^6$-(3-methyl-2-butenyl)adenosine. Additionally, a further digestion by RNase Cusativin (not shown) provides nearly complete sequence coverage.

TABLE 1

| MC1 Products | T1 Products |
|---|---|
| pGGP (m/z 787.2) | UGp |
| UGGGG[s$^4$U]p (m/z 1012.1) | [s$^4$U]UCCCGp |
| U[Q]UA[ms$^2$i$^6$A]Ap (m/z 1100.5) | AGp |
| ΨCp (m/z 628.3) | C[Gm]Gp |
| UGCCGp (m/z 811.1) | CCAAAGp |
| UCAp (m/z 957.2) | CAGp |
| UCGACp (m/z 803.1) | ACU[Q]UA[ms$^2$i$^6$A]AΨCUGp |
| UCGAAGG[m$^5$U] (m/z 1320.5) | (SEQ ID NO. 10) |
| [Ψ]CGAAp (m/z 815.1) | CCGp |
| UCCp (m/z 933.2) | UCAUCGp |
| UCCCCCACCACCA (m/z 1325.3) | ACUUCGp |
| (SEQ ID NO. 9) | AAGp |
| | [m$^5$U][Ψ]CGp |
| | AAUCCUUCCCCCACCACCA |
| | (SEQ ID NO. 11) |

Figure 8:
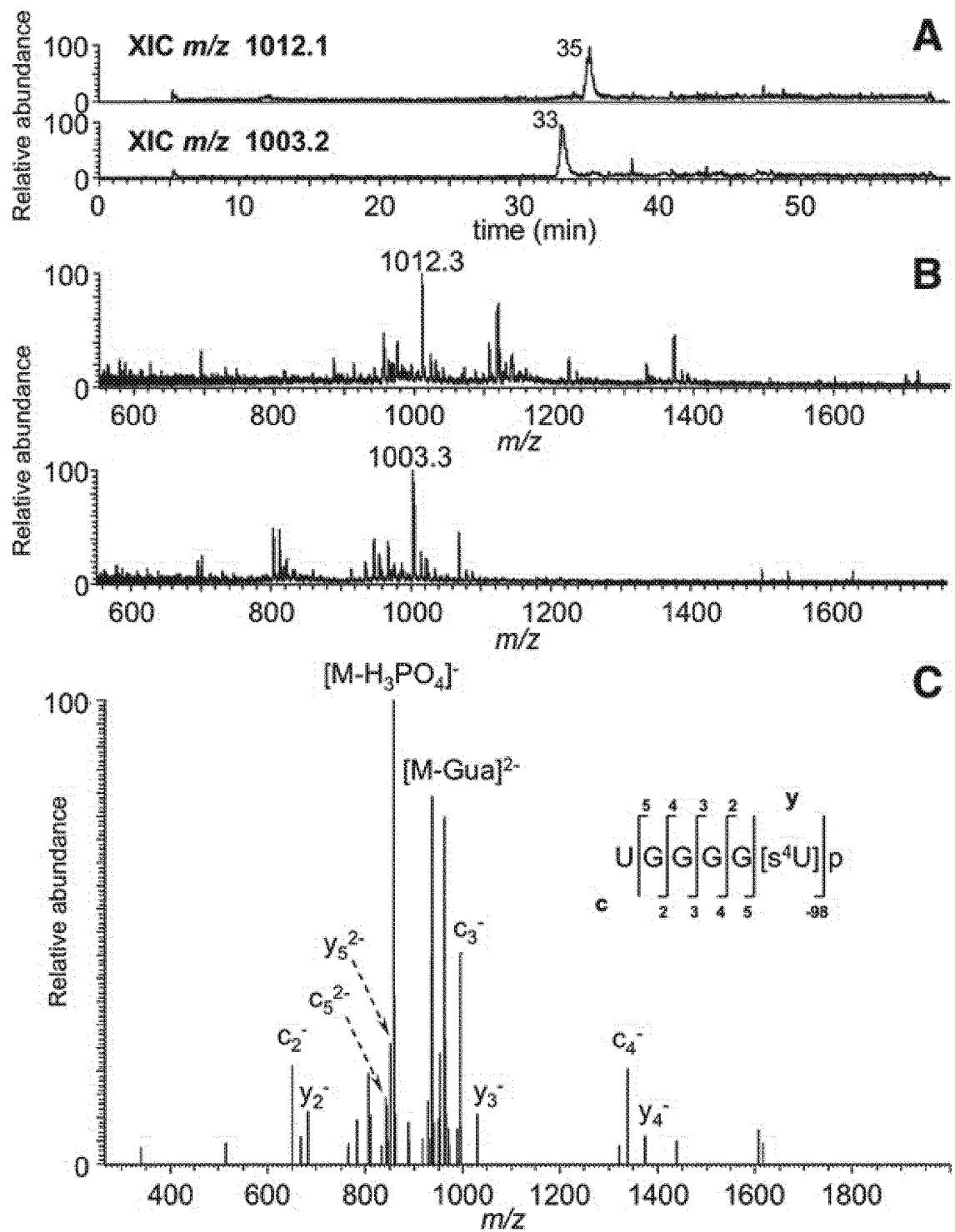
FIG. 8 is MS data for the UGGGG[$2^4$U] digestion product.

A further advantage of another nucleoside-specific RNase was noted by the detection of an MC1 digestion product, UCGCAGACp, m/z 1284.3, positions 46-53, as shown in FIG. 8, by LC-MS that arises from a second isodecoder (tRNA$^{Tyr\ II}$) in the commercial sample. One would predict that GC-rich RNAs would be more amenable to RNase MC1 analysis as larger oligonucleotide digestion products should be generated. Conversely, GC-poor RNAs would remain amenable to RNase T1, with the two used in tandem being a preferred option.

Another significant advantage of RNase MC1 for RNA modification mapping by mass spectrometry is the inherent challenge in characterizing oligonucleotides containing multiple cytidines and uridines. Uridine differs from cytidine by 1 Da (0 versus NH), and the presence of C-13 isotopes, which are readily detected by mass spectrometry, can easily result in challenges in differentiating the number and sequence location of these pyrimidines. This challenge is particularly noteworthy for larger digestion products wherein the "all light" (C-12) isotope peak is no longer the most abundant. Because digestion with MC1 ensures a single uridine will be present at the 5'-terminus of each digestion product, the number of cytidines should also be more easily determined based on accurate mass measurements and prior sequence reconstruction challenges will be minimized.

The advantages of a uridine-specific nuclease that is inhibited by modifications (except pseudouridine) should also accrue in other areas. Methylated uridines, for example, should be detectable in RNA-seq analyses as each site would be missed during MC1 digestion. A comparison of RNA-seq transcripts generated using this nuclease against the genomic prediction would, therefore, reveal such post-transcriptional modifications on a genome-wide basis. Other biochemical approaches that have effectively been limited to RNase T1, such as RNA footprinting, should also benefit from an additional RNase of high specificity.

Similar advantages are expected to inure to the cytidine-specific Cusativin. Additionally, Cusativin exhibits lower rate of cleavage of the phosphodiester bond between cytidines. When the RNA has cytidines in tandem, Cusativin exhibits a lower rate of cleavage, unlike other enzymes such as Rnase T1, U2, or MC1. This feature is useful for mapping cytidine modifications even in a cytidine rich sequence of RNA. Such a feature is not known to be present with any of the other RNase.

EXAMPLES

Design of Synthetic Gene and Cloning

Using the MC1 amino acid sequence as a template, a synthetic gene with the natural codon bias of *E. coli* was designed using the codon modification tool from Integrated DNA Technologies available at http://www.idtdna.com/CodonOpt. The resulting sequence is provided as SEQ ID NO. 1. BamH1 and HindIII sites were added at the 5'- and 3'-ends, respectively, to enable cloning into the IPTG (Isopropyl β-D-1-thiogalactopyranoside)-inducible expression cassette of the pET22b vector (EMD-Millipore). Such a strategy was expected to yield an MC1 polypeptide with an N-terminal fusion of the pelB leader peptide and a C-terminal fusion of the His-tag $(His)_6$ sequence. The pelB signal peptide is expected to direct the fusion protein to the periplasmic space, thus obviating any potential deleterious effects of ribonuclease activity on host cell RNA machinery.

After confirming the sequence and reading frame of the recombinant clone through translation of the experimentally obtained sequence, Rosetta (DE3) cells bearing the recombinant pET22b-MC1 were used for MC1 production. Rosetta DE3 cells were transformed with recombinant pET22b (+) MC1 plasmid and plated on an LB-ampicillin (50 μg/mL) and chloramphenicol (34 μg/mL) plate. A single colony was then grown overnight in LB-medium supplemented with ampicillin and chloramphenicol for a starter culture. The starter culture was subsequently used to inoculate either 0.20 L (small scale) or 1 L media supplemented with antibiotics. The cells were grown in an orbital shaker at 30° C. with constant shaking at 200 rpm. Expression was induced by adding IPTG to the broth media.

Optimization of Protein Expression Conditions

Four different experimental variables—growth stage for protein induction, growth temperature, duration of induction, and concentration of inducer—were investigated to determine the optimal conditions for inducible expression of RNase MC1.

Figure 4:
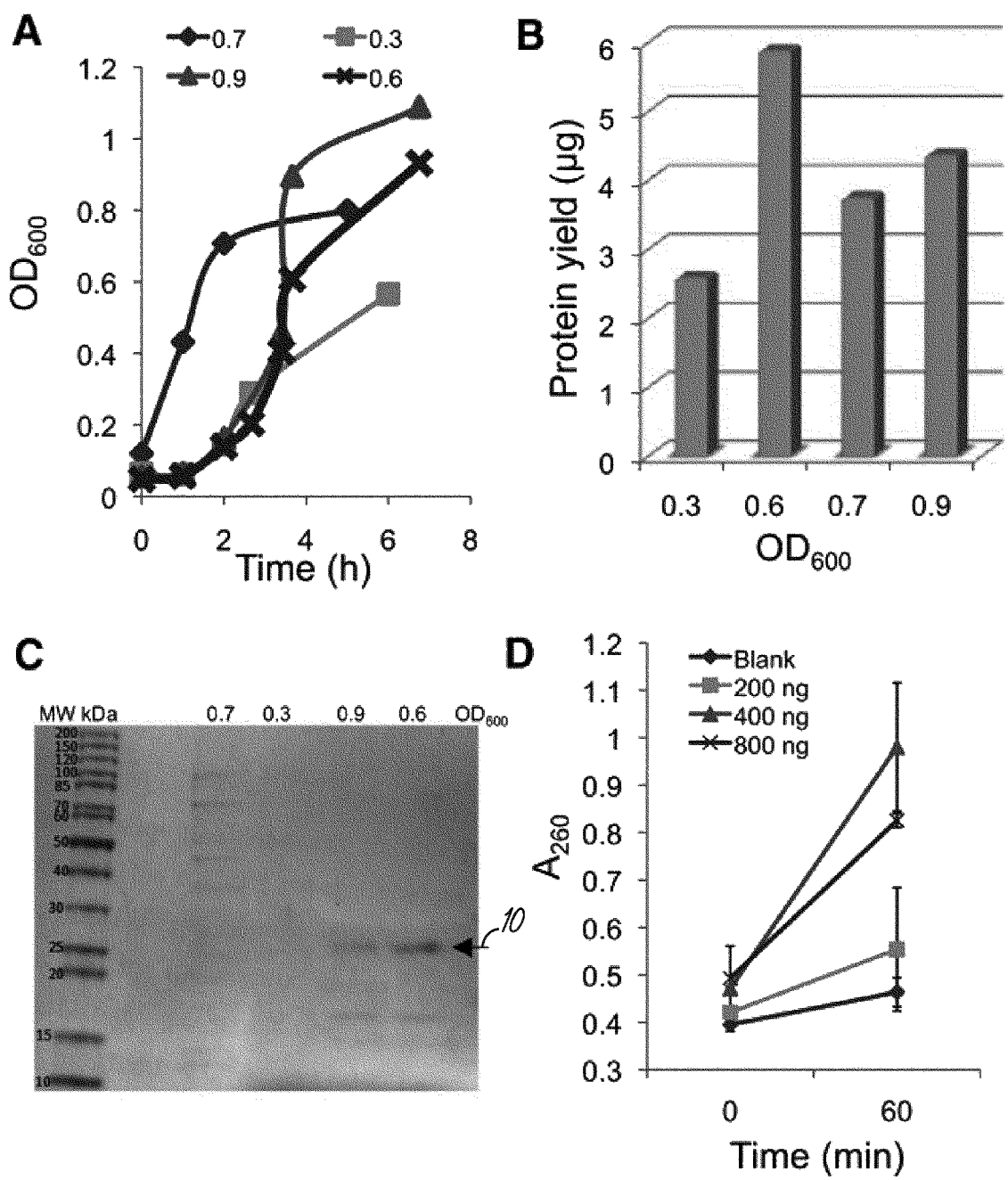
FIG. 4A is a representative growth curve of *E. coli* cells used to produce the recombinant RNase MC1.
FIG. 4B is a comparison of the protein amounts purified harvested cells at various values of $OD_{600}$.
FIG. 4C is an SDS-PAGE of a purified recombinant RNase MC1.
FIG. 4D is a comparison of $A_{260}$ observed with various amounts of RNase MC1.

Specifically, different bacterial growth stages (measured by optical density at 600 nm ranging from 0.3 to 0.9 units) were evaluated for protein induction. Four different flasks of 200 mL LB media supplemented with ampicillin and chloramphenicol were inoculated with 2 mL from the same starter culture of a Rosetta (DE3) cell line bearing the recombinant plasmid. One mL of cells was drawn at regular intervals (30-90 min) to measure the optical density at 600 nm. MC1 expression was induced by adding IPTG at different stages in the log-phase growth curve as measured by optical cell densities ranging from 0.3 to 0.9 units at $\lambda_{600}$. FIG. 4A depicts the representative growth curves following induction at each growth stage. In almost all cases, inducible expression of MC1 resulted in a change n the growth curve, shifting growth into the log phase. A comparison of the protein amounts purified from harvested cells revealed higher yields when cells were induced around an $OD_{600}$ of 0.6, as shown in FIG. 4B.

The purified protein was analyzed for its relative molecular mass and purity by SDS-PAGE, as shown in FIG. 4C. This analysis revealed a major polypeptide band at $M_r$~24 kDa (indicated at arrow 10) with a few minor polypeptides of low molecular mass when cells were induced at an $OD_{600}$ of 0.6 and 0.9. The expected molecular mass of the MC1-$(His)_6$ fusion protein (24.1 kDa) is similar to that observed in SDS-PAGE, suggesting the production of the anticipated polypeptide in the bacterial host. Surprisingly, no such polypeptide was observed when cells were induced at $OD_{600}$ of 0.3 and 0.7. An examination of the respective growth curves suggests that the optical density remains essentially unchanged after 3 h of induction at $OD_{600}$ of 0.7, indicating the suspension of metabolic activity in these host cells. Induction at early log phase ($OD_{600}$ of 0.3) did not produce the anticipated polypeptide, likely because of a lower cell count and slower multiplication of cultured cells. Although induction at $OD_{600}$ of 0.9 resulted in the ~24 kDa polypeptide, the resulting protein yield was significantly less than the amount observed when induction occurred at $OD_{600}$ of 0.6. Hence, induction at $OD_{600}$ of 0.6 was considered optimal for expression of MC1 protein in the *E. coli* host.

The optimal duration of MC1 induction was observed to be 2 h from the point of IPTG addition at $OD_{600}$ of 0.6, where protein yield peaked at ~5 μg per 200 mL culture. Altering the growth temperature between 30° C. and 37° C. and IPTG concentrations between 0.4 and 1.0 mM had no significant impact on protein yield, which remained unchanged at ~5 μg per 200 mL culture (data not shown).

RNase MC1 Purification

The induced MC1 protein was purified by either a batch process or column chromatography using a Nickel-Sepharose resin (Novagen) as per the manufacturer's instructions. Batch purification was employed during investigation of the optimal expression conditions, and column chromatography was performed for large-scale purification. The purified protein yield was measured by Bradford assay. The eluted protein was exchanged with 100 mM ammonium acetate (pH 5.5) buffer and concentrated using an Amicon Ultra 0.5 mL filter.

Characterization of MC1 for Mapping Nucleoside Modifications

The presence of putative MC1 protein in the eluted fractions was confirmed by the detection of a ~24 kDa polypeptide on 4%-20% denaturing polyacrylamide gels (Precise, Thermo Scientific). Nonspecific RNase activity of the purified protein was tested by incubating 200 pmol of a substrate oligonucleotide, UAACUAUAACG (SEQ ID NO. 12), and defined amounts (100-800 ng) of protein at 37° C. for 1 h in a 10 µL volume. UV-absorbance measurements at 260 nm ($A_{260}$) were recorded at $T_0$ and after 1 h ($T_{1h}$) on a nanophotometer (Implen) as per the manufacturer's instructions. Buffer controls containing RNA oligomer with no protein were also assayed in an identical fashion.

Cleavage of SEQ ID NO. 12 by the RNase will result in oligonucleotide products with reduced stacking interactions compared with the starting substrate leading to an increase in $A_{260}$ values. Three protein amounts were tested (200, 400, and 800 ng). An increase in $A_{260}$ was measured when increasing the protein amount from 200 to 400 ng, while no additional increase was detected at 800 ng of protein, as shown in FIG. 4D. Presumably, the higher protein amount resulted in no further cleavage of the oligonucleotide substrate or the increased protein amount interferes with detection of any additional changes in the UV absorbance.

The nucleoside-specific enzymatic cleavage of RNA by the purified protein was tested by incubating 3 µg of the commercially available *E. coli* tRNA$^{Tyr\ I}$ (Sigma-Aldrich) with a defined amount of purified enzyme (100-2000 ng) at 37° C. for 2 h and analyzing the digestion products by IP-RP-HPLC-MS. The digestion products were separated on a 1×150 mm XBridge C18 column (Waters) employing mobile phase A (200 mM hexafluoroisopropanol [HFIP] [Sigma], 8.15 mM triethylamine [TEA, Fisher Fair Lawn] in water [Burdick and Jackson, Bridgeport], pH 7.0) and mobile phase B (100 mM HFIP, 4.08 mM TEA in 50% methanol [Burdick and Jackson], pH 7.0) at a flow rate of 30 µL/min. The gradient was as follows: 5% B to 20% B in 5 min; 20% B to 30% B in 2 min; 30% B to 95% B in 43 min; hold at 95% B for 5 min, followed by equilibration for another 15 min at 5% B.

The eluted digestion products were subjected to mass analysis using a Thermo Scientific LTQ-XL mass spectrometer. The instrument settings for automatic acquisition of tandem mass spectrum of each mass-selected precursor ions are known and will not be further described. The sheath gas, auxiliary gas, and sweep gas at the ionization source were set to 25, 14, and 10 arbitrary units (au), respectively. The spray voltage was 4 kV, the capillary temperature was 275° C., the capillary voltage was −23 V and the tube lens was set to −80 V.

The theoretical m/z (mass/charge) values of putative digestion products (both U-specific and nonspecific) and the corresponding collision-induced dissociated (CID) fragment ions were computed using Mongo Oligo (http://mods.rna.albany.edu/masspec/Mongo-Oligo). To confirm uridine specificity for digestion, an LC-MS/MS data set from RNase MC1 digestion of *E. coli* tRNA$^{Tyr\ I}$ was acquired as described. Each MS/MS spectrum was analyzed for the presence of m/z 328.1 (A), 344.2 (G), 304.1 (C), and 305.1 (U) that correspond to the $c_1$ product ion masses for the canonical nucleotides. Similarly, the MS/MS spectra were also examined for the presence of m/z 346.2 (A), 362.2 (G), 322.1 (C), and 323.1 (U) that correspond to the $y_1$ product ion masses for the canonical nucleotides assuming the digestion product was present with a 3'-linear phosphate. If none of these m/z values were observed (as in the case of longer oligomers or exclusive 2',3'-cyclic phosphates), the m/z values corresponding to the $c_2$ product ion combinations, e.g., UA/UG/UC/UU/AU/GU/CU, were considered.

Figure 5:
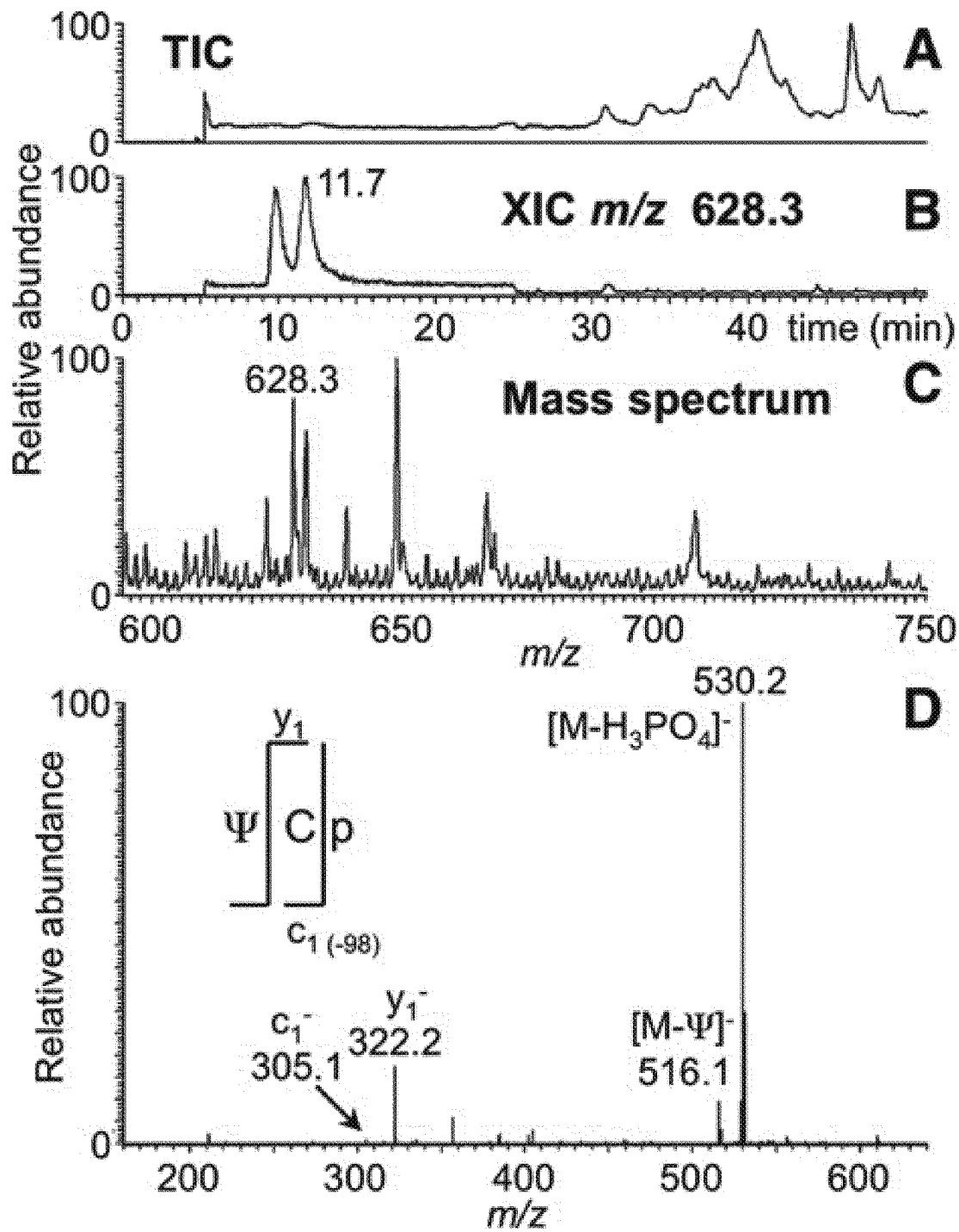
FIG. 5 is MS data for the ΨC digestion product.
Figure 6:
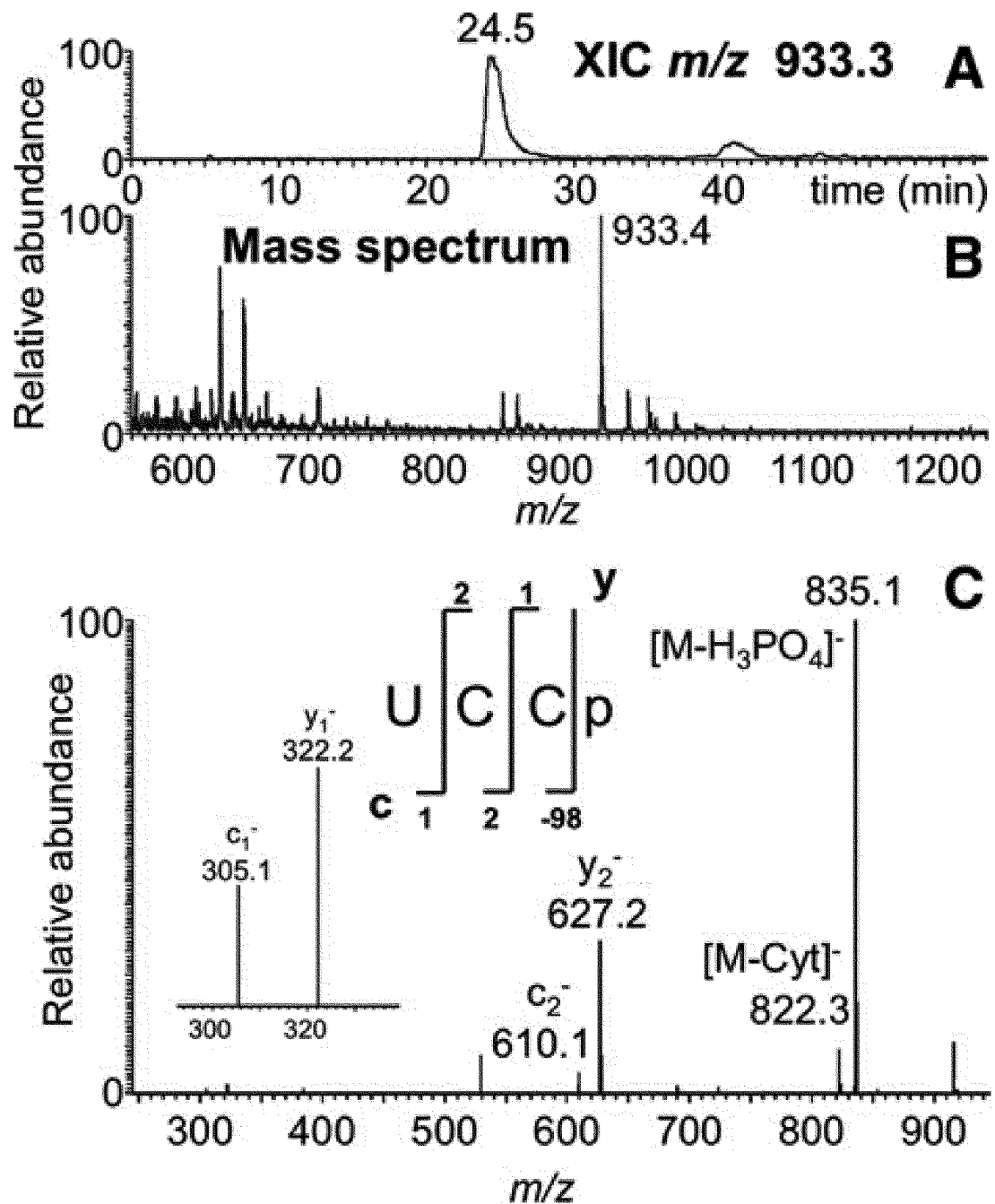
FIG. 6 is MS data for the UCC digestion product.

The nucleotide-specific cleavage properties were determined by a systematic examination of the MS/MS spectra from each oligonucleotide precursor ion whose mass is consistent with a cleavage product containing a 3'-phosphate. Evaluation of these data revealed oligonucleotide digestion products exhibiting 5'-uridine residues. In contrast, the 3'-termini of digestion products were highly variable. Uridine was conspicuous in its absence at the 3'-termini. Two such representative digestion products, ΨC and UCC, are shown in FIGS. 5A-5D and 6A-6D, respectively. In FIGS. 5A-5D, (A) is the total ion chromatogram (TIC), (B) is the extracted ion chromatogram (XIC) for m/z 628.3, corresponding to the digestion product ΨCp (position 55-56 of SEQ ID NO. 7), (C) is the mass spectrum associated with the XIC at 11.7 min., and (D) is the tandem mass spectrum (MS/MS) of the collision-induced dissociation (CID) of the m/z 628.3 precursor ion. The observed sequence informative product ions, c (with common 5' end) and y (with common 3'-end) with a subscript denoting the position of cleavage on phosphodiester backbone, are labeled and plotted following the standard nomenclature of the art. In FIG. 6, (A) is the XIC for m/z 933.4, corresponding to the digestion product UCCp (position 55-56 of SEQ ID NO. 7), (B) is the mass spectrum associated with the XIC at 24.5 min, and (C) is the CID tandem mass spectrum of m/z 933.4 precursor ion. As in FIG. 5, the sequence informative fragment ions are labeled.

For longer digestion products where the 5'-terminus could not be directly observed in the MS/MS data, fragment ions at the second position consistent with the presence of uridine were observed. Based on this examination of the MS/MS data, a list of m/z values of expected tRNA$^{Tyr\ I}$ digestion products and their collision-induced dissociation (CID) fragment ions were calculated assuming cleavage at uridine residues yielding digestion products with 5'-uridine or 5'-modified uridine nucleosides.

Figure 7:
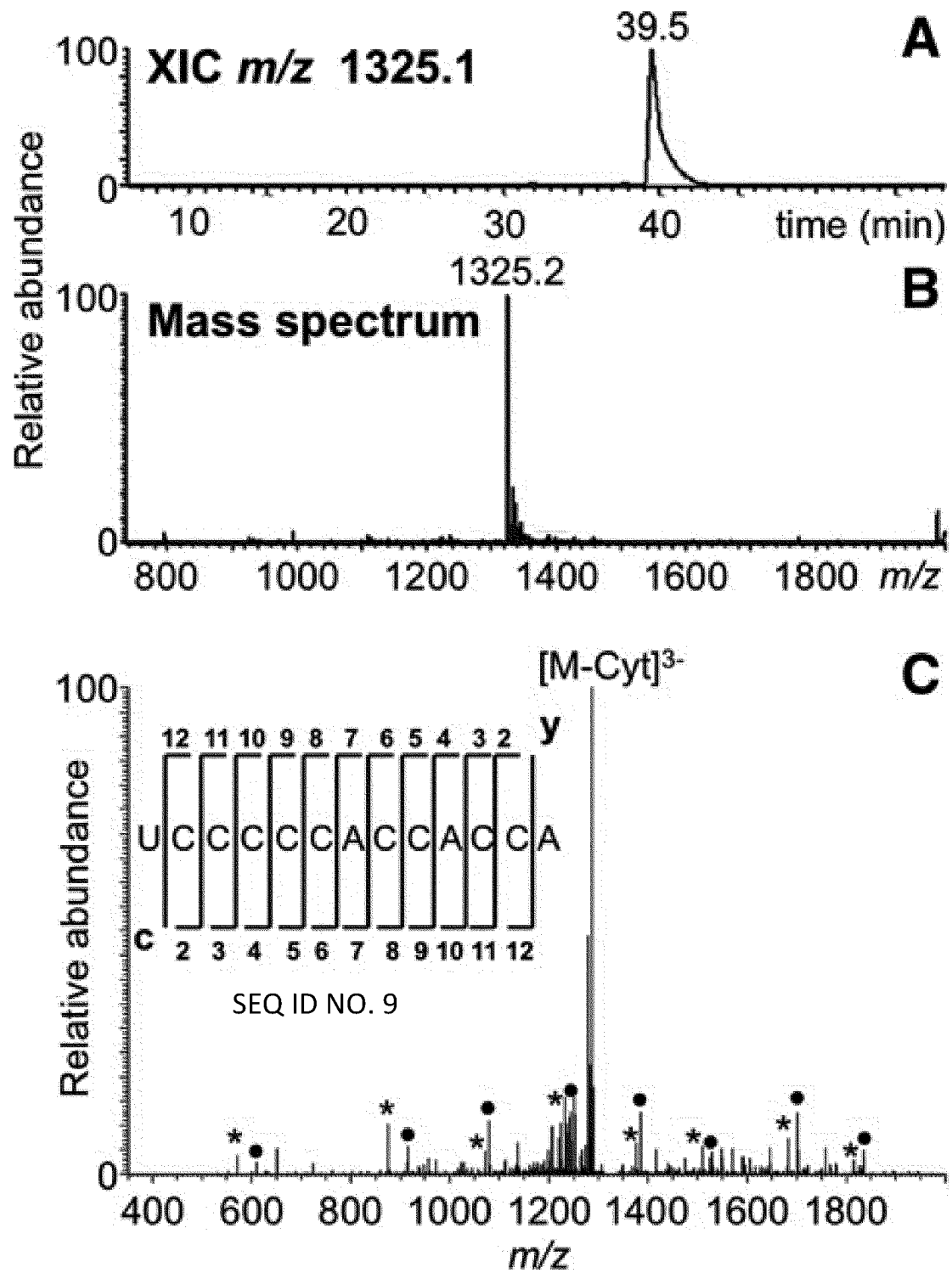
FIG. 7 is MS data for the UCCCCCACCACCA digestion product.

Using these digestion rules, the entire LC-MS/MS data set for tRNA$^{Tyr\ I}$ was examined. Among the predicted digestion products was one from the 3' end of the tRNA, UCCCCCACCACCA (SEQ ID NO. 9). This cytidine-rich digestion product was detected experimentally in high abundance, as shown in FIG. 7. In FIG. 7, (A) is XIC for m/z 1325.1, corresponding to the digestion product SEQ ID NO. 9 (position 73-85 of SEQ ID NO. 7), (B) is the mass spectrum associated with the XIC at 39.5 min, and (C) is the CID tandem mass spectrum of m/z 1325.2 precursor ion. Sequence informative fragment ions labeled as in FIG. 5. An asterisk (*) denotes c-type fragment ions and solid bullet (●) denotes y-type fragment ions. Significantly, no digestion products corresponding to cleavage at cytidine were observed in the LC-MS/MS data indicating the specificity of the purified protein toward uridine.

A further examination of the experimental data revealed the presence of 3'-linear and 2',3'-cyclic phosphates for digestion products (a representative digestion product is shown in FIG. 6). In FIG. 8, (A) is XICs of m/z 1012.3 (linear phosphate) and m/z 1003.3 (2',3'-cyclic phosphate), (B) is the MS associated with the XICs at 35 and 33 minutes, and (C) is the CID tandem mass spectrum of m/z 1012.3 precursor ion. Sequence informative fragment ions are labeled. The presence of cyclic phosphates is consistent with an RNase T2 mechanism, which proceeds via the 2',3'-cyclic phosphate intermediate before forming the 3'-linear phosphate as the final product. This feature was not enzyme concentration dependent, as excess enzyme (up to 50× enzyme) did not affect cyclic phosphate levels. Concentration-independent formation of the cyclic phosphate is more consistent with a slow rate of phosphodiester bond hydrolysis.

Cleavage Preferences at Post-Transcriptionally Modified Uridines

The tRNA$^{Tyr\ I}$ substrate allowed for an initial investigation into the influence of modified nucleosides on the cleavage properties of MC1. This tRNA contains multiple modified nucleosides: 4-thiouridine [s$^4$U8], 2'-O-methylguanosine [Gm17], queuosine [Q34], 2-methylthio-N$^6$-isopentenyladenosine [ms$^2$i$^6$A37], 5-methyluridine [m$^5$U54], and two pseudouridines [Ψ39 and Ψ55]. While uridine and pseudouridine are indistinguishable based on mass, other modifications can be directly identified by their characteristic mass shift from the unmodified canonical nucleoside, and placed within the overall tRNA$^{Tyr\ I}$ sequence upon examination of the MS/MS data.

4-Thiouridine and 5-Methyluracil

Figure 9:
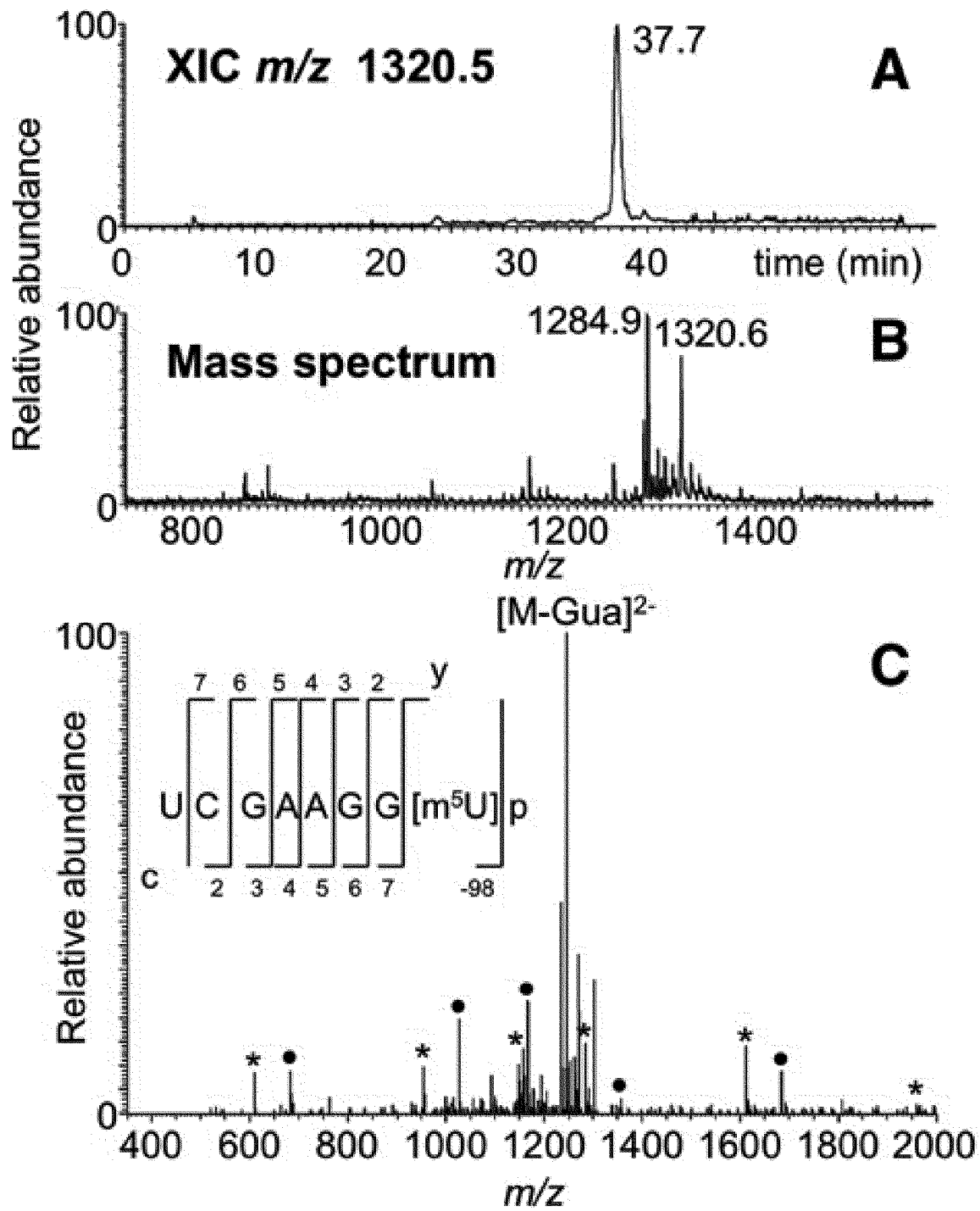
FIG. 9 is MS data for the UCGAAGG[$m^5$U] digestion product.

Of great interest was determining whether MC1 cleavage is impacted by the presence of modified uridines. As tRNA$^{Tyr\ I}$ contains three modified uridines (s$^4$U, m$^5$U, and Ψ), the LC-MS/MS data were evaluated by generating in silico predicted digestion products where s$^4$U and m$^5$U are either recognized for cleavage or not and comparing the experimental data against these predicted m/z values. The data revealed the presence of m/z values that correspond to the scenario where s$^4$U and m$^5$U are not recognized by MC1. For example, the digestion product UGGGG[s$^4$U]p was detected at m/z 1012.3 (FIG. 6A,B) and this sequence was confirmed by MS/MS (FIG. 6C). Similarly, m$^5$U was not recognized as a substrate for cleavage as noted by detection of the digestion product UCGAAGG[m$^5$U] at m/z 1320.5, which also was confirmed by the MS/MS data, as shown in FIG. 9. In FIG. 9, (A) is XIC for m/z 1320.2, corresponding to the digestion product UCGAAGG[m$^5$U] (position 47-54), (B) is the MS associated with the XIC at 37.7 minutes, and (C) is the CID tandem mass spectrum of m/z 1320.6 precursor ion. A co-eluting ion (m/z 1284.6) observed in the MS corresponds to the MC1 digestion product (UCACAGAC, position 46-53) belonging to the tRNA$^{Tyr\ II}$ isodecoder (RY1661). Sequence informative fragment ions are labeled. An asterisk (*) denotes c-type fragment ions and a solid bullet (●) denotes y-type fragment ions.

If MC1 had recognized these modified nucleosides as substrates, the digestion products would have been single nucleotides (5' monophosphates of s$^4$U or m$^5$U) as they are followed by either uridine or pseudouridine in the tRNA$^{Tyr\ I}$ sequence. To confirm that no partial cleavages at s$^4$U or m$^5$U occurred, the predicted doubly charged digestion products consistent with such cleavage, (3)-UGGGG-(7) at m/z 851.1 and (56)-UCGAAGG-(62) at m/z 1160.1, were also searched for within the data. No ions for these m/z values were detected, confirming that s$^4$U and m$^5$U are not recognized as substrates by MC1.

Pseudouridine

Figure 10:
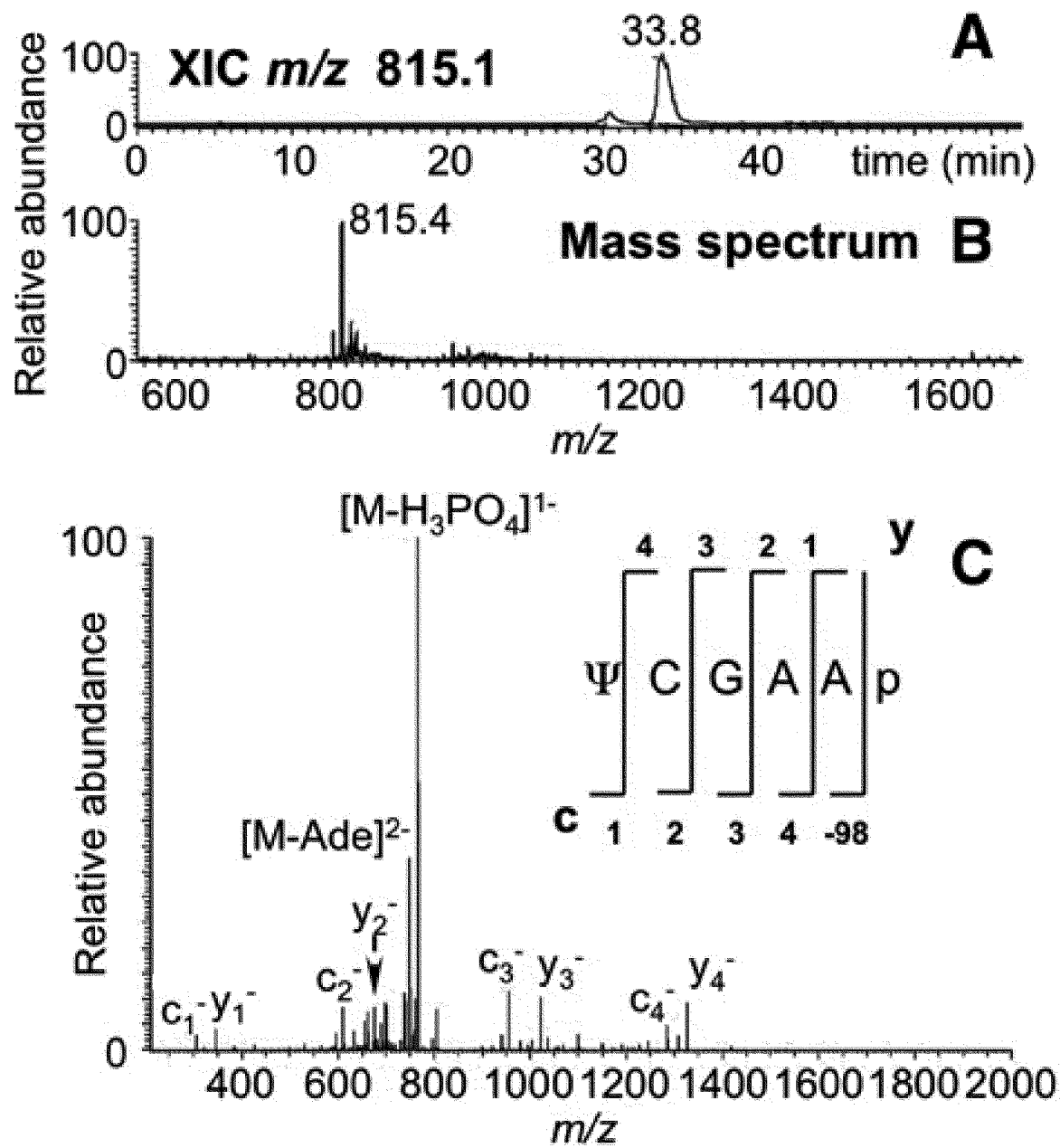
FIG. 10 is MS data for the ΨCGAA digestion product.

If MC1 recognizes pseudouridine as a substrate, the expected digestion products are predicted at m/z 628.4 (ΨpC) and m/z 815.1 (ΨCGAA). The former was found, as illustrated in FIG. 5, and data consistent with the latter is shown in FIG. 10. In FIG. 10, (A) is the XIC for m/z 815.4, corresponding to the digestion product ΨCGAAp (position 55-59), (B) is the MS associated with the XIC at 37.7 minutes, and (C) is the CID tandem MS of m/z 815.4 precursor ion. Sequence informative fragment ions are labeled. Although pseudouridine cannot be distinguished from uridine by mass, no other tRNA$^{Tyr\ I}$ digestion products corresponding to the sequence UC or UCGAA are expected. Therefore, uridine and pseudouridine are indistinguishable in terms of the nucleoside specificity of MC1.

Missed Cleavages

Figure 11:
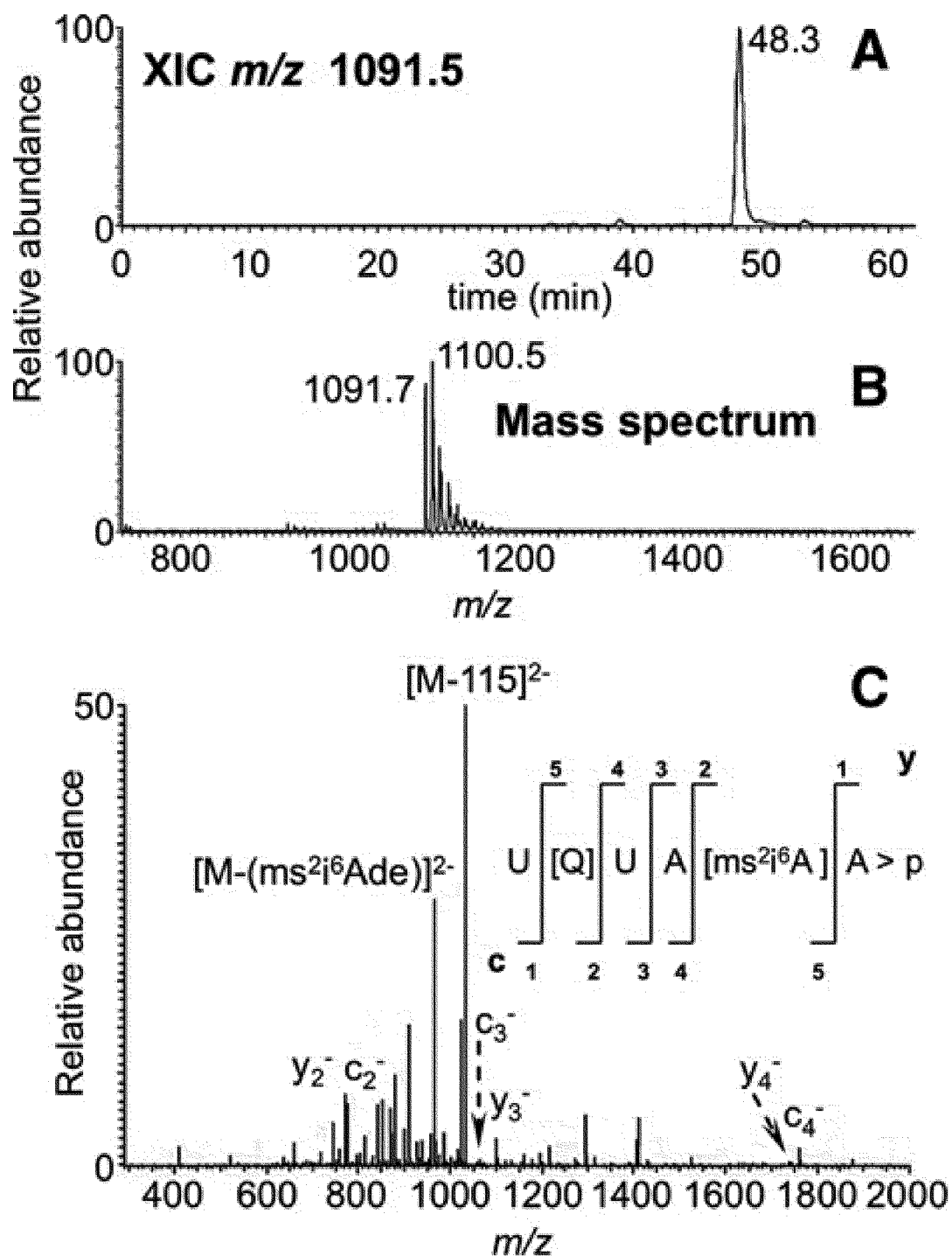
FIG. 11 is MS data for the U[Q]UA[$ms^2i^6$A]A digestion product.

An analysis of the MC1 cleavage patterns of tRNA$^{Tyr\ I}$ also revealed that cleavage was not observed if a uridine is preceded by a bulky modified nucleoside. For example, queuosine at position 34 inhibited MC1 cleavage at U35 as noted by digestion products detected at m/z 1100.5 and m/z 1091.7, which are consistent with the 3'-linear phosphate and 2',3'-cyclic phosphate digestion products, respectively, for the oligonucleotide U[Q]UA[ms$^2$i$^6$A]A, as shown in FIG. 11. Tandem MS of these precursor ions confirmed the sequence, revealing the influence of the 5'-nucleoside on uridine recognition and cleavage. In FIG. 11, (A) is XIC for m/z 1091.5, (B) is the MS associated with the XIC at 48.3 min, and (C) is the CID tandem MS of m/z 1091.7 precursor ion with sequence informative fragment ions labeled. The mass spectrum reveals the doubly charged ions for both linear (m/z 1100.5) and 2',3'-cyclic phosphate (m/z 1091.7) digestion products of U[Q]UA[ms$^2$i$^6$A]A (positions 33-38 of SEQ ID NO. 7). Fragmentation of queuosine in the oligonucleotide by loss of 115 Da is indicated in the MS.

To determine whether partial digestion at uridines occurs, tRNA$^{Tyr\ I}$ substrate was incubated with varying amounts of MC1. At low enzyme/substrate ratios (0.05-1 μg protein per 3 μg of tRNA), partial digestion at consecutive uridines was noted. These partial digestions could be eliminated by increasing the enzyme/substrate ratio (2.5 μg protein per 3 μg of tRNA).

Obtaining and Purifying the Crude Cusativin Protein Extract

Dried seeds of the pickling variety of *Cucumis sativus* were ground into flour and extracted overnight at 4° C. using 5 mM sodium phosphate (pH 7.2) containing 0.14 M NaCl with vigorous stirring. The extract was then filtered through 4 layers of cheesecloth and acidified with 20% glacial acetic acid to pH 4. The filtrate was then centrifuged for 20 min at 10,000 rpm, and the pellet was discarded. The supernatant was then centrifuged for 30 additional min at 15,000 rpm, and the resultant pellet was again discarded. The extract was then filtered through Whatman No. 1 filter paper to remove the majority of the remaining particulates.

The filtrate was then applied to a Sephadex G-25 column (2.5 mL bed volume) equilibrated with 10 mM sodium acetate (pH 4.5). The flow-through was used for the subsequent step of ion-exchange chromatography.

The eluate was then applied to a CM-Cellulose column equilibrated with 10 mM sodium acetate (pH 4.5). The column was then washed with 5 mM sodium phosphate (pH 7), and the eluate was discarded. The protein was then eluted from the column with a discontinuous gradient of 5 mM sodium phosphate (pH 7) containing 50 mM, 100 mM, 200 mM, and 500 mM NaCl. The eluate was collected in 2 mL fractions, and either Bradford Assay or the UV absorbance at 280 nm was used to identify the fractions containing the protein.

Figure 12:
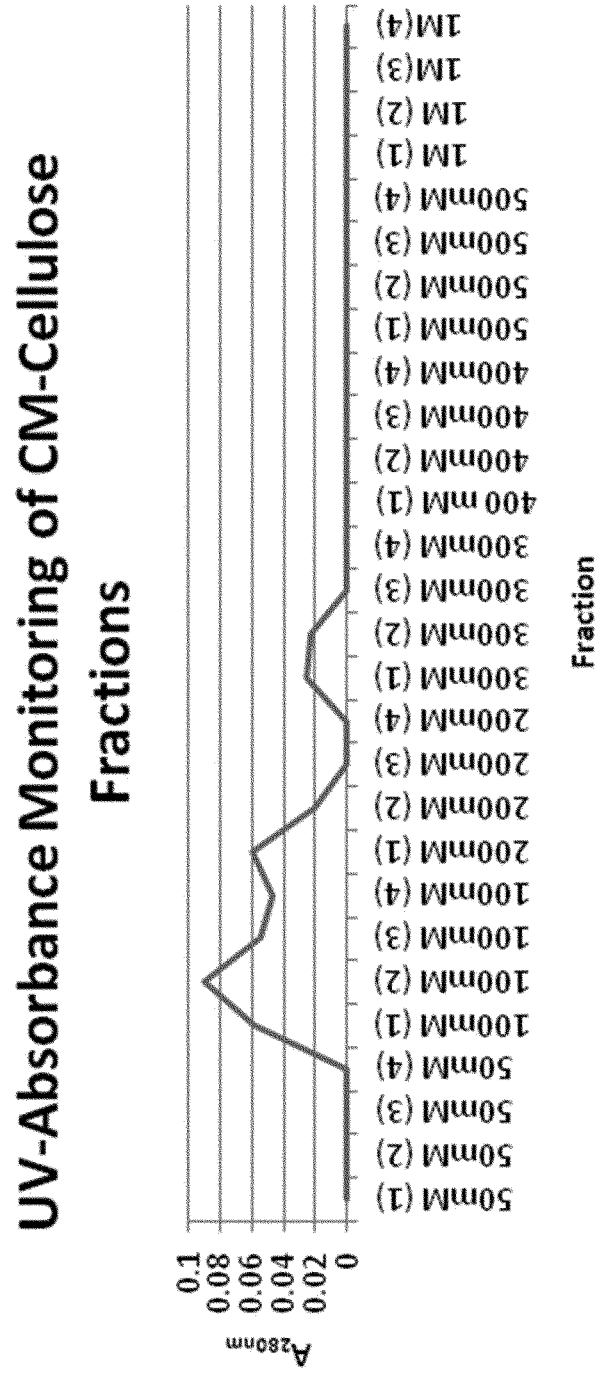
FIG. 12 shows the absorbance at 280 nm of each eluted fraction after eluting the Cusativin from a CM-Cellulose column.
Figure 13:
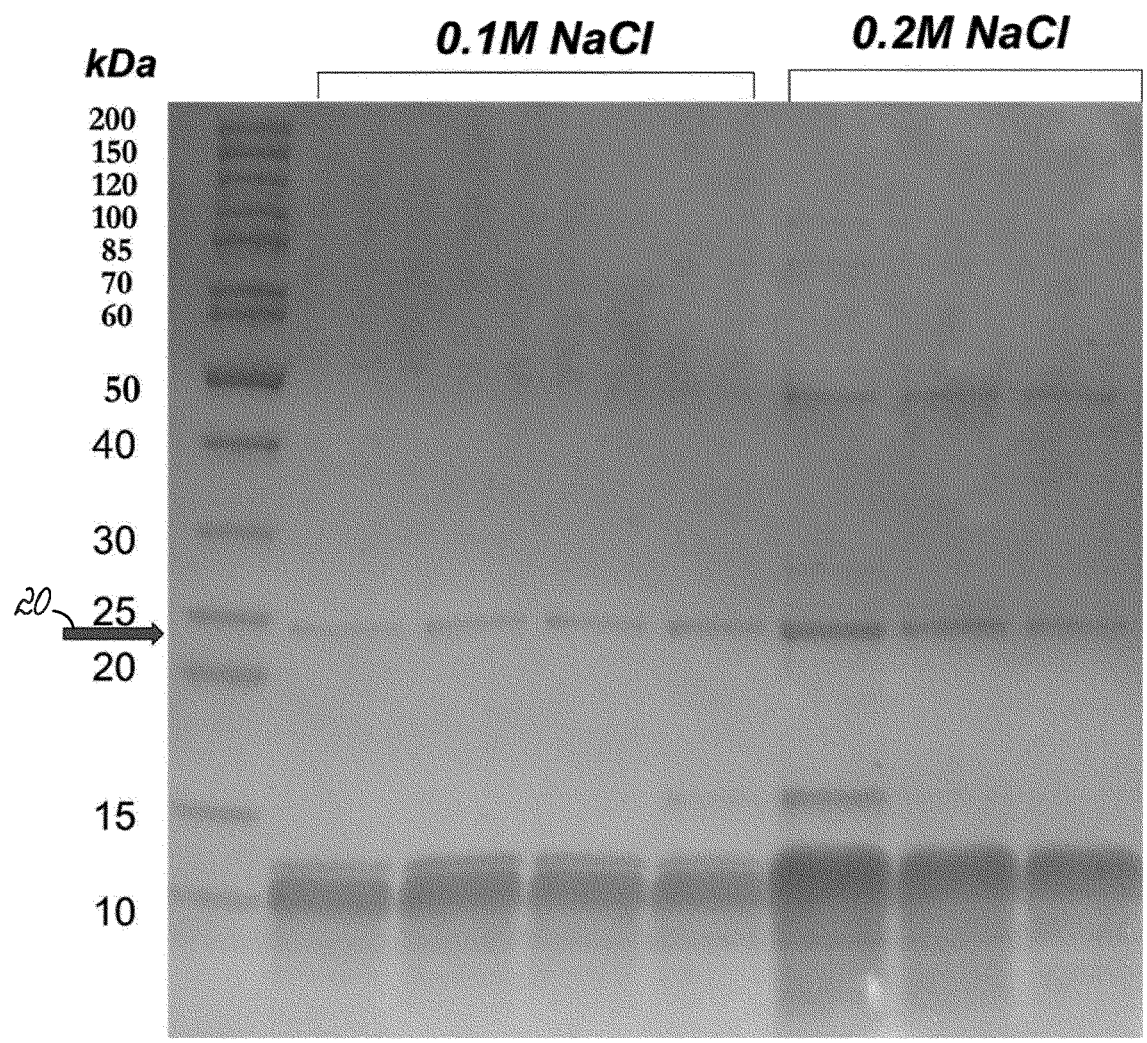
FIG. 13 shows an SDS-PAGE used to verify the presence of ~23-25 kDa polypeptide.

The presence of protein was not monitored until after the ion exchange chromatography on CM-Cellulose. After eluting the protein from CM-Cellulose column, the absorbance at 280 nm of each eluted fraction was monitored, as shown in FIG. 12. The protein-containing ion-exchange chromatography fractions exhibiting highest absorbance were subjected to denaturing gel electrophoresis (SDS-PAGE) to verify the presence of ~23-25 kDa polypeptide, based on the comparison with protein size standards (EZ run Rec Protein size standards, Fisher scientific). It was found that the target protein (~25 kDa) eluted mostly in the 5 mM sodium phosphate containing 200 mM NaCl, as shown in FIG. 13 (indicated at arrow 20). Additionally, many smaller proteins (5-10 kDa) also eluted in these fractions.

Figure 14:
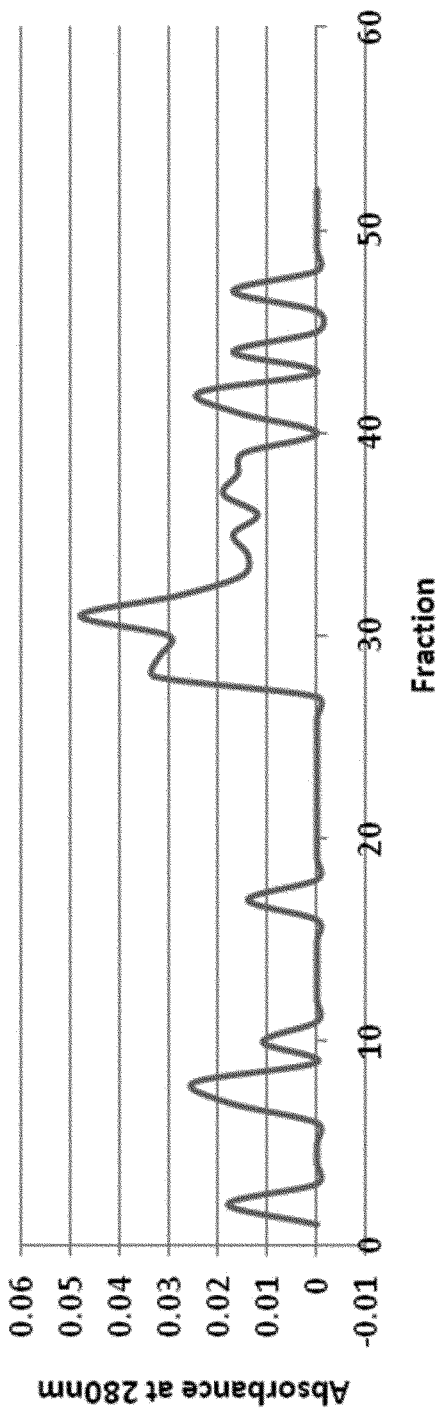
FIG. 14 shows the absorbance at 280 nm of each eluted fraction after eluting the Cusativin from a Sephadex G-75 column.

The fractions containing the 25 kDa protein were concentrated to a combined volume of 2 mL or less on a speedvac (Thermo Scientific) and subjected to size-exclusion chromatography on a Sephadex G-75 column (approximate bed volume of 36 mL, GE Life Sciences) equilibrated with 5 mM sodium phosphate (pH 7) containing 500 mM NaCl. The protein was eluted with approximately 1.5 column volumes of 5 mM sodium phosphate (pH 7) containing 500 mM NaCl. 1.5 mL fractions were collected, and a Bradford Assay was performed to determine which fractions contained protein. See FIG. 14. The presence of 23-25 kDa polypeptide in the size-exclusion column fractions was verified by SDS-PAGE. The target enzyme eluted after about 1-1.2 column volumes of buffer (fractions 30-34) had passed through the column.

The size-exclusion chromatography fractions containing a polypeptide of ~23-25 kDa were pooled, concentrated, and desalted with autoclaved water using Amicon Ultra-5 Centrifugal filter devices (size=3 k). The absorbance at 280 nm was then used to determine the approximate concentration of the pure protein (356 μg/mL).

Figure 15:
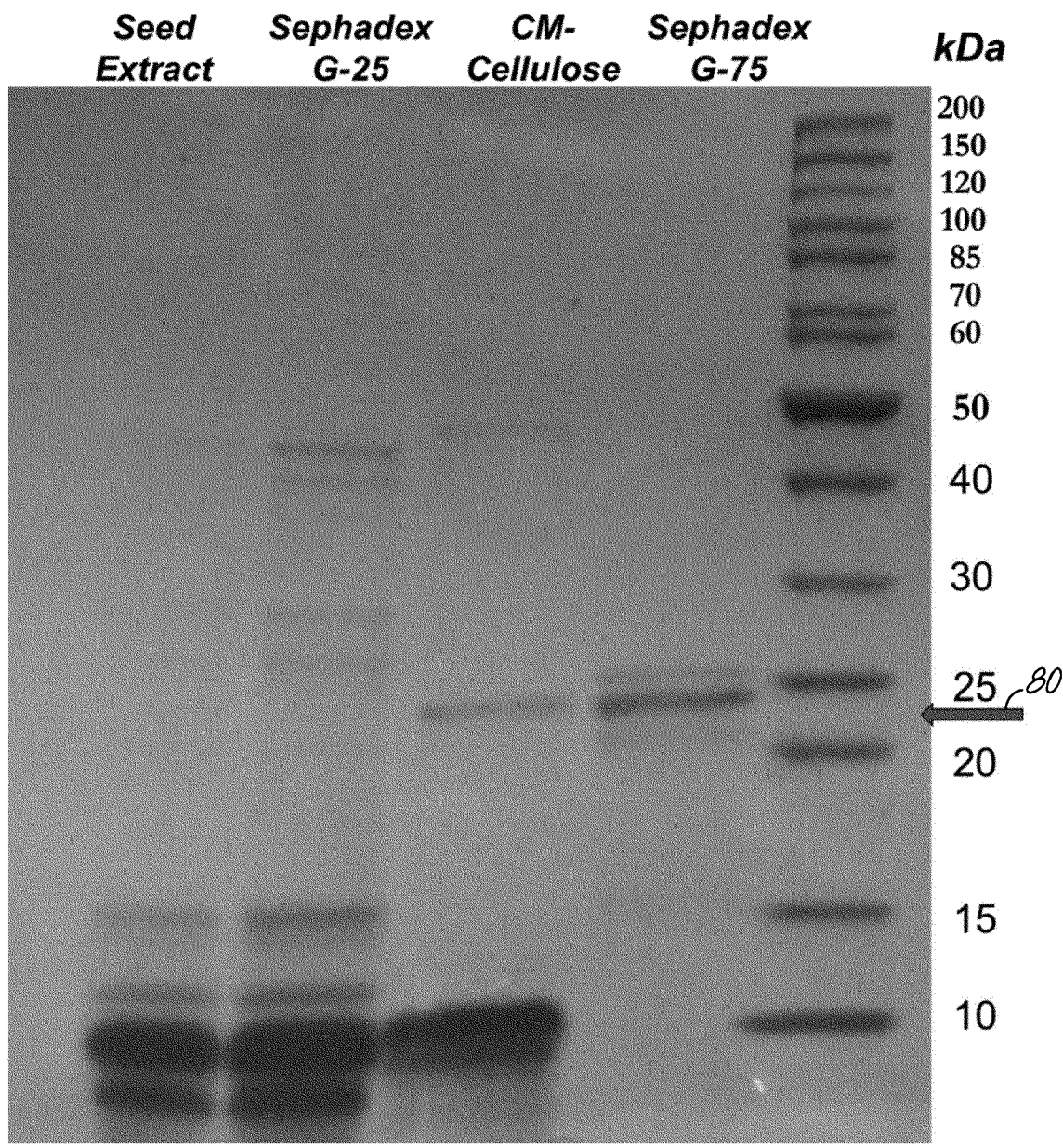
FIG. 15 is an SDS-PAGE to show the progression of RNase Cusativin purification.

Protein containing aliquots obtained at each step of purification were subjected to SDS-PAGE to show the progression of RNase Cusativin purification, as shown in FIG. 15. Following the initial extraction and centrifugation, the target enzyme (~23-25 kDa in size) was not visible on the gel, indicating its presence at very low concentration. The target enzyme was still not visible following gel-filtration on Sephadex G-25, as it filters only small molecules. It took ion exchange chromatography on a CM-Cellulose column to concentrate the target protein as it eluted with many other smaller proteins in these fractions. Size exclusion chromatography on Sephadex G-75 with high salt concentration finally separated the target protein from the smaller proteins and yielded relatively pure enzyme (indicated at arrow 80).

Confirmation of Cusativin Activity of Pure Enzyme

Aliquots of the concentrated pure protein (2.5 μL, 5 μL, 7 μL) were combined with 1 μL 220 mM ammonium acetate and 200 pmol of an RNA oligonucleotide sequence, AUCACCUCCUUUCU (SEQ ID NO. 13). Autoclaved water was used to dilute the samples to a constant volume of 10 μL. These samples were then incubated for 2 hours at either 37° C. or 50° C., and the absorbance at 260 nm was monitored. Both a blank (autoclaved water and ammonium acetate) and a negative control (autoclaved water, ammonium acetate, and RNA oligonucleotide) were also incubated. Increase in absorbance at $A_{260}$ was attributed to the presence of active enzyme.

Figure 16:
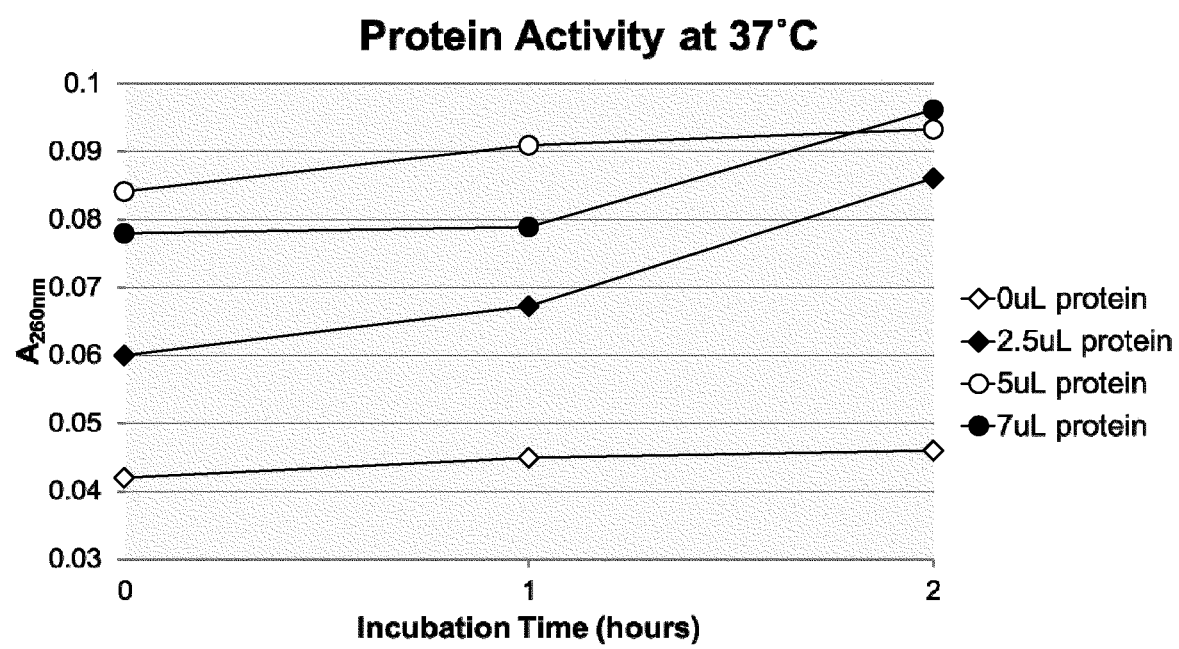
FIG. 16 shows absorbance when using various protein concentrations after incubating the samples for two hours at 37° C.
Figure 17:
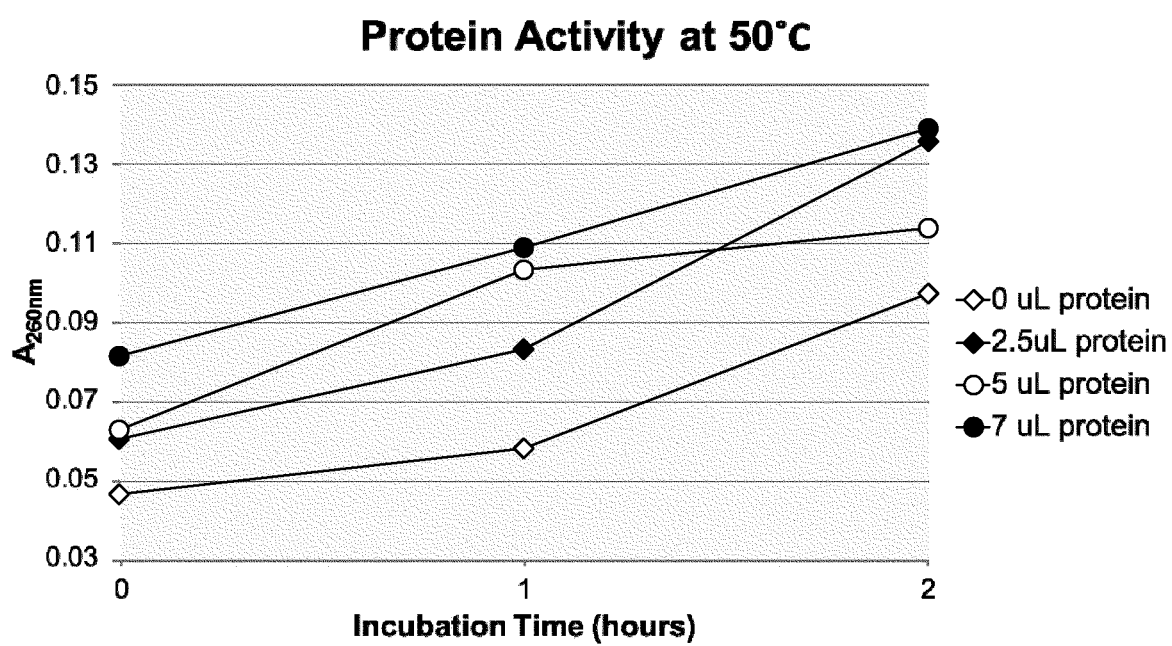
FIG. 17 shows absorbance when using various protein concentrations after incubating the samples for two hours at 50° C.
Figure 18:
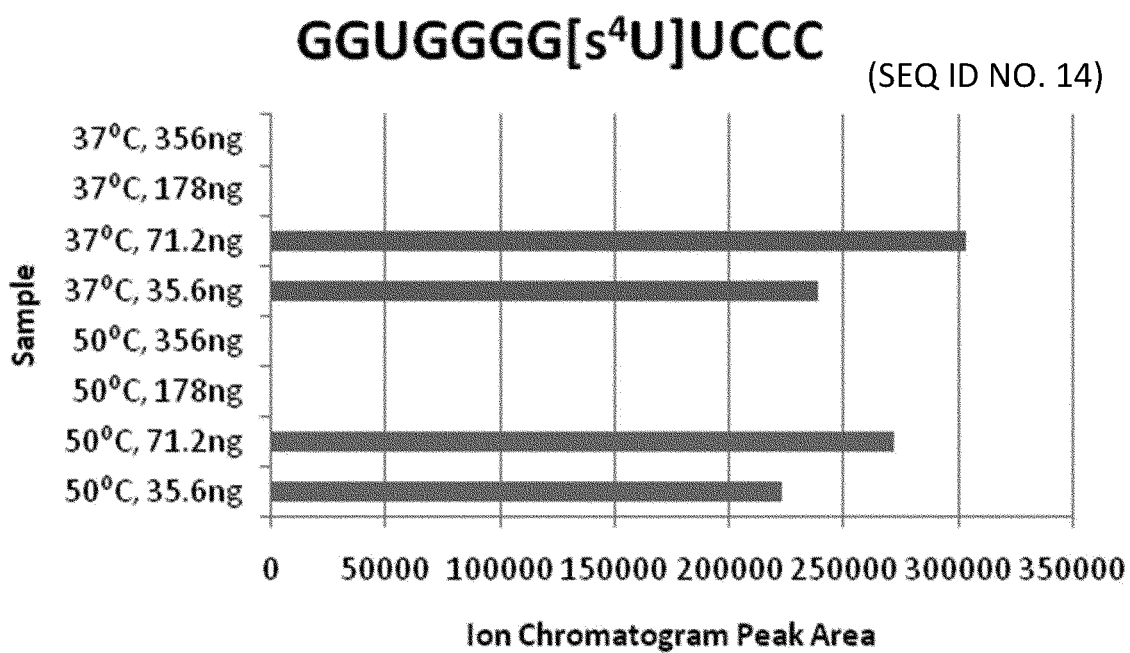
FIG. 18-36 show graphical representations of quantitative data for each digestion product of Cusativin.
Figure 19:
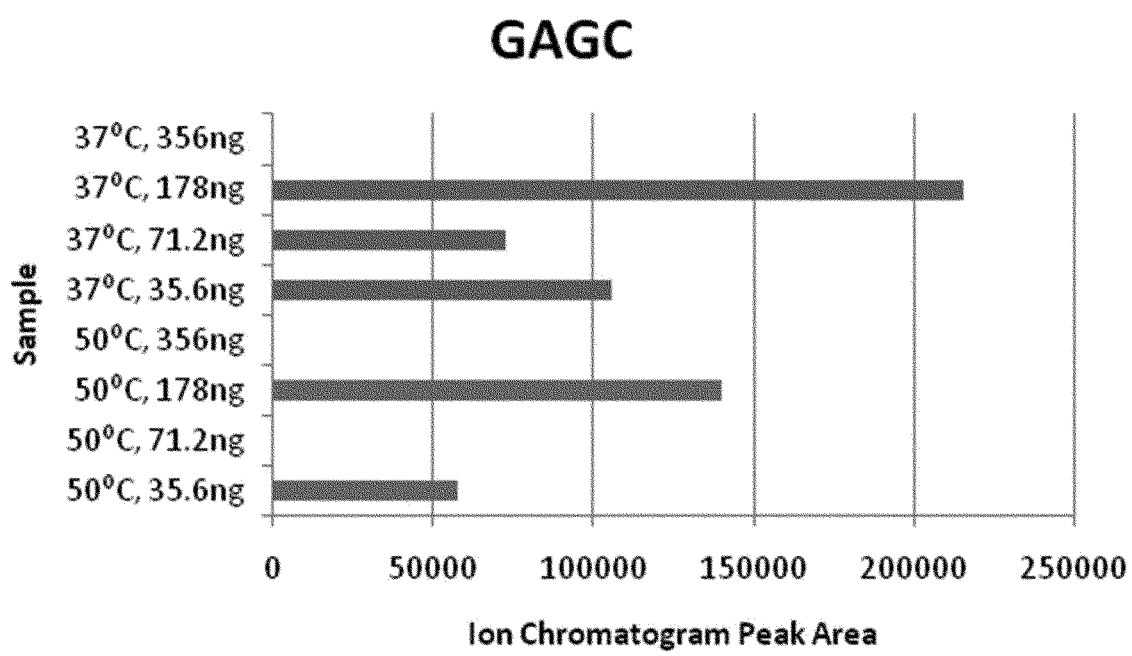
Figure 20:
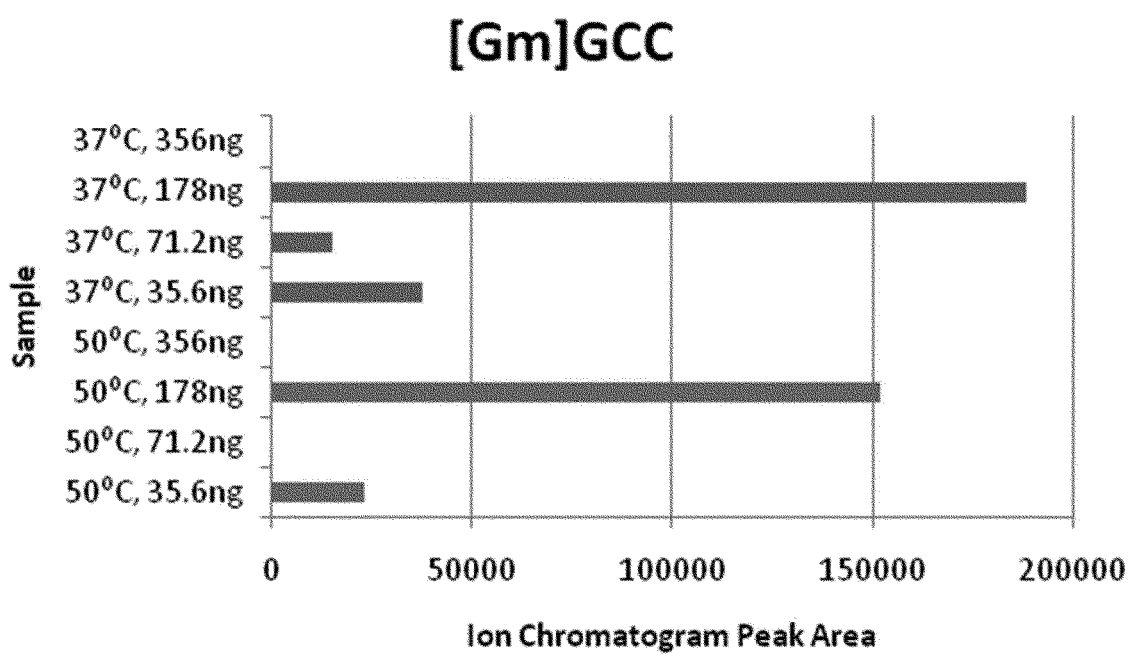
Figure 21:
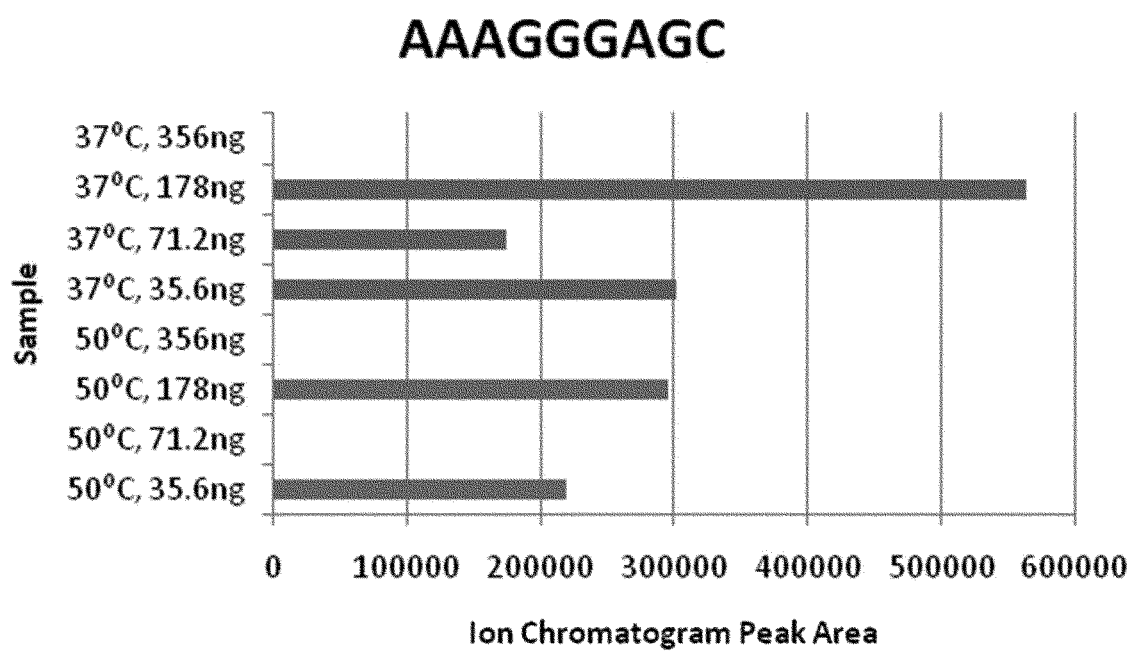
Figure 22:
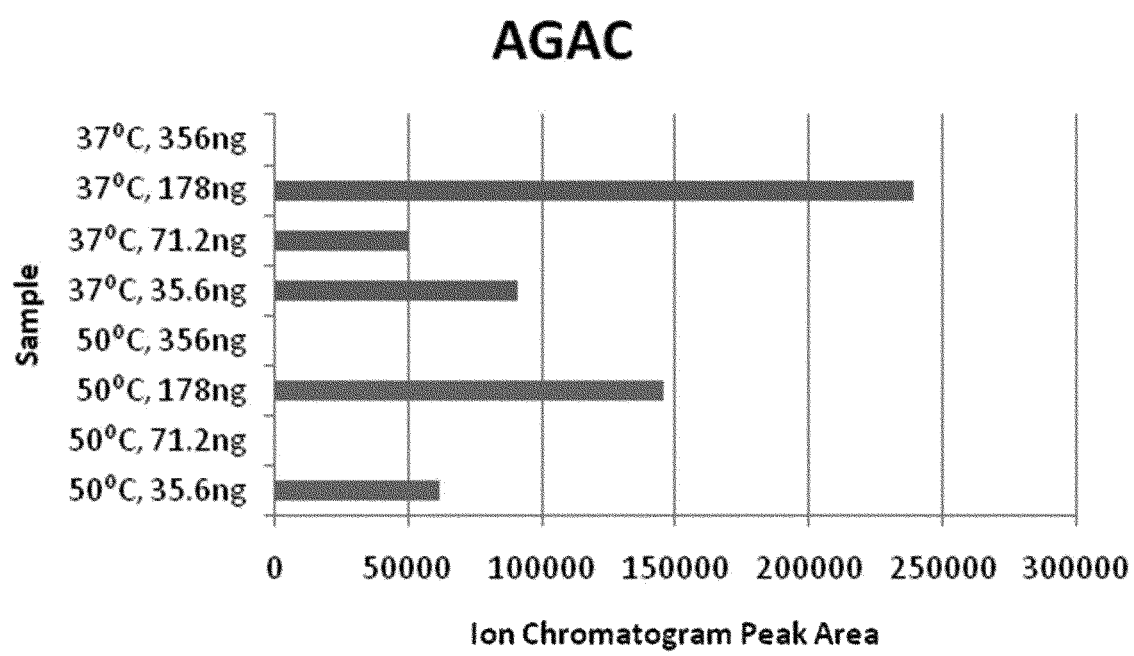
Figure 23:
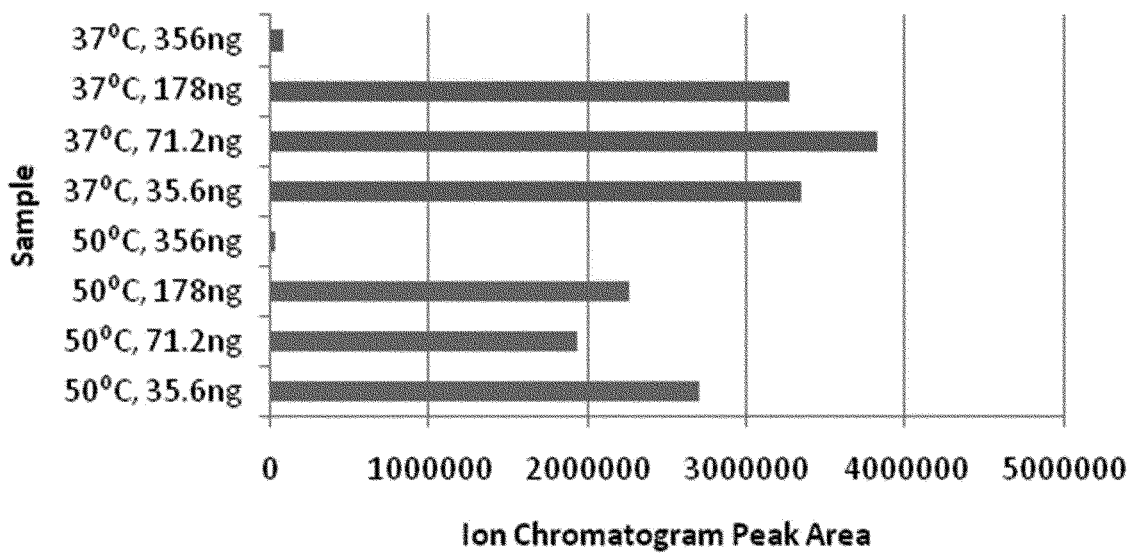
Figure 24:
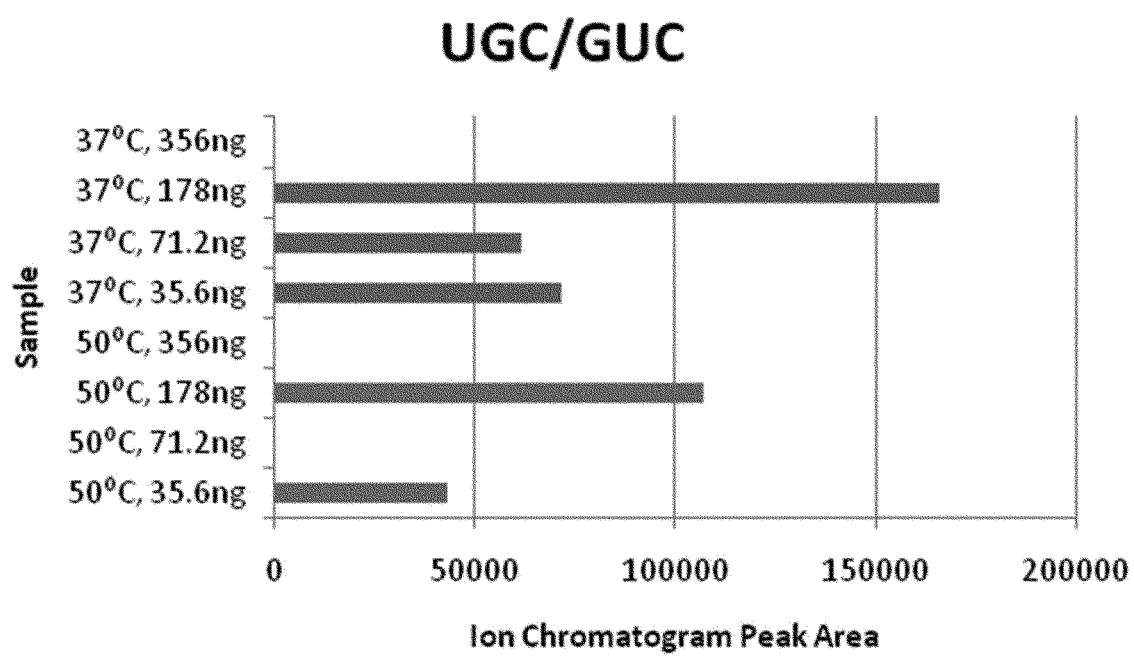
Figure 25:
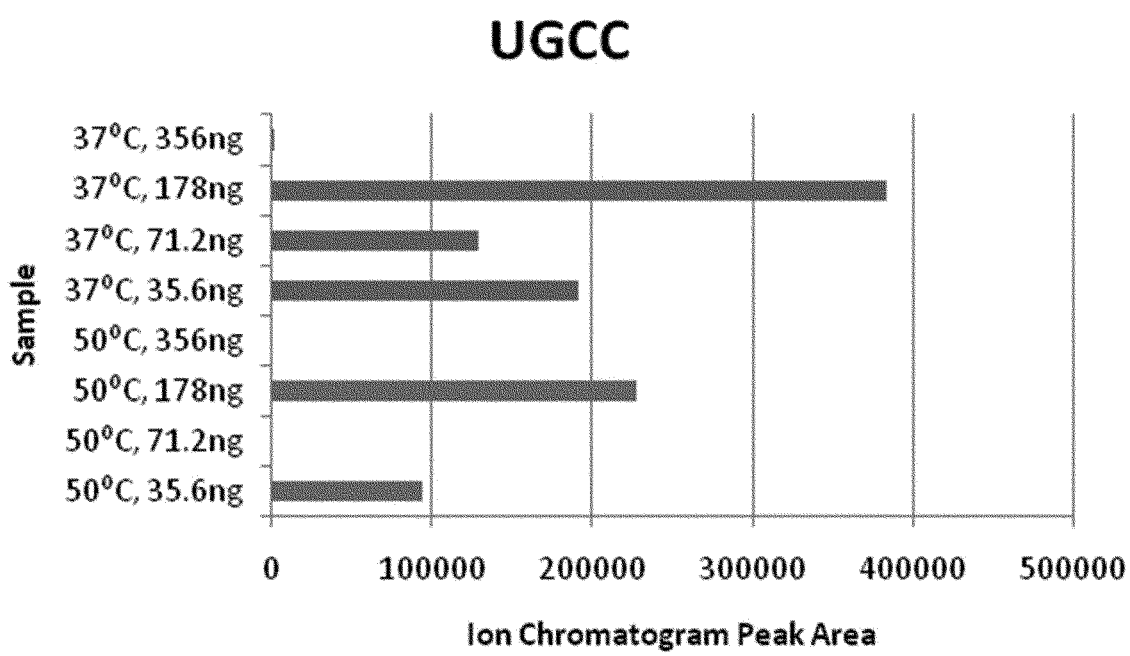
Figure 26:
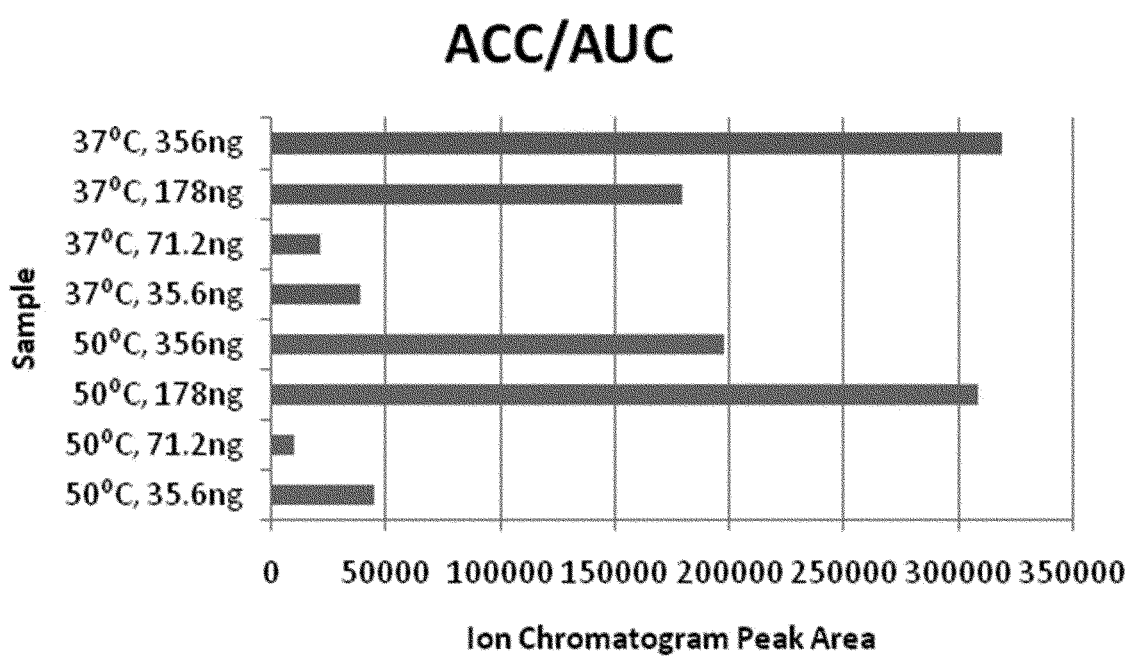
Figure 27:
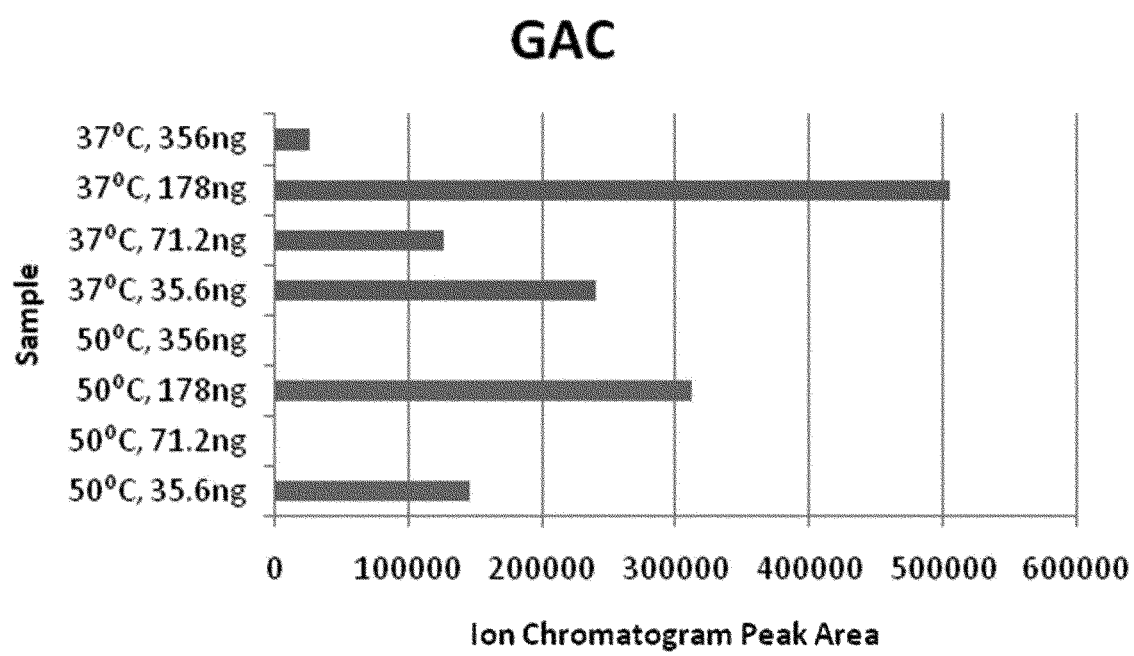
Figure 28:
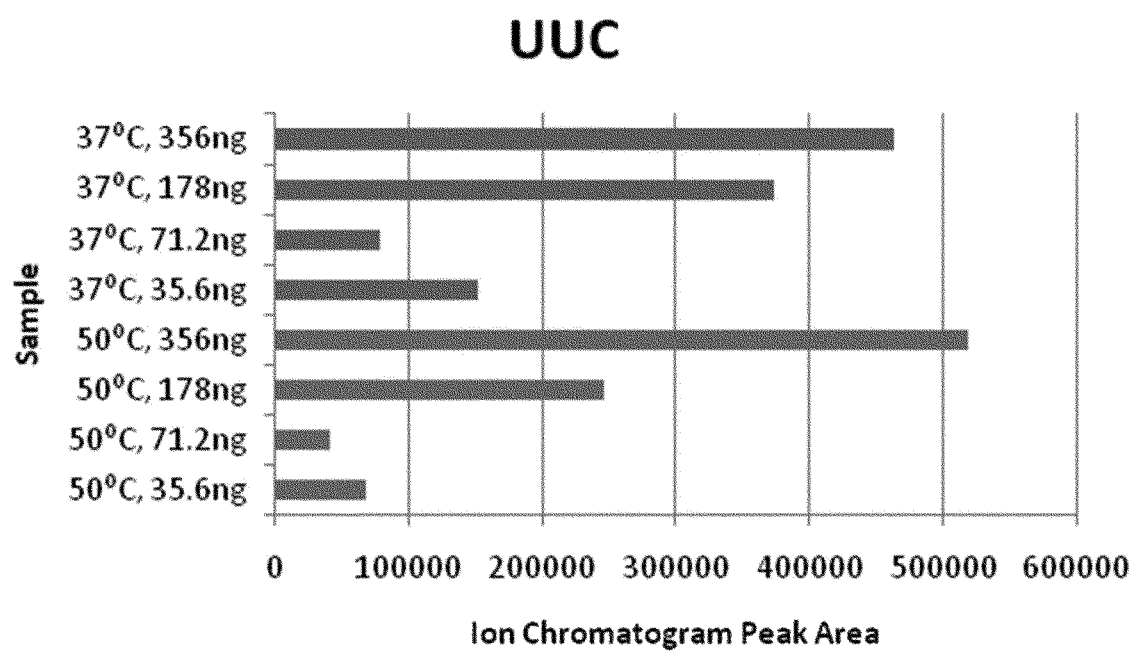
Figure 29:
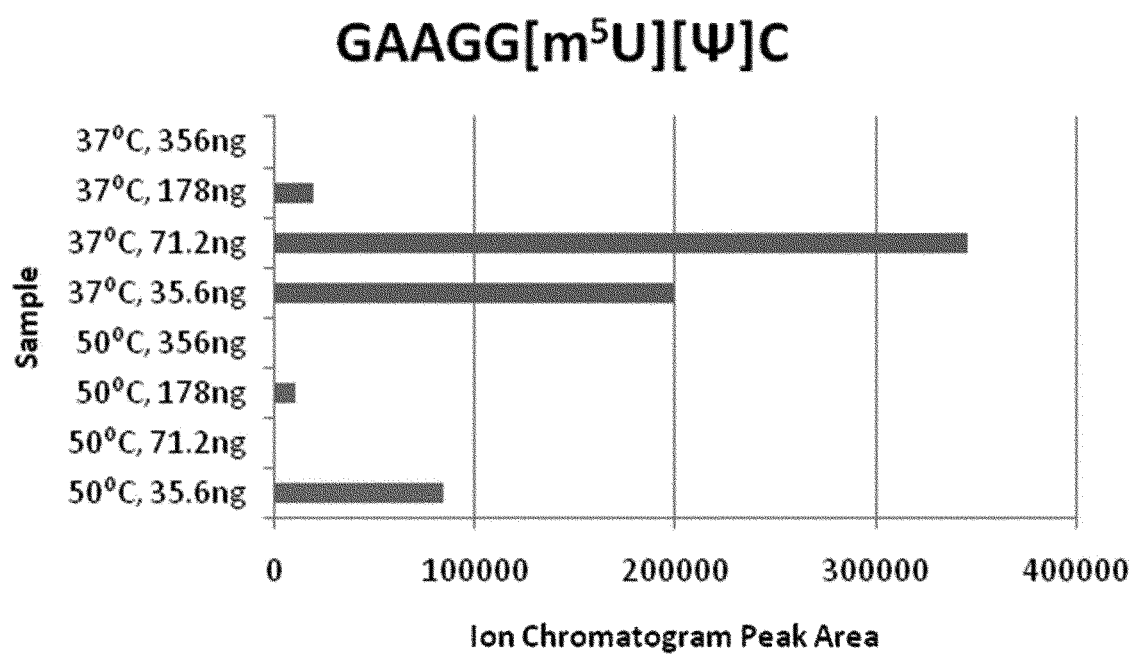
Figure 30:
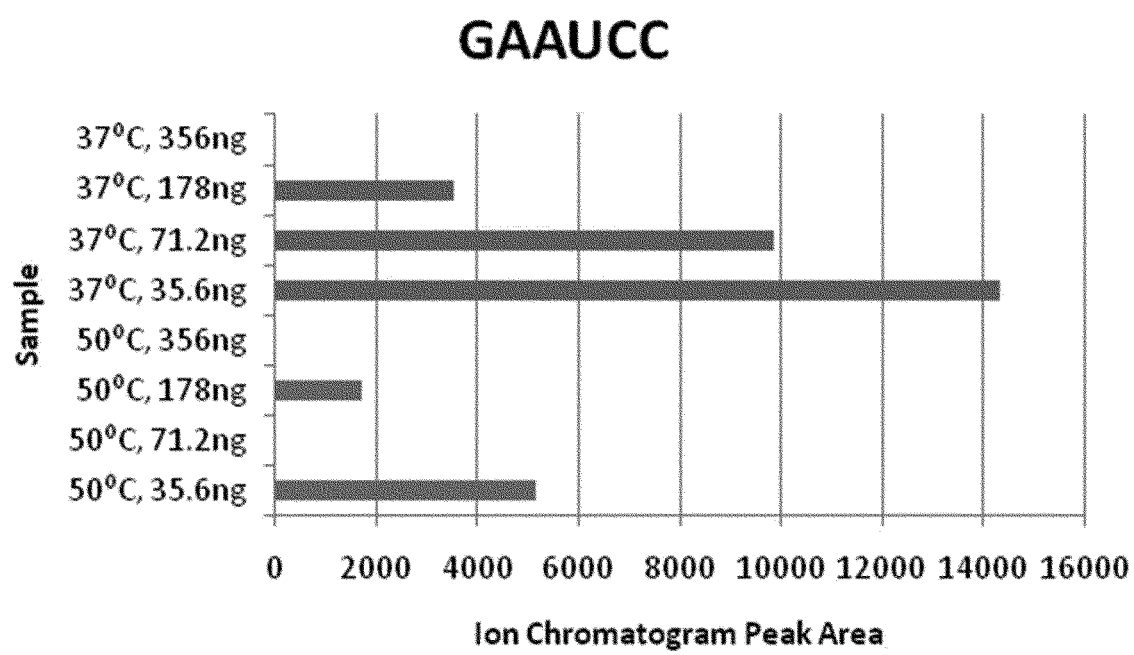
Figure 31:
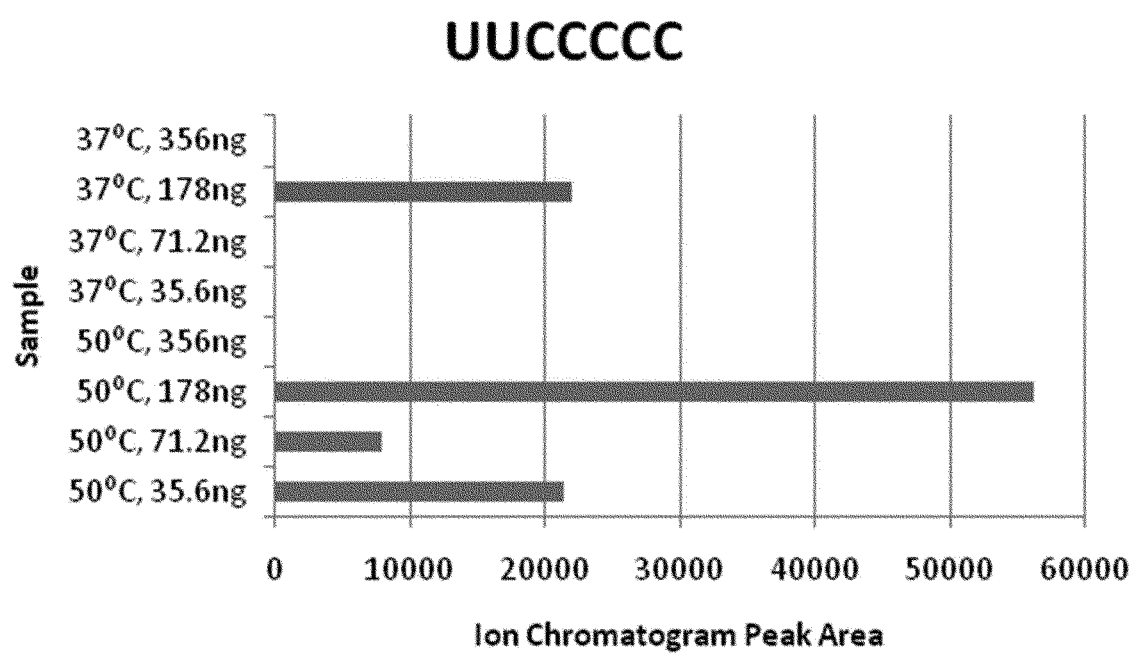
Figure 32:
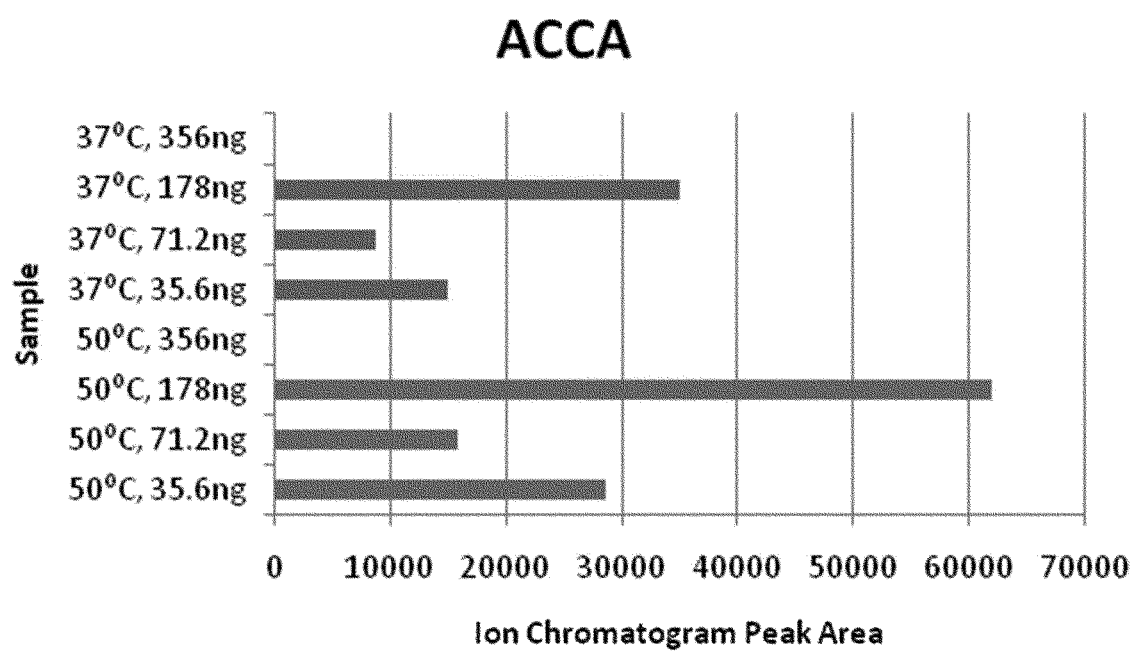
Figure 33:
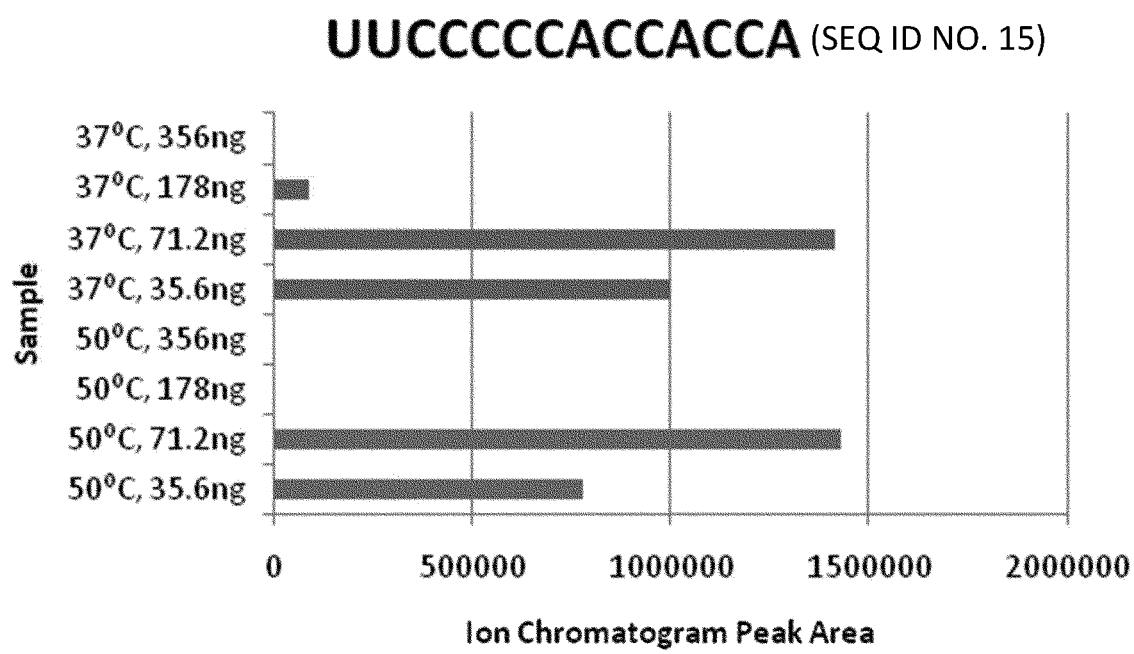
Figure 34:
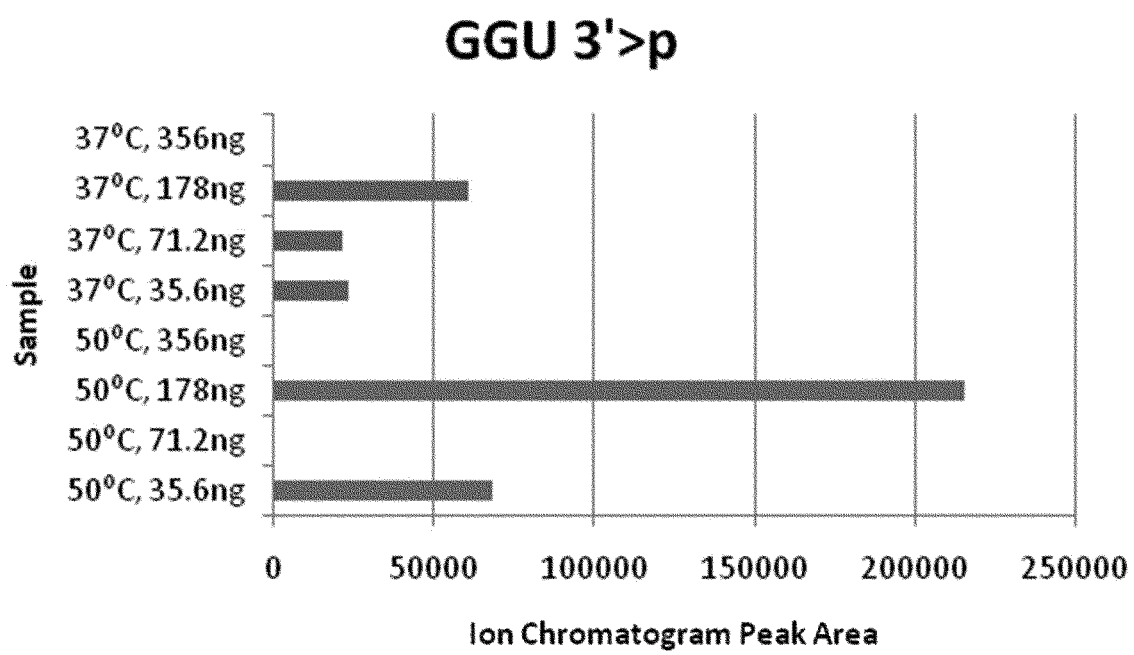
Figure 35:
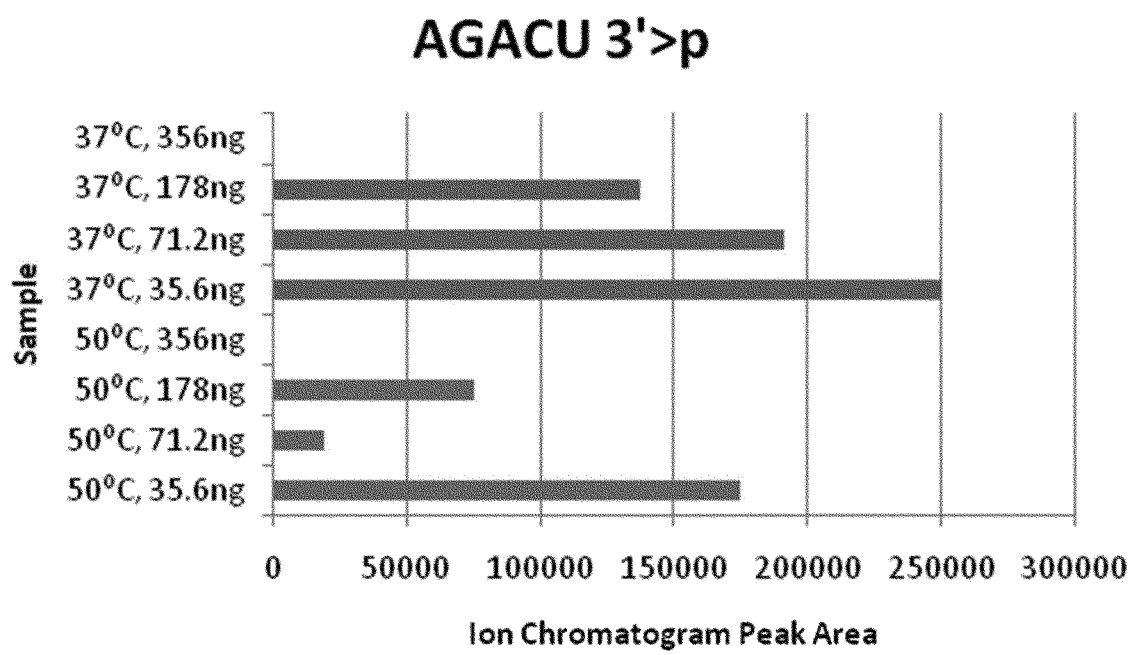
Figure 36:
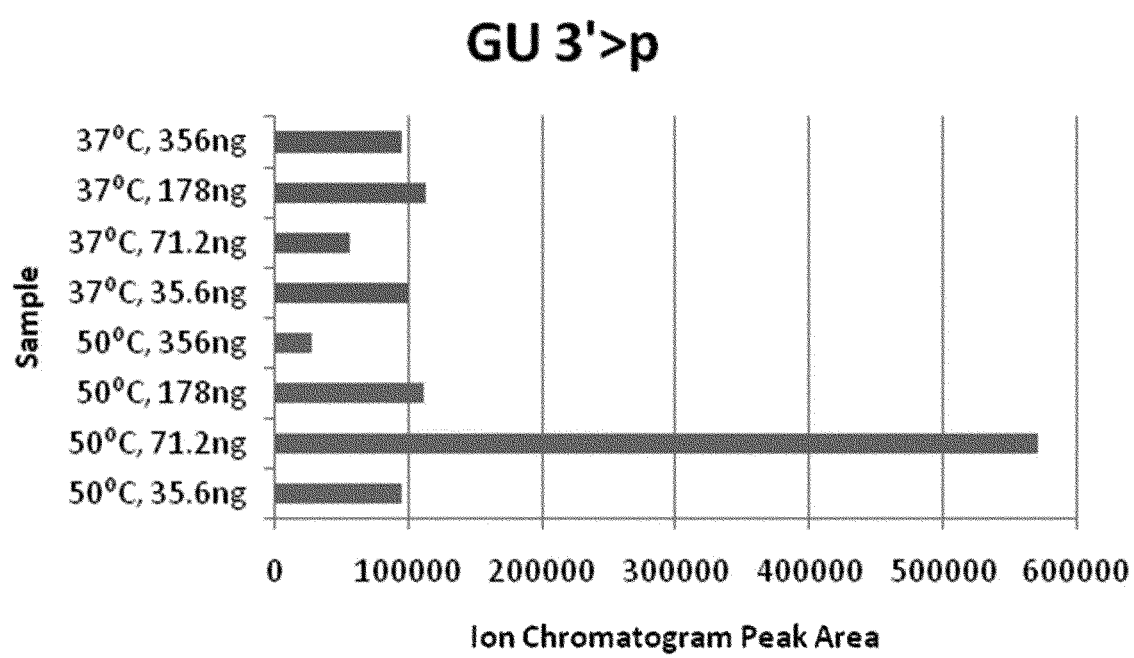

When the general activity assays of the enzyme were initially conducted using Poly (C) and Poly (U), no increase in absorbance was observed after incubation. When activity assays were conducted using the RNA oligonucleotide with the purified (more concentrated) protein, as shown in FIG. 15, significant increases in absorbance were observed when compared to the negative control (0 μL protein), as shown in FIGS. 16 and 17. These increases in absorbance were observed after incubating the samples for two hours both at 37° C. and 50° C. Initial analysis of the digested RNA on LC-MS did not show any digestion products; however, when diluted enzyme was used, digestion products were observed.

Several concentrations of the purified enzyme were incubated with E. coli tRNA$^{Tyr}$ (SEQ ID NO. 7) for 1-2 hours at either 37° C. or 50° C. One μL (~35.6 ng), 2 μL (~71.2 ng), or 5 μL (178 ng) of diluted enzyme (1 μL stock enzyme diluted into 10 μL with water) and 1 μL of undiluted enzyme (356 ng) were incubated with tRNA$^{Tyr}$ at both temperatures. The tRNA$^{Tyr}$ digestion products were then analyzed by IP-RP-LC-MS/MS. Mass-to-charge (m/z) values of theoretically expected digestion products based on assumed cytidine-specific cleavage of RNA and their product ions following CID of digestion product precursor ions were computed by Mongo Oligo Mass Calculator (http://mods.rna.albany.edu/masspec/Mongo-Oligo).

Because the modified nucleotide sequence of tRNA$^{Tyr}$ is known, the theoretical digestion products of tRNA$^{Tyr}$ were compiled for CpN bond cleavage, and the raw MS data was initially searched for the respective m/z of digestion product precursor ions. The nucleotide sequence of these precursor ions was further confirmed by CID where the presence of sequence-informative product ions was scored. Additionally, digestion products resulting from cleavages at other nucleobases were also assessed to evaluate the specific cleavage of RNA by Cusativin enzyme. This was necessary because of the known occasional cleavage of RNA at certain uridines by Cusativin. The digestion products found in this study following incubation of tRNA$^{Tyr}$ with 1 μL of the diluted protein (~36 ng) are shown in Table 2. Each of these digestion products found with 36 ng of enzyme was also searched for their presence in other samples, where different amounts of purified protein were used. The ion chromatogram peaks for each of the digestion product precursor ions were integrated using Xcalibur software. Graphical representations of this quantitative data for each digestion product are shown in FIGS. 18-36. 3'-linear phosphates were found on all of the cytidine-specific products, while only 3'-cyclic phosphates were found on the uridine specific products.

TABLE 2

| C-specific - No Missed Cleavages | C-specific - Missed Cleavages | U-specific - Low Abundance |
|---|---|---|
| GAGC | GGUGGGG[s⁴U]UCCC (SEQ ID NO. 14) | GGU 3' > p |
| AAAGGGAGC | | |
| AGAC | [Gm]GCC | AGACU 3' > p |
| U[Q]UA[ms²i⁶A]A[Ψ]C | UGCC | GU 3' > p |
| UGC/GUC | GAAUCC | |
| GUC | UUCCCCC | |
| AUC | ACC | |
| GAC | ACCA | |
| UUC | UUCCCCCACCACCA (SEQ ID NO. 15) | |
| GAAGG[m⁵U][Ψ]C | | |

Design of Synthetic Gene, Amplification, and Purification

The purified protein was digested with Trypsin. The tryptic peptides identified by LC-MS analysis of Cusativin following treatment with proteolytic enzyme trypsin are shown in Table 3. Tryptic peptides for two other small seed coat proteins were also found. The first two peptides listed in the table were previously known in the literature. The amino acid sequences of a portion of the tryptic peptides were blasted against Cucumis sativus protein database (GCF_0000040752_ASM407V2_protein.faa) using Protein Lynx (Waters) to identify the predicted polypeptide as an RNase MC-like protein.

TABLE 3

| Tryptic Peptides in Our Study | Tryptic Peptides from Literature |
|---|---|
| SFTIHGLWPQK (SEQ ID NO. 16) | SFTIHGLWPNK (SEQ ID NO. 16) |
| YFQTAINMR (SEQ ID NO. 17) | YFQTAINMR (SEQ ID NO. 17) |

TABLE 3-continued

| Tryptic Peptides in Our Study | Tryptic Peptides from Literature |
|---|---|
| HGIDLLSVLR (SEQ ID NO. 18) | PPXGHEXNK (SEQ ID NO. 19) |
| | IAHLENDLNVVWPNVVTGNNK (SEQ ID NO. 20) |
| | YVGR (SEQ ID NO. 21) |
| | ASNGQVLLTEIVMXFDDDXXTL (SEQ ID NO. 22) |

A conserved domain architecture search on the NCBI database shows that Cusativin is a T2-type RNase. Similar results were obtained through the use of InterPro (http://www.ebi.ac.uk/interpro/).

A synthetic gene with modified codons was designed based on the identified amino acid sequence so as to enable enhanced protein expression in E. coli, as provided in SEQ ID NO. 4. Restriction sites were added to both ends to enable cloning into the protein expression vector, pET 22b (Novagen). The synthetic DNA (651 bp) was made as gene block by IDT DNA technologies.

The gene was amplified via PCR. 5 μL 10×PCR buffer, 1 μL dNTPs, 0.5 μL synthetic DNA template, and 0.6 μL PfuTurbo DNA Polymerase were combined. Additionally, to the mixture were added 0.5 μL each of the forward and reverse primers, ATGGAAAAATGGAAAAGAC-CAAAAGTGTCGATG (SEQ ID NO. 23), and AAAAATAAATGAGCCTGCGCAATTGG (SEQ ID NO. 24), respectively, which also have sequences for BglII and HindIII for restriction endonucleases at 5'- and 3'-ends, respectively. The primer concentration was 100 pmol/μL. These primers enabled easy amplification of the gene sequence in this exemplary system, but other primers may be used in other embodiments of this invention. The resulting mixture was diluted with water to a total volume of 50 μL. A total of three samples were prepared and subjected to the following PCR cycle: 94° C. for 2 minutes, 92° C. for 0.5 min, 35 cycles of 57° C. for 0.5 min and 72° C. for 2 min, and one cycle of 72° C. for 5 min Agarose gel (1.0%) electrophoresis was performed to verify the size of the PCR product.

Figure 37:
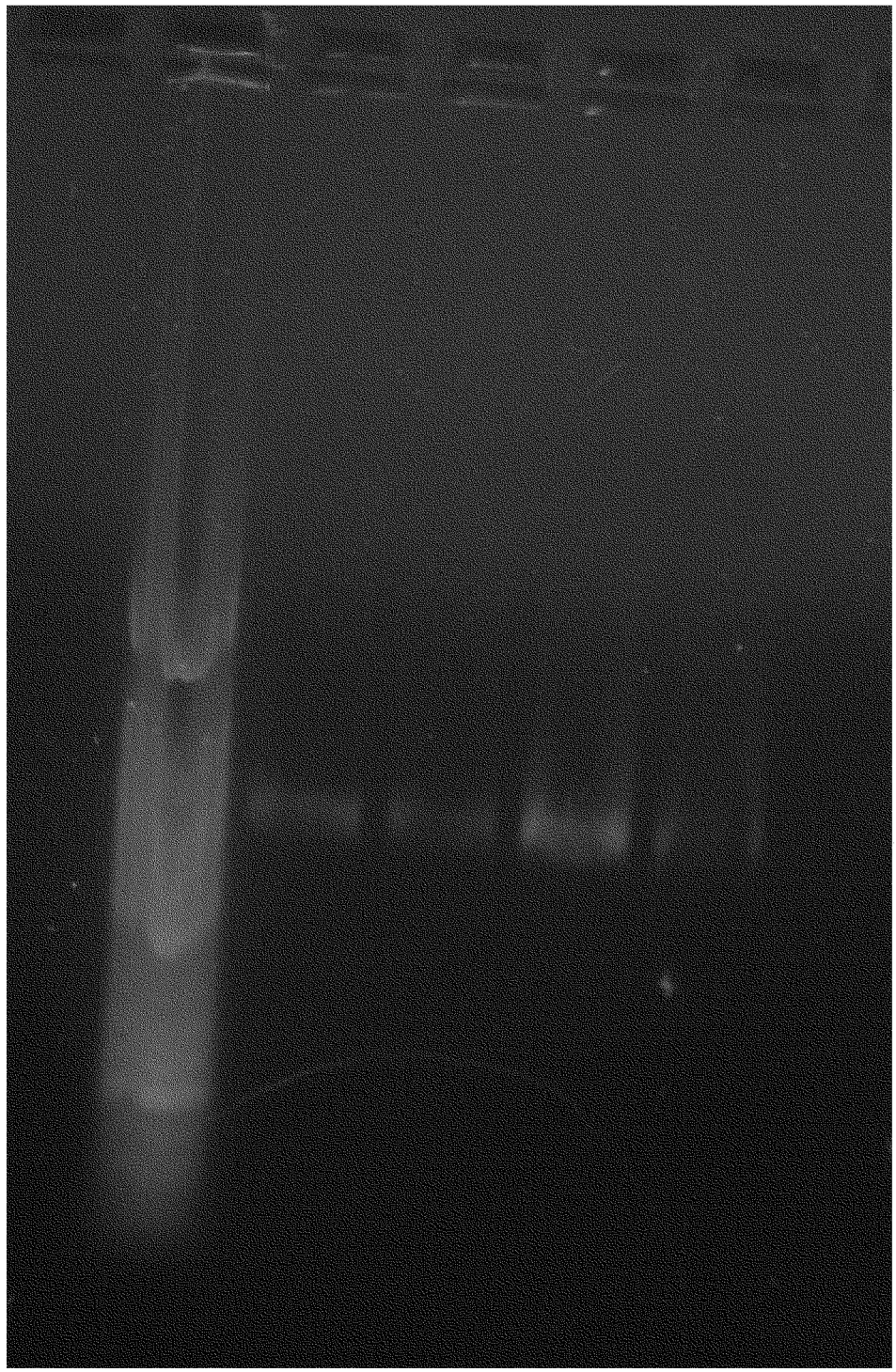
FIG. 37 shows an agarose gel used to monitor the amplification of the synthetic gene.
Figure 38:
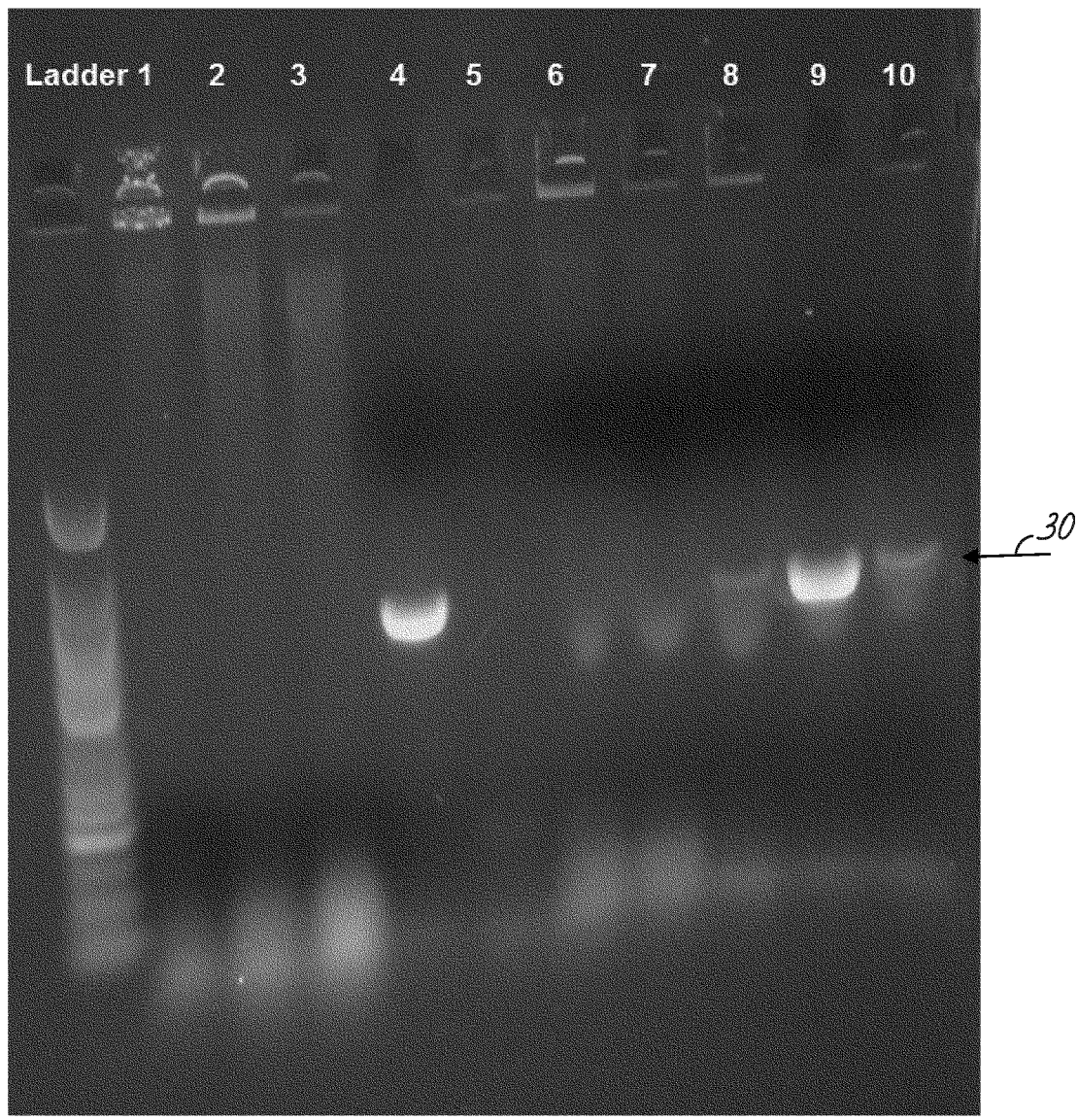
FIG. 38 shows an agarose gel used to monitor the presence of recombinant plasmids in *E. coli*.

The amplified gene was purified using the QIAquick PCR Purification Kit (spin protocol). A 1.0% agarose gel was used to check the success of the purification, as shown in FIGS. 37 and 38 (indicated at arrow 30 of FIG. 38).

The gene was digested using restriction enzymes BglII and HindIII. The following 50 μL reaction mixture was incubated at 37° C. for 2 hours: 15 μL DNA, 5 μL NEB 2.1 Buffer, 1.5 μL BglII, 1 μL HindIII. Additionally, a second experiment was performed using 10 μL DNA. The digested DNA was purified using the QIAquick PCR Purification Kit (spin protocol).

The purified gene was ligated into a pET-22b(+) vector. The vector had previously been digested with BamHI and HindIII. The ligation reaction mixture was as follows: 9.5 μL DI water, 2 μL 10× ligase buffer, 2 μL pET-22b(+) vector, 6 μl of the digested gene, and 0.5 μL of ligase. This reaction mixture was kept at room temperature for 1 hour, and then chilled at 4° C. for about 5 days.

The ligation mixture was then transformed into BL21 E. coli cells. 10 μL of the ligation mixture was added to two different 1.5 mL tubes of the BL21 E. coli cells and vortexed. The tubes were then put on ice for 30 minutes, incubated at 42° C. for 2 min, and then put back on ice for 2 min 200 μL SOC media was added to each tube, which were then incubated and agitated at 37° C. for 1 hour and 10 minutes. The transformed cells were then plated on LB+amp plates. The plates were then allowed to sit at room temperature for 15 min prior to being placed in the 37° C. incubator overnight.

Following overnight incubation, 10 colonies were collected from the plate. The colonies were collected by stabbing an autoclaved pipet tip into the colony. This tip was then rubbed onto the bottom of a PCR tube and then dropped into a test tube containing 1 mL of LB media with 0.05 μg/mL ampicillin. The test tubes were incubated overnight at 250 rpm and at 37° C. 38 μL of PCR mixture (similar to the mixture used for amplification of the gene, with the colony substituted as the template) was added to each PCR tube. The colonies were then subjected to the following PCR cycle: 2 min at 94° C., 0.5 min at 92° C., 30 cycles of 0.5 min at 57° C. followed by 2 min at 72° C., and finally 5 min at 72° C. A 1.0% agarose gel of the PCR products was performed to visualize which colonies contained the gene.

To the colonies containing the gene were added 10 mL of LB media supplemented with 0.05 mg/mL ampicillin. These cultures were incubated at 37° C. on a shaker (Innova) overnight. Experiments were conducted with other media, including terrific broth, and autoinduction was also tried.

0.5 mL of each colony was placed in 0.5 mL 65% glycerol and put in the deepfreeze to serve as future culture stock. The remaining cultures of each colony were pelleted. Pelleting was performed using 1.5 mL Eppendorf tubes centrifuged for 1 min at 6700 rpm. The supernatant was then discarded. Additional cell culture was added to the tube and spun down. This pelleting procedure was repeated until all of the cell culture had been pelleted. The plasmids were purified from the pellets using a Qiagen miniprep kit.

Figure 39:
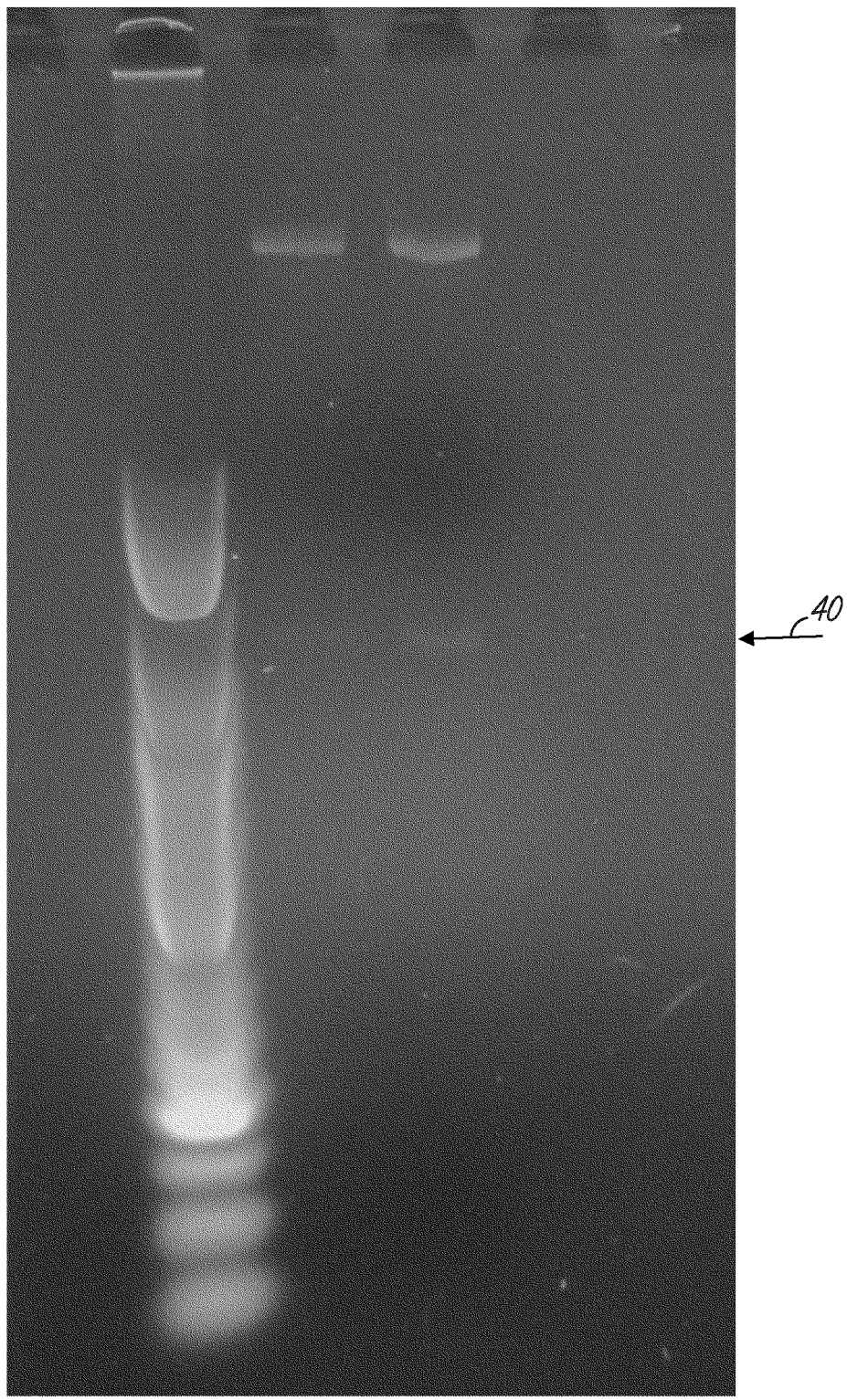
FIG. 39 shows an agarose gel used to visualize if recombinant plasmid digestion had successfully showed the presence of insert.

The purified plasmids were then digested using the following recipe: 5 μL plasmid, 5 μL NEB buffer 2.1, 1.5 μL BglII, 1 μL HindIII, and 37.5 μL water. The reaction mixtures were incubated for two hours at 37° C. and run on a 1.0% agarose gel to visualize if the digest had been successful, as shown in FIG. 39 (indicated at arrow 40).

Figure 40:
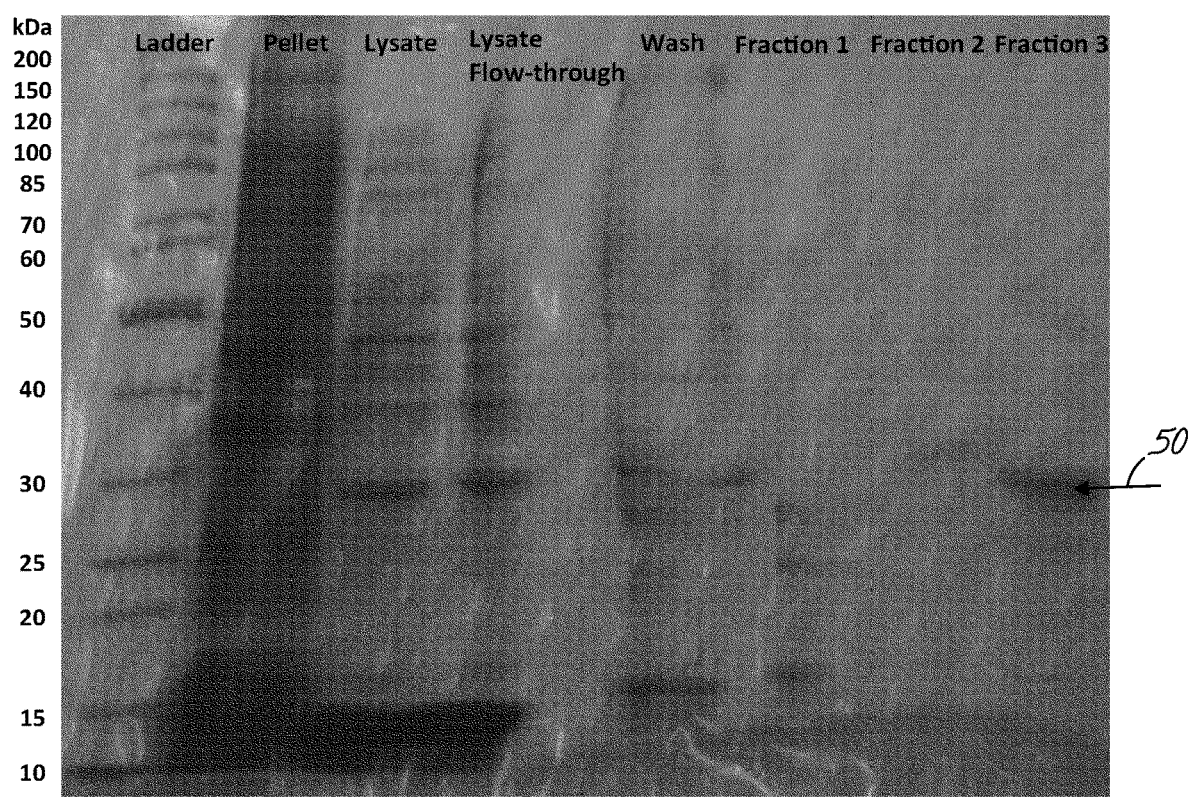
FIG. 40 shows the SDS-PAGE gel for the column fractions collected from one colony of Cusativin-producing *E. coli*.
Figure 41:
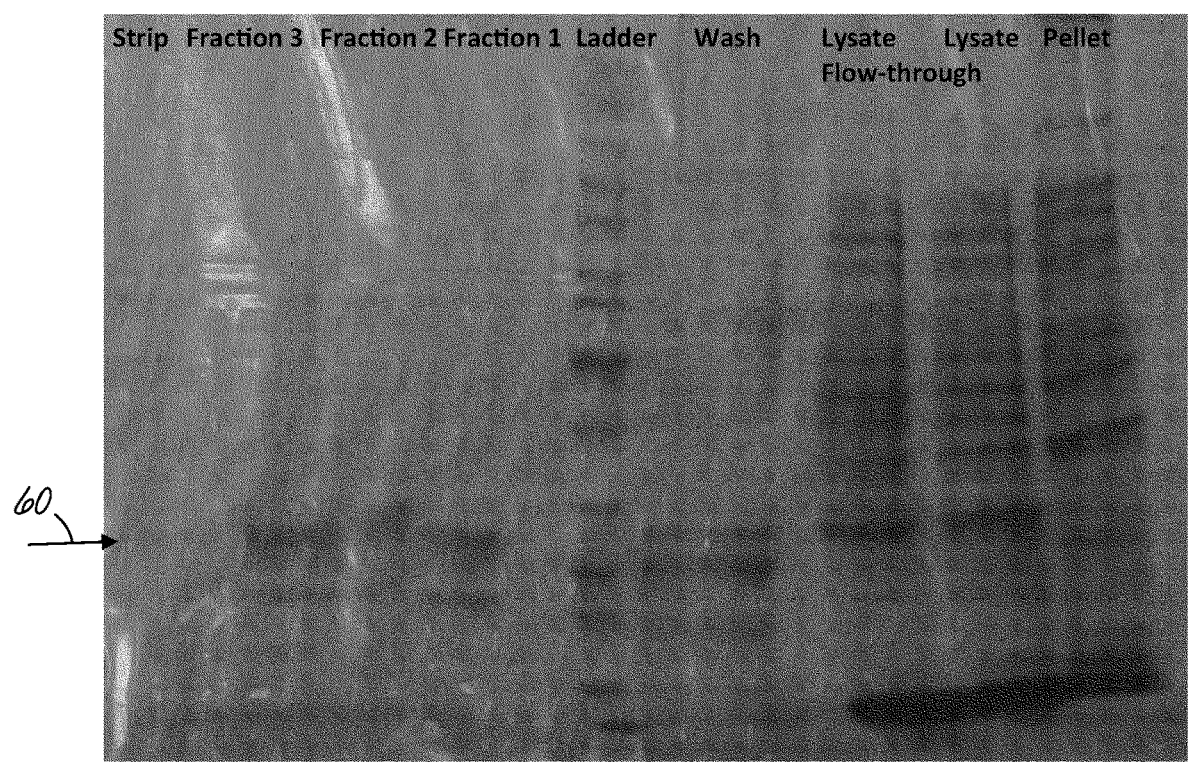
FIG. 41 shows the SDS-PAGE gel for the column fractions collected from another colony of Cusativin-producing *E. coli*.

The purified plasmids were then prepared for sequencing. The sequencing data confirmed that the purified plasmids were the pET-22b(+) vector with the inserted Cusativin gene. The stock colonies (in the deepfreeze) containing these correct plasmids were then cultured in 500 mL LB media containing 0.05 mg/mL ampicillin. The cells were induced to produce the recombinant enzyme by adding IPTG to the culture. His-tag column chromatography was used to purify the protein from the cells following overexpression. Table 4 shows the protein content in each elution fraction as determined by Bradford Assay. Based on this data it was found that each 500 mL culture yielded approximately 34 μg of target protein total in the three elution fractions combined. FIGS. 40 and 41 show the SDS-PAGE gels for the column fractions collected from each clone (at least 5 μg protein were loaded in each lane). All three elution fractions in each purification were found to contain target protein (indicated at arrow 50 in FIG. 40 and arrow 60 in FIG. 41), so they were all concentrated and used for activity assays.

TABLE 4

| Fraction # (Total Volume) | Clone 4 | Clone 9 |
|---|---|---|
| Fraction 1 (500 μL) | 0.5 μg in 50 μL | 0.5 μg in 50 μL |
| Fraction 2 (950 μL) | 1 μg in 50 μL | 1 μg in 50 μL |
| Fraction 3 (500 μL) | 1 μg in 50 μL | 1 μg in 50 μL |

To prepare the lysate, 2 mg of lysozyme was added for each mL of cell suspension. The suspensions were then chilled at 4° C. for 30 min. Following incubation at 4° C., the suspensions were centrifuged for 30 min at 15000 rpm. The supernatant was then filtered through 0.45 µm Durapore filters. The filtered supernatant was loaded onto the charged nickel column three times. The column was then washed with 10 column volumes 1× bind buffer and then washed with 5 column volumes 1× wash buffer. The recombinant enzyme was eluted in three fractions. The first fraction was 500 µL elute buffer, the second fraction was 750 µL elute buffer (loaded on column twice) plus an additional 200 µL elute buffer, and the third fraction was 500 µL elute buffer. The column was then stripped with 6 column volumes 1× strip buffer. Bradford Assay was used to determine the protein concentration of each fraction, and at least 5 µg of protein for each fraction were analyzed by SDS-PAGE to check for presence of the 23-25 kDa protein. Protein elution fractions from each clone were concentrated and desalted with water using Amicon Ultra-5 Centrifugal filter devices (size=3 k).

Characterization of Recombinant Cusativin for Mapping Nucleoside

Modifications

The activity of the enzyme was tested by incubating aliquots of protein with RNA and checking the $A_{260}$. The activity assay was performed using 1 µL of a 1:10 dilution of the concentrated protein, 1 µL concentrated protein, 2 µL concentrated protein, and 5 µL concentrated protein. Each sample had a total volume of 10 µL and contained 200 pmol RNA oligonucleotide sequence, AUCACCUCCUUUCU (SEQ ID NO. 13), and 1 µL 220 mM ammonium acetate. The blank contained no protein or RNA, and the negative control contained no protein. The samples were incubated at both 37° C. and 50° C., and the absorbance was checked using the Nanodrop.

1 µL concentrated protein and 1 µL of a 1:10 protein dilution did not show any increase in $A_{260}$ following incubation with RNA oligonucleotide. However, when 2 µL (0.02 µg) and 5 µL (0.1 µg) of concentrated protein were used, the absorbance did increase. These increases in absorbance are shown in FIGS. 42 and 43.

Figure 44:
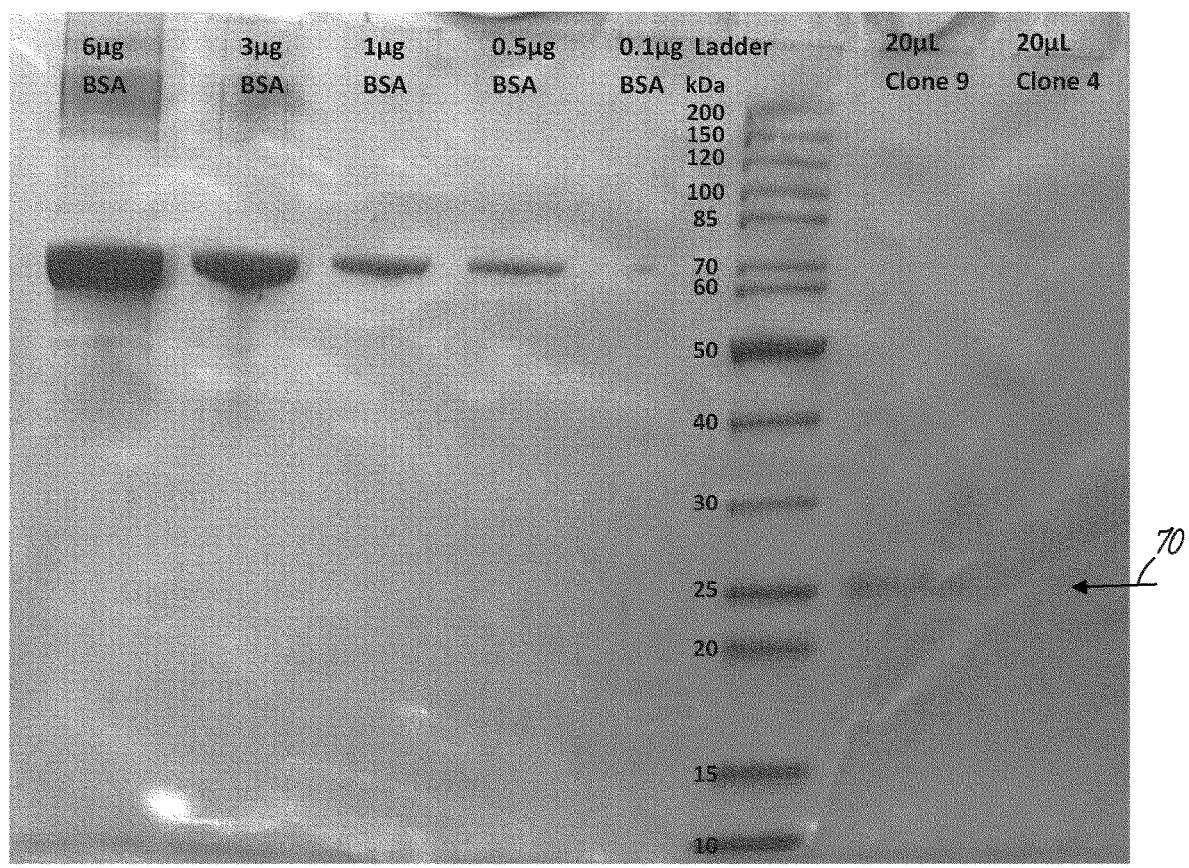
FIG. 44 is an SDS-PAGE to show the relative amount of purified Cusativin from two colonies of Cusativin-producing *E. coli*.

SDS-PAGE was used to approximate the amount of protein contained in the concentrated fractions. One gel was run with 1 µL and 5 µL of the protein concentrated from each clone. Another gel was run with 20 µL of the protein from each clone. Each gel also had lanes where 0.1 µg BSA, 0.5 µg BSA, 1 µg BSA, 3 µg BSA, and 6 µg BSA were run. As shown in FIG. 44, the concentrated clone 9 elution fractions contained approximately 0.2 µg protein in 20 µL, while the concentrated clone 4 elution fractions contained much less protein (indicated at arrow 70). Each concentrated protein sample had a total volume of approximately 100 µL.

The RNA digestions were prepared by placing 3 µL tRNA$^{Tyr}$ into an Eppendorf tube for each digestion. The tRNA was then incubated at 95° C. for 2 min, followed by 2 min at 4° C. Then, 10 µL of 220 mM ammonium acetate and a designated amount of protein (5 µL concentrated, 1 µL 1:5 dilution, 1 µL 1:10 dilution, and 1 µL 1:20 dilution) were added to each sample. The samples were then incubated for 2 hours and dried in the SpeedVac.

Figure 42:
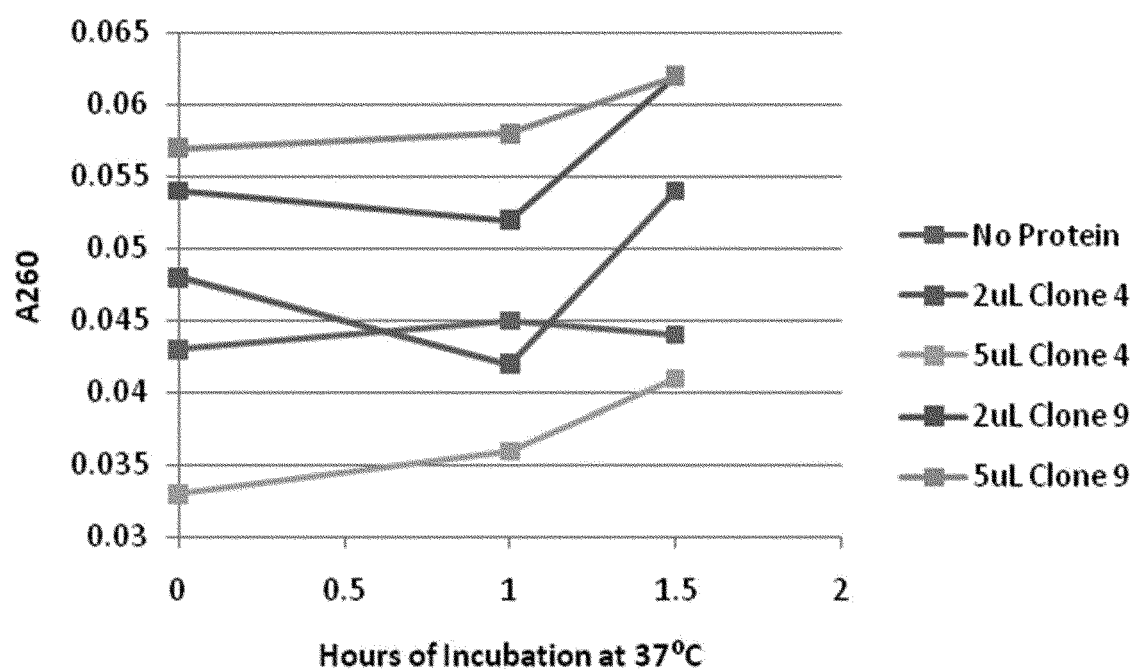
FIG. 42 shows absorbance when using various protein concentrations after incubating the samples for two hours at 37° C.
Figure 43:
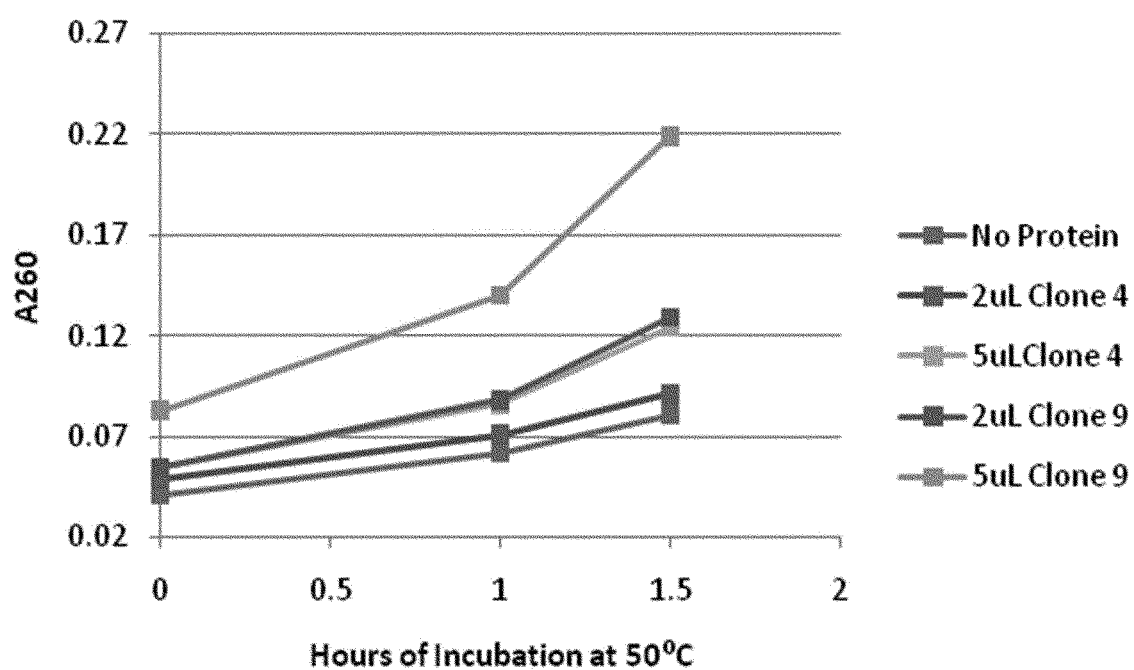
FIG. 43 shows absorbance when using various protein concentrations after incubating the samples for two hours at 50° C.

As shown in FIGS. 42 and 43, the recombinant enzyme did exhibit RNase activity. The slight increases in $A_{260}$ observed are very similar to the activity observed with the enzyme purified from the seeds (FIGS. 16 and 17).

Figure 45:
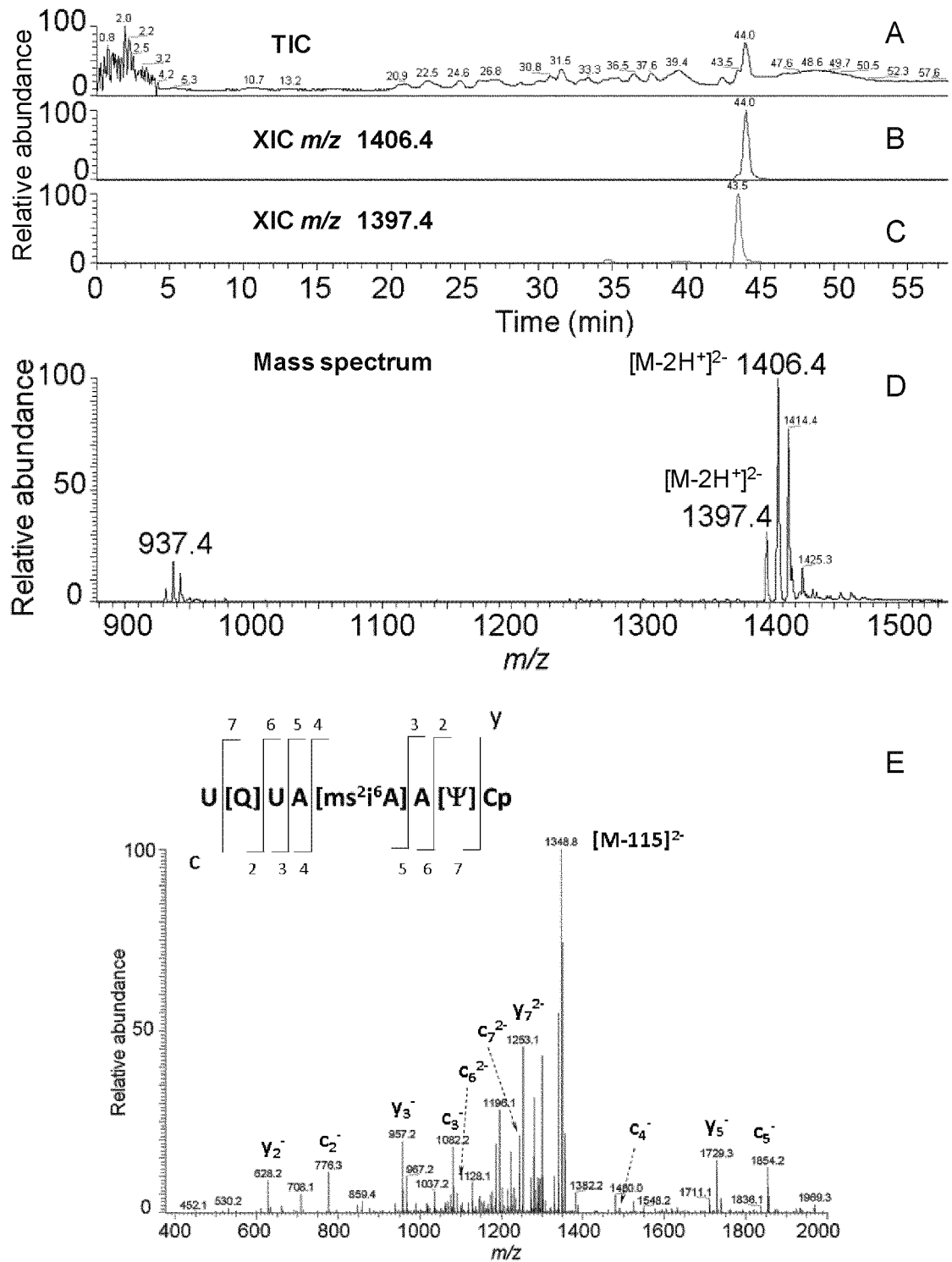
FIG. 45 shows an LC-MS analysis of Cusativin digestion product.

FIG. 45 shows an LC-MS analysis of Cusativin digestion product, U[Q]UA[ms$^2$i$^6$A]A[Ψ]C, from tRNA$^{Tyr}$. The recombinant protein (0.1 µg) was used to digest E. coli tRNATyr (2 µg) and analyzed by LC-MS. In FIG. 45, (A) is the TIC of all the digestion product precursor ions observed in the analysis, (B) is the XIC for m/z 1406.4, corresponding to the linear phosphate of U[Q]UA[ms$^2$i$^6$A]A[Ψ]C, (C) is the XIC for m/z 1397.4, corresponding to the 2',3'-cyclic phosphate, (D) is an MS depicting the multiply charged ions, and (E) is the CID-based sequencing of U[Q]UA[ms$^2$i$^6$A]A[Ψ]C with a 3'-phosphate. Sequence informative product ions ($c_n$ having a common 5'-end and $y_n$, having a common 3'-end) from which the sequence is reconstructed are labeled on the spectrum.

Figure 46:
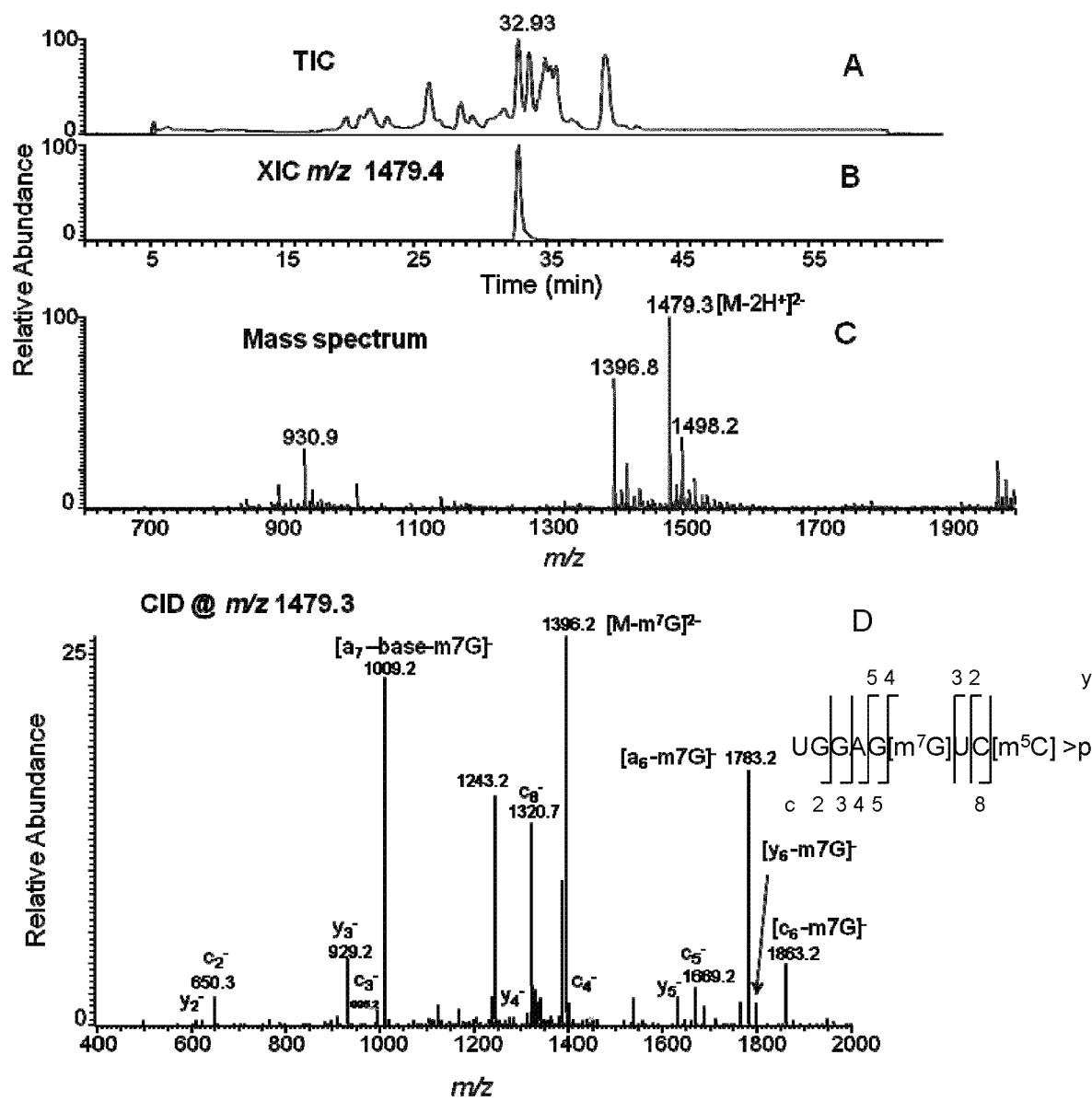
FIG. 46 shows an LC-MS analysis of Cusativin digestion product.

Additionally, Cusativin cleaves RNA at modified cytidines unlike RNase MC1. FIG. 46 provides the LC-MS analysis of Cusativin digestion product, UGGAA[m$^7$G]UC[m5C]>p, from yeast tRNA$^{Phe}$. In FIG. 46, (A) is the TIC, (B) is the XIC for m/z 1479.4, corresponding to cyclic phosphate, (C) is the MS corresponding to peak retention time at 32.94 min depicting the doubly charged ions, and (D) is the CID-based sequencing of UGGAA[m$^7$G]UC[m5C] with a 2'-3' cyclic phosphate. A portion of the observed sequence informative product ions ($c_n$ having a common 5'-end and $y_n$ having a common 3'-end) are shown in the spectrum. The characteristic product ion that corresponds to the loss of [m$^7$G] from the molecular ion, which is at the highest abundance (m/z 1396.2), is shown.

Figure 47:
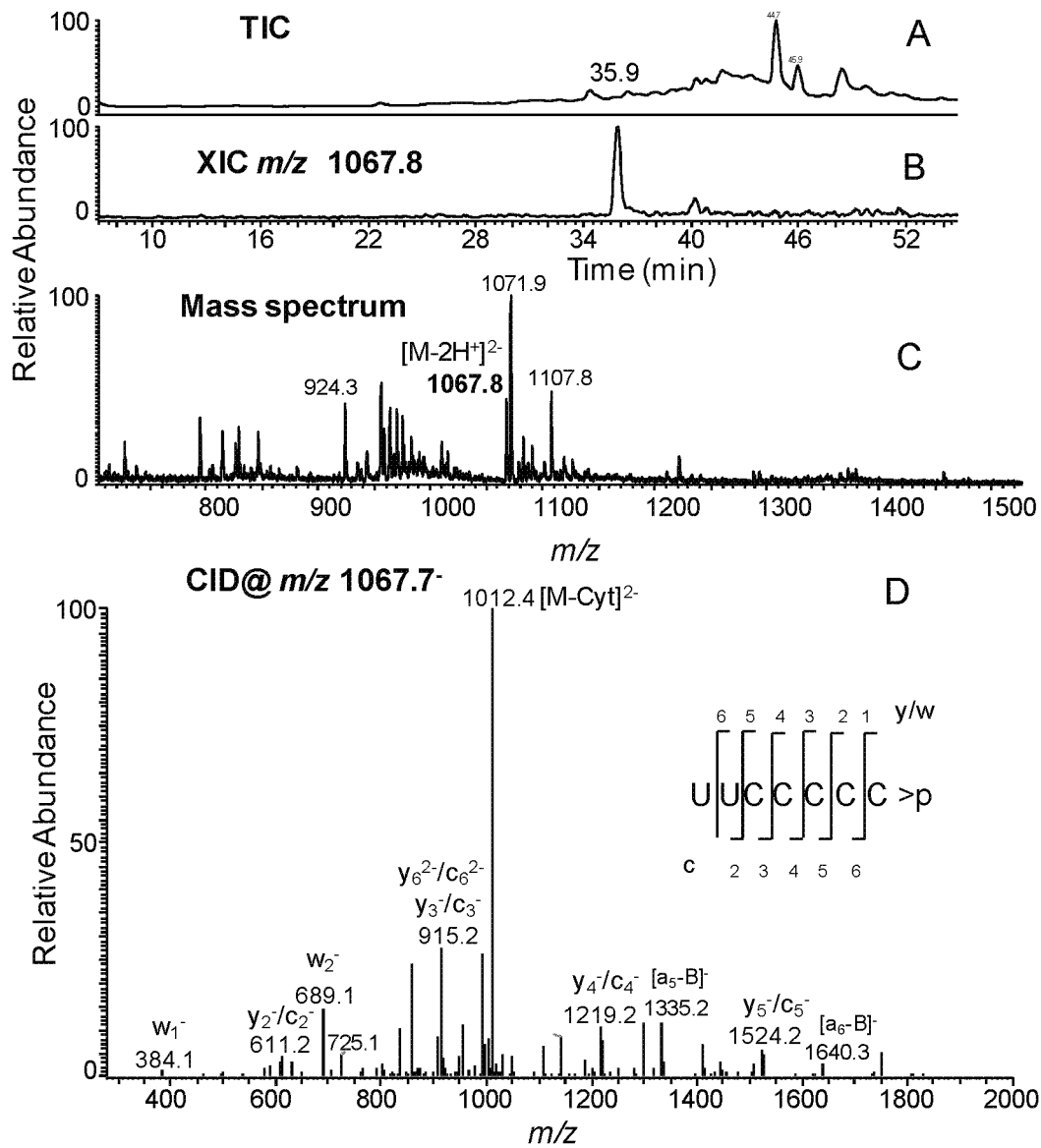
FIG. 47 shows an LC-MS analysis of Cusativin digestion product.

Although Cusativin exhibits cytidine-specific cleavage of RNA, Cusativin exhibits a lower rate of cleaveage of the phosphodiester bond between multiple cytidines in tandem, as shown in FIG. 47. FIG. 47 shows an LC-MS analysis of Cusativin digestion product, UUCCCCC>p, from yeast tRNA$^{Phe}$. (A) is the TIC, (B) is the XIC for m/z 1067.8, corresponding to cyclic phosphate, (C) is the MS corresponding to peak retention time at 35.9 min depicting the doubly charged ions, and (E) is the CID-based sequencing of UUCCCCC>p. A portion of the observed sequence informative product ions ($c_n$ with a common 5'-end and $y_n$ with a common 3'-end) are shown in the spectrum.

This has been a description of the present invention along with the various methods of practicing the present invention. However, the invention itself should only be defined by the appended claims.

What is claimed is:

1. A polynucleotide encoding a cytidine-specific recombinant RNase Cusativin, wherein the polynucleotide comprises the nucleotide sequence of SEQ ID NO. 4.

* * * * *

UNITED STATES PATENT AND TRADEMARK OFFICE
CERTIFICATE OF CORRECTION

PATENT NO. : 10,533,163 B2  
APPLICATION NO. : 15/568260  
DATED : January 14, 2020  
INVENTOR(S) : Sarah Venus et al.

Page 1 of 1

It is certified that error appears in the above-identified patent and that said Letters Patent is hereby corrected as shown below:

In the Specification

Column 1, Lines 19-23, "This invention was made with government support under Grant No. CHE-1156449 awarded by the National Science Foundation and under Grant No. GM058843 awarded by the National Institutes of Health. The U.S. Government may have certain rights in this invention." should be --This invention was made with government support under GM058843 awarded by National Institutes of Health and CHE1156449 awarded by National Science Foundation. The government has certain rights in the invention.--.

Column 1, Line 38, "recombinant ribonucleases, and more particularly, to" should be --recombinant ribonucleases and, more particularly, to--.

Column 4, Line 4, "FIG." should be --FIGS.--.

Column 4, Lines 53-54, "the RNase MC1 has SEQ ID NO. 1 In another embodiment," should be --the RNase MC1 has SEQ ID NO. 1. In another embodiment,--.

Column 5, Line 42, "After the expression conditions for the host was" should be --After the expression conditions for the host were--.

Column 12, Line 67, "Fisher scientific)." should be --Fisher Scientific).--.

Column 15, Line 66, "42°C. for 2 min, and then put back on ice for 2 min 200 μL SOC media was added" should be --42°C. for 2 min, and then put back on ice for 2 min. 200 μL SOC media was added--.

Column 18, Line 51, "are shown" should be --is shown--.

Signed and Sealed this  
Sixteenth Day of June, 2020

Andrei Iancu  
*Director of the United States Patent and Trademark Office*